US011242399B2

(12) United States Patent
Di Naro

(10) Patent No.: US 11,242,399 B2
(45) Date of Patent: *Feb. 8, 2022

(54) ANTI-CD26 ANTIBODIES

(71) Applicant: ADIENNE S.A., Lugano (CH)

(72) Inventor: Antonio Francesco Di Naro, Morcote (CH)

(73) Assignee: ADIENNE S.A., Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/230,877

(22) Filed: Dec. 21, 2018

(65) Prior Publication Data

US 2019/0352417 A1 Nov. 21, 2019

Related U.S. Application Data

(60) Continuation-in-part of application No. 15/169,386, filed on May 31, 2016, now Pat. No. 10,208,126, which is a division of application No. 14/184,241, filed on Feb. 19, 2014, now Pat. No. 9,376,498.

(60) Provisional application No. 61/813,875, filed on Apr. 19, 2013.

(30) Foreign Application Priority Data

Feb. 19, 2013 (EP) .................................... 13425029

(51) Int. Cl.

| | |
|---|---|
| ***C07K 16/18*** | (2006.01) |
| ***A61K 39/395*** | (2006.01) |
| ***C07K 16/28*** | (2006.01) |
| ***A61P 7/06*** | (2006.01) |
| ***C07K 16/40*** | (2006.01) |
| ***A61P 37/06*** | (2006.01) |
| *A61K 39/00* | (2006.01) |

(52) U.S. Cl.

CPC ...... *C07K 16/2896* (2013.01); *A61K 39/3955* (2013.01); *A61P 7/06* (2018.01); *A61P 37/06* (2018.01); *C07K 16/40* (2013.01); *A61K 2039/505* (2013.01); *A61K 2039/545* (2013.01); *C07K 2317/24* (2013.01); *C07K 2317/33* (2013.01); *C07K 2317/34* (2013.01); *C07K 2317/565* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 7,666,425 | B1 | 2/2010 | Bander | |
| 8,846,393 | B2 | 9/2014 | Peled | |
| 9,376,498 | B2 * | 6/2016 | Di Naro | A61P 37/06 |
| 10,208,126 | B2 * | 2/2019 | Di Naro | C07K 16/40 |
| 2007/0060528 | A1 | 3/2007 | Christopher et al. | |
| 2009/0136523 | A1 * | 5/2009 | Aoyagi | A61P 37/02 424/174.1 |
| 2012/0045435 | A1 | 2/2012 | Deisher | |

FOREIGN PATENT DOCUMENTS

| | | | |
|---|---|---|---|
| EP | 1 179 542 | A1 | 2/2002 |
| RU | 2331881 | C1 | 8/2008 |
| WO | WO 02/092127 | A1 | 11/2002 |
| WO | WO 2007/014169 | A2 | 2/2007 |

OTHER PUBLICATIONS

D'Angelo et al., Many Routes to an Antibody Heavy-Chain CDR3: Necessary, Yet Insufficient, for Specific Binding, Frontiers in Immunology vol. 9, Article 395 Mar. 2018; doi:10.3389/fimmu.2018.00395. (Year: 2018).*

Piche-Nicholas et al., Changes in complemetarity-determining regions significantly alter IgG binding to the neonatal Fc receptor (FcRN) and pharmacokinetics, MABS 2018, vol. 10, No. 1, 81-94, doi.org/10.1080/19420862.2017.1389355. (Year: 2018).*

Akpek, G., et al., "Hepatic variant of graft-versus-host disease after donor lymphocyte infusion," *Blood* 100(12):3903-3907, The American Society of Hematology, United States (2002).

Franzke, A., et al., "Identification of novel regulators in T-cell differentiation of aplastic anemia patients," *BMC Genomics* 7:263-273, 11 pages, BioMed Central Ltd., England (2006).

Aytac, U., et al., "Effect of CD26/dipeptidyl peptidase IV on Jurkat sensitivity to G2/M arrest induced by topoisomerase II inhibitors," *British Journal of Cancer* 88:455-462, Cancer Research UK, England (2003).

Bacigalupo, A. and Passweg, J., "Diagnosis and Treatment of Acquired Aplastic Anemia," *Hematol Oncol Clin N Am* 23:159-170, Elsevier Inc., United States (2009).

Broxmeyer, H.E., "Umbilical Cord Blood Stem Cells: Collection, Processing, and Transplantation," *Blood Banking and Transfusion Medicine Second Edition*: Chapter 59, pp. 823-832, Elsevier, Inc., United States (2007).

Broxmeyer, H.E., et al., "AMD3100 and CD26 Modulate Mobilization, Engraftment, and Survival of Hematopoietic Stem and Progenitor Cells Mediated by the SDF-1/CXCL12-CXCR4 Axis," *Ann N.Y. Acad Sci* 1106:1-19, New York Academy of Sciences, United States (2007).

(Continued)

*Primary Examiner* — Phillip Gambel

(74) *Attorney, Agent, or Firm* — Sterne, Kessler, Goldstein & Fox P.L.L.C.

(57) ABSTRACT

The present invention pertains to novel antibodies capable of binding to CD26, as well as to their use as a medicament. Moreover, the present invention provides antibodies for use in treating and/or preventing Graft-versus-Host Disease (GvHD), for use in treating Aplastic Anemia and/or for use in promoting engraftment after haematopoietic stem cell transplantation. Furthermore, the present invention provides pharmaceutical compositions comprising at least one antibody of the present invention, as well as provides a kit of parts.

17 Claims, 13 Drawing Sheets

Specification includes a Sequence Listing.

(56) References Cited

OTHER PUBLICATIONS

Busso, N., et al., "Circulating CD26 Is Negatively Associated with Inflammation in Human and Experimental Arthritis," *American Journal of Pathology* 166(2):433-442, American Society for Investigative Pathology, United States (2005).
Campbell, T.B., et al., "Inhibition of CD26 in Human Cord Blood $CD34^+$Cells Enhances Their Engraftment of Nonobese Diabetic/Severe Combined Immunodeficiency Mice," *Stem Cells and Development* 16:347-353, Mary Ann Liebert Inc., United States (2007).
Christopherson, K.W., et al., "Modulation of Hematopoietic Stem Cell Homing and Engraftment by CD26," *Science* 305:1000-1003, American Association for the Advancement of Science, United States (2004).
Charo, I.F., et al., "Chemokine Receptor 2 (CCR2) in Atherosclerosis, Infectious Diseases, and Regulation of T-Cell Polarization," *Microcirculation* 10:259-264, Nature Publishing Group, England (2003).
Christopherson, K.W., et al., "Cell Surface Peptidase CD26/Dipeptidylpeptidase IV Regulates CXCL12/Stromal Cell-Derived Factor-1α-Mediated Chemotaxis of Human Cord Blood $CD34_+$ Progenitor Cells," *The Journal of Immunology* 169:7000-7008, The American Association of Immunologists, Inc., United States (2002).
Christopherson, K.W., et al., "Cell surface peptidase CD26/DPPIV mediates G-CSF mobilization of mouse progenitor cells," *Blood* 101(12)A680A686, The American Society of Hematology, United States (2003).
Christopherson, K.W., et al., "CD26 Inhibition on $CD34^+$or Lineage' Human Umbilical Cord Blood Donor Hematopoietic Stem Cells/Hematopoietic Progenitor Cells Improves Long-Term Engraftment into NOD/SCID/$Beta^{null}$ Immunodeficient Mice," *Stem Cells and Development* 16:355-360, Mary Ann Liebert Inc., United States (2007).
Christopherson, K.W., et al., "CD26 is essential for normal G-CSF-induced progenitor cell mobilization as determined by $CD26^{-/-}$mice," *Experimental Hematology* 31:1126-1134, Elsevier Inc., United States (2003).
Dang, N.H. and Morimoto, C., "CD26: An expanding role in immune regulation and cancer," *Histology and Histopathology* 17:1213-1226, Gutenberg, Spain (2002).
Dong, R-P., et al. "Correlation of the epitopes defined by anti-CD26 mAbs and CD26 function," *Molecular Immunology* 35:13-21, Pergamon Press, England (1998).
Dong, R-P., et al. "Characterization of Adenosine Deaminase Binding to Human CD26 on T Cells and Its Biologic Role in Immune Response," *The Journal of Immunology* 156:1349-1355, American Association of Immunologists, United States (1996).
Drucker, D.J., "Dipeptidyl Peptidase-4 Inhibition and the Treatment of Type 2 Diabetes," *Diabetes Care* 30(6):1335-1343, The American Diabetes Association, United States (2007).
Durinx, C., et al., "Molecular characterization of dipeptidyl peptidase activity in serum," *European Journal of Biochemistry* 267:5608-5613, FEBS, Netherlands (2000).
Ferrara, J.L.M., etal, "Graft-versus-Host Disease," *Lancet* 373(9674):1550-1561, Lancet Publishing Group, England (2009).
Fleischer, B., "A Novel Pathway of Human T Cell Activation via a 103 kD T Cell Activation Antigen," *The Journal of Immunology* 138:1346-1350, The American Association of Immunologists, United States (1987).
Fleischer, B., et al., "Triggering of Cytotoxic T Lymphocytes and NK Cells Via the Tpl03 Pathway is Dependent on the Expression of the T Cell Receptor/CD3 Complex," *The Journal of Immunology* 141(4):1103-1107, The American Association of Immunologists, United States (1988).
Fleischer, B., "CD26: a surface protease involved in T-cell Activation," *Immunology Today* 15(4):180-184, Elsevier Science Ltd., England (1994).
Fox, D.A., et al., "$Ta_1$, A Novel 105 kD Human T Cell Activation Antigen Defined by a Monoclonal Antibody," *The Journal of Immunology* 755(3):1250-1256, The American Association of Immunologists, United States (1984).
Fraticelli, P., et al., "Fractalkine (CX3CL1) as an amplification circuit of polarized Th1 Responses," *J. Clin. Invest.* 107:1173-1181, American Society for Clinical Investigation, United States (2001).
Guo, Y., et al., "SDF-1/CXCL12 Enhances Survival and Chemotaxis of Murine Embryonic Stem Cells and Production of Primative and Definitive Hematopoietic Progenitor Cells," *Stem Cells* 25:1324-1332, AlphaMed Press, United States (2005).
Glucksberg, H., et al., "Clinical Manifestations of Graft-versus-Host Disease in Human Recipients of Marrow from HL-A-Matched Sibling Donors," *Transplantation* 18(4):295-304, The Williams & Wilkins Co., United States (1974).
Hegen, M., et al., "The T Cell Triggering Molecule Tp103 is Associated with Dipeptidyl Aminopeptidase IV Activity," *The Journal of Immunology* 144(8):2908-2914, The American Association of Immunologists, United States (1990).
Hopsu-Havu, V.K. and Glenner, G.G., "A New Dipeptide Naphthylamidase Hydrolyzing Glycyl-Prolyl-β-Naphthylamide," *Histochemie* 7(3):197-201, Springer-Verlag, Berlin, Germany (1966).
Hatano, R., et al., "CD26 Blockade by Humanized Monoclonal Antibody Leads to Prophylaxis and Treatment of Graft-Versus-Host Disease (GVHD) in Hu-PBL-NOG Model Mice," $53^{rd}$ Annual Meeting and Exposition of The American-Society-Of-Hematology, Abstract 4018, Dec. 10-13, 2 pages (2011).
Jacobsohn, D.A. and Vogelsang, G.B., "Acute graft versus host disease," *Orphanet Journal of Rare Diseases* 2:35-44, BioMed Central Ltd., London, England (2007).
Jee, Y., et al., "Upregulation of monocyte chemotactic protein-1 and CC chemokine receptor 2 in the central nervous system is closely associated with relapse of autoimmune encephalomyelitis in Lewis rats," *Journal of Neuroimmunology* 128:49-57, Elsevier, Amsterdam, Netherlands (2002).
Jung, F.J., et al., "CD26/Dipeptidylpeptidase IV-targeted Therapy of Acute Lung Rejection in Rats," *J Heart and Lung Transplant.* 25(9):1109-1116, Elsevier, United States (2006).
Kähne, T., et al., "Dipeptidyl peptidase IV: A cell surface peptidase involved in regulating T cell growth (Review)," *International Journal of Molecular Medicine* 4:3-15, Spandidos, Athens, Greece (1999).
Kameoka, J., et al., "Direct Association of Adenosine Deaminase with a T Cell Activation Antigen, CD26," *Science* 261(5120)466-469, American Association for the Advancement of Science, United States (1993).
Kawai, T., et al., "Diprotin A Infusion into Nonobese Diabetic/Severe Combined Immunodeficiency Mice Markedly Enhances Engraftment of Human Mobilized $CD34_+$Peripheral Blood Cells," *Stem Cells and Development* 16(3):361-370, Mary Ann Liebert, Inc., United States (2007).
Kim, S-J., et al., "Sitagliptin (MK0431) Inhibition of Dipeptidyl Peptidase IV Decreases Nonobese Diabetic Mouse $CD4^+$T-Cell Migration Through Incretin-Dependent and -Independent Pathways," *Diabetes* 59(7):1739-1750, American Diabetes Association, United States (2010).
Hatano, R., et al., "A Novel Function of CD26-Mediated Costimulation in the Cytotoxic Activity of Human CD8+ T Cells in Xenogeneic Chronic Graft-Versus-Host Disease (cGVHD) and GVL Mice Model," $51^{st}$ Ash Annual Meeting and Exposition of The American-Society-Of-Hematology, Abstract 3548, Dec. 5-8, 2 pages (2009).
Lewis, I.D., "Clinical and experimental uses of umbilical cord blood," *Internal Medicine Journal* 32:601-609, Blackwell Science Asia, Carlton, Australia (2002).
Maciejewski, J., et al., "Fas Antigen Expression on $CD34^+$Human Marrow Cells Is Induced by Interferon γ and Tumor Necrosis Factor α and Potentiates Cytokine-Mediated Hematopoietic Suppression In Vitro," *Blood* 85(11):3183-3190, The American Society of Hematology, United States (1995).
Maciejewski, J.P., et al., "Increased expression of Fas antigen on bone marrow $CD34^+$cells of patients with aplastic anaemia," *British Journal of Haematology*, 91:245-252, Blackwell Science Ltd., Oxford, England (1995).

(56) References Cited

OTHER PUBLICATIONS

Dominietto, A., "Dichiarazione," XII Congresso Nazionale Sies 2012, Oct. 17-19, 27 pages (2012).
Unknown Author, "Public summary of opinion on orphan designation," European Medicines Agency Science Medicines Health, Jan. 20, 4 pages (2014).
Morimoto, C., et al.," 1F7, a novel cell surface molecule, involved in helper function of CD4 cells," *The Journal of Immunology* 145(11):3430-3439 The American Association of Immunologists, United States (1989).
Morimoto, C. and Schlossman, S.F., "A Key Costimulatory Molecule on CD4 Memory T Cells," *The Immunologist* 2(1):4-7, Hogrefe & Huber Publishers, Switzerland (1994).
Morrison, M.E., et al.," A Marker for Neoplastic Progression of Human Melanocytes Is a Cell Surface Ectopeptidase," *J. Exp. Med.* 177(4):1135-1143, Rockefeller University Press, United States (1993).
Nakao, S., et al., "Isolation of a T-Cell Clone Showing HLA-DRB1*0405-Restricted Cytotoxicity for Hematopoietic Cells in a Patient With Aplastic Anemia," *Blood* 89(10):3691-3699, The American Society of Hematology, United States (1997).
Hatano, R., et al., "Prevention of acute graft-versus-host disease by humanized anti-CD26 monoclonal antibody," *British Journal of Haematology* 762:263-277, John Wiley & Sons Ltd., United States (2013).
International Search Report for International Application No. PCT/EP2014/053243, European Patent Office, Netherlands, dated Apr. 9, 2014.
Peranteau, W.H., et al., "CD26 inhibition enhances allogeneic donor-cell homing and engraftment after in utero hematopoietic-cell transplantation," *Blood* 108:4268-4274, The American Society of Hematology, United States (2006).
Zeng, W., et al., "Limited heterogeneity of T cell receptor BV usage in aplastic anemia," *J. Clin. Invest.* 108(5):765-773, Am. Society for Clinical Investigation, United States (2001).
Zeng, W., et al., "Characterization of T-Cell Repertoire of the Bone Marrow in Immune-Mediated Aplastic Anemia: Evidence for the Involvement of Antigen-Driven T-Cell Response in Cyclosporine-Dependent Aplastic Anemia," *Blood* 93(9):3008-3016, Grune & Stratton, United States (1999).
Risitano, A.M., et al., "Oligoclonal and polyclonal CD4 and CD8 lymphocytes in aplastic anemia and paroxysmal nocturnal hemoglobinuria measured by Vβ CDR3 spectratyping and flow cytometry," *Blood* 100(1):178-183, Am. Society of Hematology, United States (2002).
Young, N.S., "The Pathophysiology of Acquired Aplastic Anemia," *N. Engl. J. Med.* 336(19):1365-1372, Massachusetts Medical Society, United States (1997).
Steinbrecher, A., et al., "Targeting Dipeptidyl Peptidase IV (CD26) Suppresses Autoimmune Encephalomyelitis and Up-Regulates TGF-β1 Secretion In Vivo," *J. Immunol* 166:2041-2048, American Association of Immunologists, United States (2001).
Sun, Y., et al., "Pathophysiology of Acute Graft-vs-Host Disease: Recent Advances," *Transl Res.* 150(4):197-214, Elsevier, United States (2007).
Tian, C., et al., "Inhibition of CD26 peptidase activity significantly improves engraftment of retrovirally transduced hematopoietic progenitors," *Gene Therapy* 13:652-658, Nature Publishing Group, London, England (2006).
Ulmer, A.J., et al., "CD26 Antigen is a Surface Dipeptidyl Peptidase IV (DPPIV) as Characterized by Monoclonal Antibodies Clone TII-19-4-7 and 4EL1C7," *Scand. J. Immunol.* 37:429-435, Universitetsforlaget, Oslo, England (1990).
Vanham, G., et al., "Decreased Expression of the Memory Marker CD26 on Both $CD4^+$and $CDS^+$T Lymphocytes of HIV-Infected Subjects," *Journal of Acquired Immune Deficiency Syndromes* 6:749-757, Raven Press. Ltd., United States (1993).
Willheim, M., et al. "Cell surface characterization of T lymphocytes and allergen-specific T cell clones: Correlation of CD26 expression with $T_{H1}$ subsets," *J. Allergy Clin. Immunol.* 100(3):348-355, Mosby-Year Book, Inc., United States (1997).
Campbell, T.B. and Broxmeyer, H.E., "CD26 inhibition and hematopoiesis: a novel approach to enhance transplantation," *Frontiers in Bioscience* 73:1795-1805, Frontiers in Bioscience Publications, United States (2008).
Farag, S.S., et al., "In Vivo DPP-4 Inhibition to Enhance Engraftment of Single-Unit Cord Blood Transplants in Adults with Hematological Malignancies," *Stem Cells and Development* 22(7):1007-1015, Mary Ann Leibert, United States (2013).
Dominietto, Alida: "CD26, anti-CD26 and Gvhd," XII Congresso Nazionale SIES 2012, Oct. 19, 2012 (Oct. 19, 2012), 27 slides, Retrieved at http://www.siesonline.it/en/wp-content/uploads/2013/05/21.pdf.
Hatano, R., et al., "CD26 Blockade by Humanized Monoclonal Antibody Leads to Prophylaxis and Treatment of Graft-Versus-Host Disease (GVHD) in Hu-PBL-NOG Model Mice,." Blood 118(21): Abstract 4018, Accessed Feb. 22, 2017 at http://www.bloodjournal.org/content/118/21/4018 (2011).
Yoo, E., et al., "Loss of CD26 Protease Activity in Recipient Mice during Hemapoietic Stem Cell Transplantation Results in Improved Transplant Efficiency," *Transfusion* 53(4):878-887, American Association Of Blood Banks, United States (2013).
Rudikoff, S., et al., "Single Amino Acid Substitution Altering Antigen-Binding Specificity," PNAS 79:1979-198, United States National Academy of Sciences (1982).
Colman, P.M., et al., "Effects of amino acid sequence changes on antibody-antigen interactions," Research in Immunology 145: 33-36, Elsevier, Netherlands (1994).
Kussie, P.H., et al., "A single engineered amino acid substitution changes antibody fine specificity," J Immunol 152:146-152, American Association of Immunologists, United States (1994).
Chen, C., et al., "Enhancement and destruction of antibody function by somatic mutation: unequal occurrence is controlled by V gene combinatorial associations,".
Healthcommunicites.com, What is Aplastic Anemia, published Aug. 17, 2011, last modified Oct. 2, 2014, downloaded at healthcommunities.com/anemia/what-is-aplastic-anemia.shtml on Sep. 11, 2017.
Harvard Health Publications Aplastic Anemia, published Feb. 2013; downloaded Sep. 10, 2017 at health. harvard. edu/hearthealth/aplastic-anemia.
Ackermann, M., et al., "Influence of cell- and media-derived factors on the integrity of a human monoclonal antibody after secretion into serum-free cell culture supernatants," Biotechnology and Bioengineering 45:97-106, John Wiley & Sons, (1995).

* cited by examiner

FIG. 1a – CD26 human sequence according to GenBank: BAG70302.1 (SEQ ID NO: 144)

```
>gi|197692677|dbj|BAG70302.1| dipeptidylpeptidase IV [Homo sapiens]
MKTPWKVLLGLLGAAALVTIITVPVVLLNKGTDDATADSRKTYTLTDYLKNTYRLKLYSLRWISDHEYLY
KQENNILVFNAEYGNSSVFLENSTFDEFGHSINDYSISPDGQFILLEYNYVKQWRHSYTASYDIYDLNKR
QLITEERIPNNTQWVTWSPVGHKLAYVWNNDIYVKIEPNLPSYRITWTGKEDIIYNGITDWVYEEEVFSA
YSALWWSPNGTFLAYAQFNDTEVPLIEYSFYSDESLQYPKTVRVPYPKAGAVNPTVKFFVVNTDSLSSVT
NATSIQITAPASMLIGDHYLCDVTWATQERISLQWLRRIQNYSVMDICDYDESSGRWNCLVARQHIEMST
TGWVGRFRPSEPHFTLDGNSFYKIISNEEGYRHICYFQIDKKDCTFITKGTWEVIGIEALTSDYLYYISN
EYKGMPGGRNLYKIQLSDYTKVTCLSCELNPERCQYYSVSFSKEAKYYQLRCSGPGLPLYTLHSSVNDKG
LRVLEDNSALDKMLQNVQMPSKKLDFIILNETKFWYQMILPPHFDKSKKYPLLLDVYAGPCSQKADTVFR
LNWATYLASTENIIVASFDGRGSGYQGDKIMHAINRRLGTFEVEDQIEAARQFSKMGFVDNKRIAIWGWS
YGGYVTSMVLGSGSGVFKCGIAVAPVSRWEYYDSVYTERYMGLPTPEDNLDHYRNSTVMSRAENFKQVEY
LLIHGTADDNVHFQQSAQISKALVDVGVDFQAMWYTDEDHGIASSTAHQHIYTHMSHFIKQCFSLP
```

FIG. 1b – CD26 porcine sequence according to GenBank: BAG70302.1 (SEQ ID NO: 145)

```
>gi|47523582|ref|NP_999422.1| dipeptidyl peptidase 4 [Sus scrofa]
MKTPWKVLLGLLGIAALVTVITVPVVLLNKGTDDAAADSRRTYTLTDYLKSTFRVKFYTLQWISDHEYLY
KQENNILLFNAEYGNSSIFLENSTFDELGYSTNDYSVSPDRQFILFEYNYVKQWRHSYTASYDIYDLNKR
QLITEERIPNNTQWITWSPVGHKLAYVWNNDIYVKNEPNLSSQRITWTGKENVIYNGVTDWVYEEEVFSA
YSALWWSPNGTFLAYAQFNDTEVPLIEYSFYSDESLQYPKTVRIPYPKAGAENPTVKFFVVDTRTLSPNA
SVTSYQIVPPASVLIGDHYLCGVTWVTEERISLQWIRRAQNYSIIDICDYDESTGRWISSVARQHIEIST
TGWVGRFRPAEPHFTSDGNSFYKIISNEEGYKHICHFQTDKSNCTFITKGAWEVIGIEALTSDYLYYISN
EHKGMPGGRNLYRIQLNDYTKVTCLSCELNPERCQYYSASFSNKAKYYQLRCFGPGLPLYTLHSSSSDKE
LRVLEDNSALDKMLQDVQMPSKKLDVINLHGTKFWYQMILPPHFDKSKKYPLLIEVYAGPCSQKVDTVFR
LSWATYLASTENIIVASFDGRGSGYQGDKIMHAINRRLGTFEVEDQIEATRQFSKMGFVDDKRIAIWGWS
YGGYVTSMVLGAGSGVFKCGIAVAPVSKWEYYDSVYTERYMGLPTPEDNLDYYRNSTVMSRAENFKQVEY
LLIHGTADDNVHFQQSAQLSKALVDAGVDFQTMWYTDEDHGIASNMAHQHIYTHMSHFLKQCFSLP
```

FIG. 1c – Aligned CD26 human (*Homo*) and porcine (*Sus*)

```
Homo  1    MKTPWKVLLGLLGAAALVTIITVPVVLLNKGTDDATADSRKTYTLTDYLKNTYRLKLYSL  60
Sus   1    .............I.....V...............A....R.........S.F.V.F.T.  60

Homo  61   RWISDHEYLYKQENNILVFNAEYGNSSVFLENSTFDEFGHSINDYSISPDGQFILLEYNY  120
Sus   61   Q................L.........I.........L.Y.T....V...R....F....  120

Homo  121  VKQWRHSYTASYDIYDLNKRQLITEERIPNNTQWVTWSPVGHKLAYVWNNDIYVKIEPNL  180
Sus   121  ..................................I....................N....  180

Homo  181  PSYRITWTGKEDIIYNGITDWVYEEEVFSAYSALWWSPNGTFLAYAQFNDTEVPLIEYSF  240
Sus   181  S.Q........NV....V..........................................  240

Homo  241  YSDESLQYPKTVRVPYPKAGAVNPTVKFFVVNTDSLSSVTNATSIQITAPASMLIGDHYL  300
Sus   241  .............I.......E.........D.RT..PNASV..Y..VP...V.......  300

Homo  301  CDVTWATQERISLQWLRRIQNYSVMDICDYDESSGRWNCLVARQHIEMSTTGWVGRFRPS  360
Sus   301  .G...V.E.......I..A....II........T...ISS.......I...........A  360

Homo  361  EPHFTLDGNSFYKIISNEEGYRHICYFQIDKKDCTFITKGTWEVIGIEALTSDYLYYISN  420
Sus   361  .....S...............K...H..T..SN.......A...................  420

Homo  421  EYKGMPGGRNLYKIQLSDYTKVTCLSCELNPERCQYYSVSFSKEAKYYQLRCSGPGLPLY  480
Sus   421  .H..........R...N.....................A...NK........F.......  480

Homo  481  TLHSSVNDKGLRVLEDNSALDKMLQNVQMPSKKLDFIILNETKFWYQMILPPHFDKSKKY  540
Sus   481  .....SS..E...............D.........V.N.HG...................  540

Homo  541  PLLLDVYAGPCSQKADTVFRLNWATYLASTENIIVASFDGRGSGYQGDKIMHAINRRLGT  600
Sus   541  ...IE.........V......S......................................  600

Homo  601  FEVEDQIEAARQFSKMGFVDNKRIAIWGWSYGGYVTSMVLGSGSGVFKCGIAVAPVSRWE  660
Sus   601  .........T..........D....................A...............K..  660

Homo  661  YYDSVYTERYMGLPTPEDNLDHYRNSTVMSRAENFKQVEYLLIHGTADDNVHFQQSAQIS  720
Sus   661  .....................Y....................................L.  720

Homo  721  KALVDVGVDFQAMWYTDEDHGIASSTAHQHIYTHMSHFIKQCFSLP  766
Sus   721  .....A.....T............NM............L.......  766
```

FIG. 2a – CDR3 sequences, which can be present in an antibody according to the present invention.

| Name | Seq. ID | Sequence |
|---|---|---|
| CDR 3 Heavy group 1 | SEQ 1 | WTVVGPGYFDV |
| CDR 3 Light prevalent group 1 | SEQ 2 | QQRSSYPNT |
| CDR 3 Light group 3 | SEQ 3 | GQGYSYPYT |

FIG. 2b – List of the sequences of the VH CDR1, VH CDR2, VH CDR3, VL CDR1, VL CDR2, and VL CDR3 of CD26 specific antibodies.

| $V_H$/ $V_L$ | CDR1 | CDR2 | CDR3 |
|---|---|---|---|
| $V_H$ Group 1 | GYTFRSYDIN<br>SEQ ID NO: 133 | WIFPGDGSTKYNEKFKG<br>SEQ ID NO: 134 | WTVVGPGYFDV<br>SEQ ID NO: 1 |
| $V_L$ Group 1 | SASSSVSYMN<br>SEQ ID NO: 129 | STSNLAS<br>SEQ ID NO: 130 | QQRSSYPNT<br>SEQ ID NO: 2 |
| $V_L$ Group 3 | KASENVVTYVS<br>SEQ ID NO: 131 | GASNRYT<br>SEQ ID NO: 132 | GQGYSYPYT<br>SEQ ID NO: 3 |

FIG. 2c – List of the sequences of the VH ABR1, VH ABR2, VH ABR3, VL ABR1, VL ABR2, and VL ABR3 of CD26 specific antibodies.

| $V_H$/ $V_L$ | ABR1 | ABR2 | ABR3 |
|---|---|---|---|
| $V_H$ Group 1 | YTFRSYDIN<br>SEQ ID NO: 141 | WIGWIFPGDGSTKY<br>SEQ ID NO: 142 | RWTVVGPGYFDV<br>SEQ ID NO: 143 |
| $V_L$ Group 1 | SSVSYMN<br>SEQ ID NO: 135 | LWIYSTSNLAS<br>SEQ ID NO: 136 | QQRSSYPN<br>SEQ ID NO: 137 |
| $V_L$ Group 3 | ENVVTYVS<br>SEQ ID NO: 138 | LLIYGASNRYT<br>SEQ ID NO: 139 | GQGYSYPY<br>SEQ ID NO: 140 |

FIG. 3a – Sequences similarity, seen in the various VH and VL regions, which can be present in an antibody according to the present invention, with CDRs.

VH

```
                                     CDR 1                 CDR 2
SEQ22    EVKLQESGAELVKPGASVKLSCKASGYTFRSYDINWVRQRPEQGLEWIGWIFPGDGSTKY 60
SEQ42    EVKLMESGAELVKPGASVKLSCKASGYTFRSYDINWVRQRPEQGLEWIGWIFPGDGSTKY 60
SEQ30    QVKLQESGAELVKPGASVKLSCKASGYTFRSYDINWVRQRPEQGLEWIGWIFPGDGSTKY 60
SEQ38    DVKLQESGAELVKPGASVKLSCKASGYTFRSYDINWVRQRPEQGLEWIGWIFPGDGSTKY 60
SEQ29    EVQLQQSGAELVKPGASVKLSCKASGYTFRSYDINWVRQRPEQGLEWIGWIFPGDGSTKY 60
SEQ46    EVQLQQSGAELVKPGASVKLSCKASGYTFRSYDINWVRQRPEQGLEWIGWIFPGDGSTKY 60
SEQ24    EVQLQQSGAELVKPGASVKLSCKASGYTFRSYDINWVRQRPEQGLEWIGWIFPGDGSTKY 60
SEQ34    EVQLQQSGAELVKPGASVKLSCKASGYTFRSYDINWVRQRPEQGLEWIGWIFPGDGSTKY 60
SEQ41    EVQLHQSGAELVKPGASVKLSCKASGYTFRSYDINWVRQRPEQGLEWIGWIFPGDGSTKY 60
SEQ31    EVKLQQSGAELVKPGASVKLSCKASGYTFRSYDINWVRQRPEQGLEWIGWIFPGDGSTKY 60
SEQ26    QVQLQQSGAELVKPGASVKLSCKASGYTFRSYDINWVRQRPEQGLEWIGWIFPGDGSTKY 60
SEQ43    XVQLQXSGAELVKPGASVKLSCKASGYTFRSYDINWVRQRPEQGLEWIGWIFPGDGSTKY 60
SEQ27    EVQLQESGAELVKPGASVKLSCKASGYTFRSYDINWVRQRPEQGLEWIGWIFPGDGSTKY 60
SEQ28    QVQLQESGAELVKPGASVKLSCKASGYTFRSYDINWVRQRPEQGLEWIGWIFPGDGSTKY 60
SEQ33    DVQLQESGAELVKPGASVKLSCKASGYTFRSYDINWVRQRPEQGLEWIGWIFPGDGSTKY 60
SEQ35    QVQLKESGAELVKPGASVKLSCKASGYTFRSYDINWVRQRPEQGLEWIGWIFPGDGSTKY 60
SEQ45    EVQLKESGAELVKPGASVKLSCKASGYTFRSYDINWVRQRPEQGLEWIGWIFPGDGSTKY 60
SEQ32    EVKVVESGAELVKPGASVKLSCKASGYTFRSYDINWVRQRPEQGLEWIGWIFPGDGSTKY 60
SEQ44    EVKVVESGAELVKPGASVKLSCKASGYTFRSYDINWVRQRPEQGLEWIGWIFPGDGSTKY 60
SEQ23    EVKLVESGAELVKPGASVKLSCKASGYTFRSYDINWVRQRPEQGLEWIGWIFPGDGSTKY 60
SEQ36    EVMLVESGAELVKPGASVKLSCKASGYTFRSYDINWVRQRPEQGLEWIGWIFPGDGSTKY 60
SEQ37    EVXLVESGAELVKPGASVKLSCKASGYTFRSYDINWVRQRPEQGLEWIGWIFPGDGSTKY 60
SEQ25    EVQGVESGAELVKPGASVKLSCKASGYTFRSYDINWVRQRPEQGLEWIGWIFPGDGSTKY 60
SEQ47    EVQRVESGAELVKPGASVKLSCKASGYTFRSYDINWVRQRPEQGLEWIGWIFPGDGSTKY 60
SEQ39    EVQLVESGAELVKPGASVKLSCKASGYTFRSYDINWVRQRPEQGLEWIGWIFPGDGSTKY 60
SEQ40    EVQLVESGAELVKPGASVKLSCKASGYTFRSYDINWVRQRPEQGLEWIGWIFPGDGSTKY 60
          *    ******************************************************

      CDR 2                                    CDR 3
SEQ22    NEKFKGKATLTTDKSSSTAYMQLSRLTSEDSAVYFCARWTVVGPGYFDVWGAGTTVTVSS 120
SEQ42    NEKFKGKATLTTDKSSSTAYMQLSKLTSEDSAVYFCARWTVVGPGYFDVWGAGTTVTVSS 120
SEQ30    NEKFKGKATLTTDKSSSTAYMQLSRLTSEDSAVYFCARWTVVGPGYFDVWGAGTTVTVSS 120
SEQ38    NEKFKGKATLTTDKSSSTAYMQLSKLTSEDSAVYFCARWTVVGPGYFDVWGAGTTVTVSS 120
SEQ29    NEKFKGKATLTTDKSSSTAYMQLSRLTSEDSAVYFCARWTVVGPGYFDVWGAGTTLTVSS 120
SEQ46    NEKFKGKATLTTDKSSSTAYMQLSKLTSEDSAVYFCARWTVVGPGYFDVWGAXTTVTVSS 120
SEQ24    NEKFKGKATLTTDKSSSTAYMQLSRLTSEDSAVYFCARWTVVGPGYFDVWGAGTTVTVSS 120
SEQ34    NEKFKGKATLTTDKSSSTAYMQLSKLTSEDSAVYFCARWTVVGPGYFDVWGAGTFVTVSS 120
SEQ41    NEKFKGKATLTTDKSSSTAYMQLSRLTSEDSAVYFCARWTVVGPGYFDVWGAGTTVTVSS 120
SEQ31    NEKFKGKATLTTDKSSSTAYMQLSKLTSEDSAVYFCARWTVVGPGYFDVWGAGTTVTVSS 120
SEQ26    NEKFKGKATLTTDKSSSTAYMQLSRLTSEDSAVYFCARWTVVGPGYFDVWGAGTTVTVSS 120
SEQ43    NEKFKGKATLTTDKSSSTAYMQLSKLTSEDSAVYFCARWTVVGPGYFDVWGAGTTVTVSS 120
SEQ27    NEKFKGKATLTTDKSSSTAYMQLSRLTSEDSAVYFCARWTVVGPGYFDVWGAGTTVTVSS 120
SEQ28    NEKFKGKATLTTDKSSSTAYMQLSKLTSEDSAVYFCARWTVVGPGYFDVWGAGTTVTVSS 120
SEQ33    NEKFKGKATLTTDKSSSTAYMQLSRLTSEDSAVYFCARWTVVGPGYFDVWGAGTTVTVSS 120
SEQ35    NEKFKGKATLTTDKSSSTAYMQLSKLTSEDSAVYFCARWTVVGPGYFDVWGAGTTVTVSS 120
SEQ45    NEKFKGKATLTTDKSSSTAYMQLSRLTSEDSAVYFCARWTVVGPGYFDVWGAGTTVTVSS 120
SEQ32    NEKFKGKATLTTDKSSSTAYMQLSKLTSEDSAVYFCARWTVVGPGYFDVWGAGTTVTVSS 120
SEQ44    NEKFKGKATLTTDKSSSTAYMQLSRLTSEDSAVYFCARWTVVGPGYFDVWGAGTSVTVSS 120
SEQ23    NEKFKGKATLTTDKSSSTAYMQLSKLTSEDSAVYFCARWTVVGPGYFDVWGAGTTVTVSS 120
SEQ36    NEKFKGKATLTTDKSSSTAYMQLSRLTSEDSAVYFCARWTVVGPGYFDVWGAGTTVTVSS 120
SEQ37    NEKFKGKATLTTDKSSSTAYMQLSRLTSEDSAVYFCARWTVVGPGYFDVWGAGTTVTVSS 120
SEQ25    NEKFKGKATLTTDKSSSTAYMQLSRLTSEDSAVYFCARWTVVGPGYFDVWGAGTTVTVSS 120
SEQ47    NEKFKGKATLTTDKSSSTAYMQLSRLTSEDSAVYFCARWTVVGPGYFDVWGAGTTVTVSS 120
SEQ39    NEKFKGKATLTTDKSSSTAYMQLSRLTSEDSAVYFCARWTVVGPGYFDVWGAGTTVTVSS 120
SEQ40    NEKFKGKATLTTDKSSSTAYMQLSRLTSEDSAVYFCARWTVVGPGYFDVWGAGTSVTVSS 120
         **************************************************** *.:****
```

The line above the ruler is used to mark strongly conserved positions. Three characters ('*', ':' and '.') are used:

'*' indicates positions which have a single, fully conserved residue

':' indicates that one of the following 'strong' groups is fully conserved

'.' indicates that one of the following 'weaker' groups is fully conserved

Group 1

```
                                        CDR 1                CDR 2
SEQ6          DIVLTQSPAIMSASPGEKVTITCSASSSVSYMNWFQQKPGTSPKLWIYSTSNLASGVPAR 60
SEQ10         DIVMTQSPAIMSASPGEKVTITCSASSSVSYMNWFQQKPGTSPKLWIYSTSNLASGVPAR 60
SEQ19         DVLMTQSPAIMSASPGEKVTITCSASSSVSYMNWFQQKPGTSPKLWIYSTSNLASGVPAR 60
SEQ21         DVLMTQSPAIMSASPGEKVTITCSASSSVSYMNWFQQKPGTSPKLWIYSTSNLASGVPAR 60
SEQ18         DILXTQSPAIMSASPGEKVTITCSASSSVSYMNWFQQKPGTSPKLWIYSTSNLASGVPAR 60
SEQ9          DIVMTQSPAIMSASPGEKVTITCSASSSVSYMNWFQQKPGTSPKLWIYSTSNLASGVPAR 60
SEQ20         DIVMTQTPAIMSASPGEKVTITCSASSSVSYMNWFQQKPGTSPKLWIYSTSNLASGVPAR 60
SEQ17         DILMTQSPAIMSASPGEKVTITCSASSSVSYMNWFQQKPGTSPKLWIYSTSNLASGVPAR 60
SEQ11         DIQMTQSPAIMSASPGEKVTITCSASSSVSYMNWFQQKPGTSPKLWIYSTSNLASGVPAC 60
SEQ13         DIQMTQSPAIMSASPGEKVTITCSASSSVSYMNWFQQKPGTSPKLWIYSTSNLASGVPAR 60
SEQ14         DIQMIQSPAIMSASPGEKVTITCSASSSVSYMNWFQQKPGTSPKLWIYSTSNLASGVPAR 60
SEQ12         DIKINQSPAIMSASPGEKVTITCSASSSVSYMNWFQQKPGTSPKLWIYSTSNLASGVPAR 60
SEQ15         DILLTQSPAIMSASPGEKVTITCSASSSVSYMNWFQQKPGTSPKLWIYSTSNLASGVPAR 60
SEQ16         DIQLTQSPAIMSASPGEKVTITCSASSSVSYMNWFQQKPGTSPKLWIYSTSNLASGVPAR 60
SEQ8          DIVLTQSPAIMSASPGEKVTITCSASSSVSYMNWFQQKPGTSPKLWIYSTSNLASGVPAR 60
SEQPrevalent  QIVLTQSPAIMSASPGEKVTITCSASSSVSYMNWFQQKPGTSPKLWIYSTSNLASGVPAR 60
SEQ7          DIELTQSPAIMSASPGEKVTITCSASSSVSYMNWFQQKPGTSPKLWIYSTSNLASGVPAR 60
              ::   *:****************************************************

                                            CDR 3
SEQ6          FSGSGSGTSYSLTISRMEAEDAATYYCQQRSSYPNTFGGGTKLELKR 107
SEQ10         FSGSGSGTSYSLTISRMEAEDAATYYCQQRSSYPNTFGGGTKLELKR 107
SEQ19         FSGSGSGTSYSLTISRMEAEDAATYYCQQRSSYPNTFGGGTKLEIKR 107
SEQ21         FSGSGSGTSYSLTISRMEAEDAATYYCQQRSSYPNTFGGGTKLELKR 107
SEQ18         FSGSGSGTSYSLTISRMEAEDAATYYCQQRSSYPNTFGGGTKLELKR 107
SEQ9          FSGSGSGTSYSLTISRMEAEDAATYYCQQRSSYPNTFGGGTKLEIKR 107
SEQ20         FSGSGSGTSYSLTISRMEAEDAATYYCQQRSSYPNTFGGGTKLEIKR 107
SEQ17         FSGSGSGTSYSLTISRMEAEDAATYYCQQRSSYPNTFGGGTKLEIKR 107
SEQ11         FSGSGSGTSYSLTISRMEAEDAATYYCQQRSSYPNTFGGGTKLEIKR 107
SEQ13         FSGSGSGTSYSLTISRMEAEDAATYYCQQRSSYPNTFGGGTKLEIKR 107
SEQ14         FSGSGSGTSYSLTISRMEAEDAATYYCQQRSSYPNTFGGGTKLEIKR 107
SEQ12         FSGSGSGTSYSLTISRMEAEDAATYYCQQRSSYPNTFGGGTKLEIKR 107
SEQ15         FSGSGSGTSYSLTISRMEAEDAATYYCQQRSSYPNTFGGGTKLEIKR 107
SEQ16         FSGSGSGTSYSLTISRMEAEDAATYYCQQRSSYPNTFGGGTKLEIKR 107
SEQ8          FSGSGSGTSYSLTISRMEAEDAATYYCQQRSSYPNTFGGGTKLEIKR 107
SEQPrevalent  FSGSGSGTSYSLTISRMEAEDAATYYCQQRSSYPNTFGGGTKLEIK- 106
SEQ7          FSGSGSGTSYSLTISRMEAEDAATYYCQQRSSYPNTFGGGTKLEINV 107
              *********************************************::
```

Group 3

```
                                          CDR 1                  CDR 2
VLgroup3      DIVMTQSPKSMSMSVGERVTLTCKASENVVTYVSWYQQKPEQSPKLLIYGASNRYTGVPD 60
VLgroup3      RFTGSGSATDFTLTISSVQAEDLADYHCGQGYSYPYTFGGGTKLEIKR 108
                                                CDR 3
```

The line above the ruler is used to mark strongly conserved positions. Three characters ('*', ':' and '.') are used:

'*' indicates positions which have a single, fully conserved residue

':' indicates that one of the following 'strong' groups is fully conserved

'.' indicates that one of the following 'weaker' groups is fully conserved

FIG. 4a – Grading of Skin GvHD, day 1, 10, 30 and last
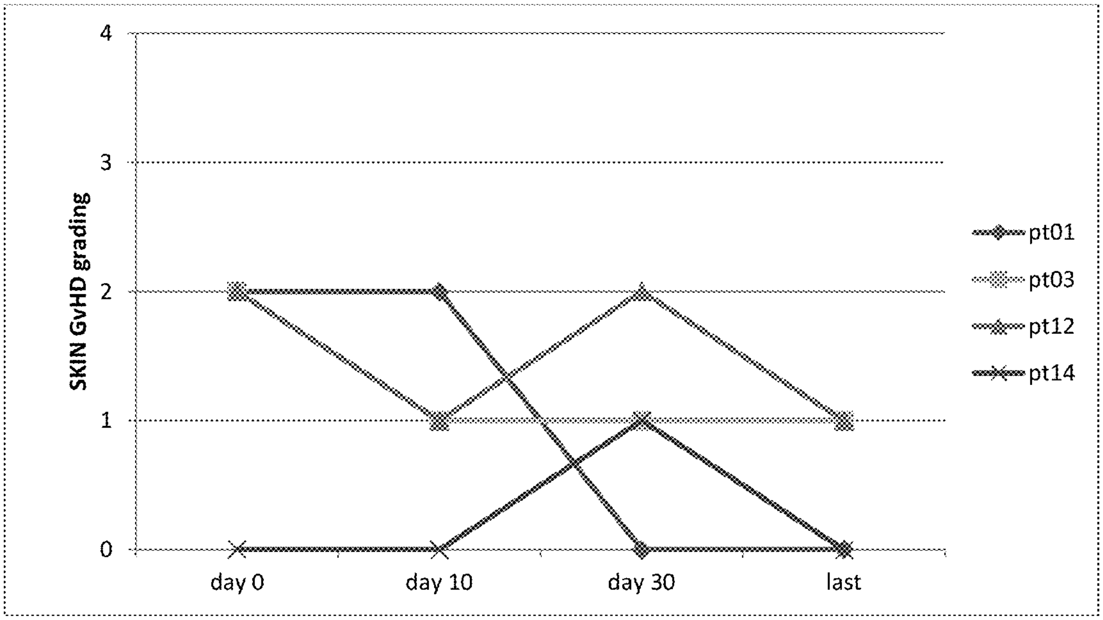
FIG. 4b – Grading of Liver GvHD, day 1, 10, 30 and last
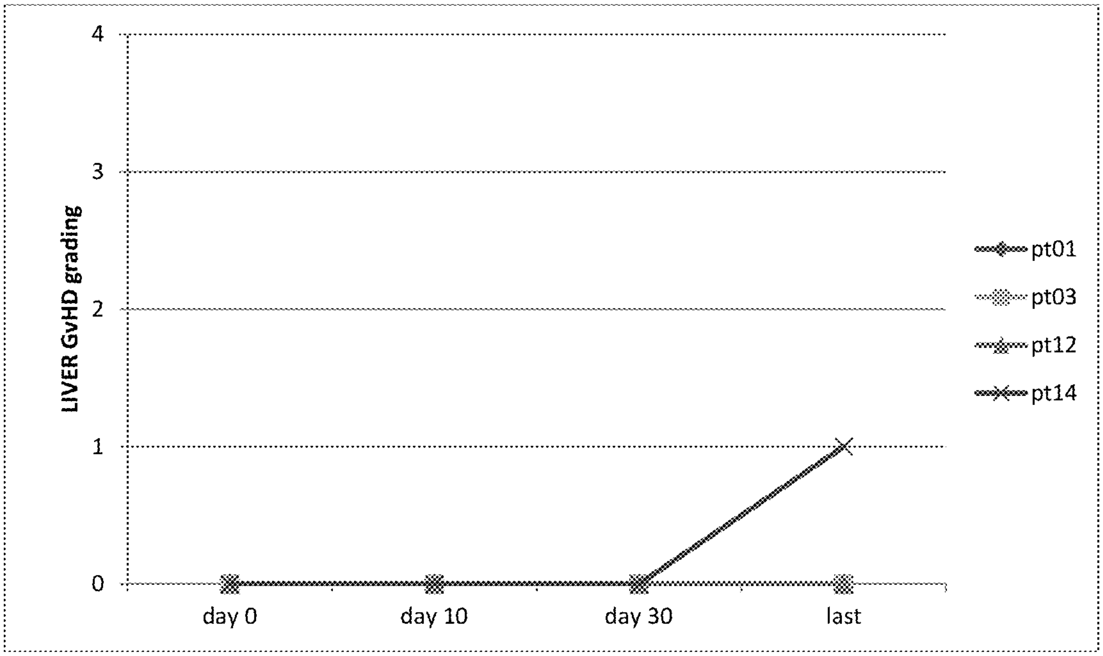

FIG. 4c – Grading of Gut GvHD, day 1, 10, 30 and last
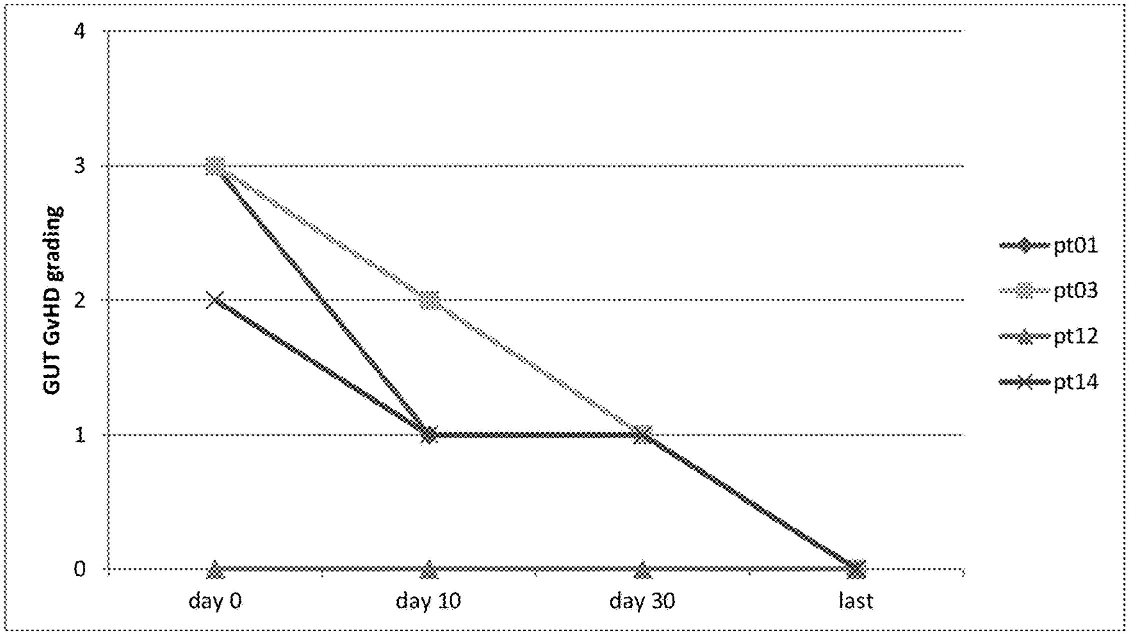
FIG. 5 – Absolute CD4 counts
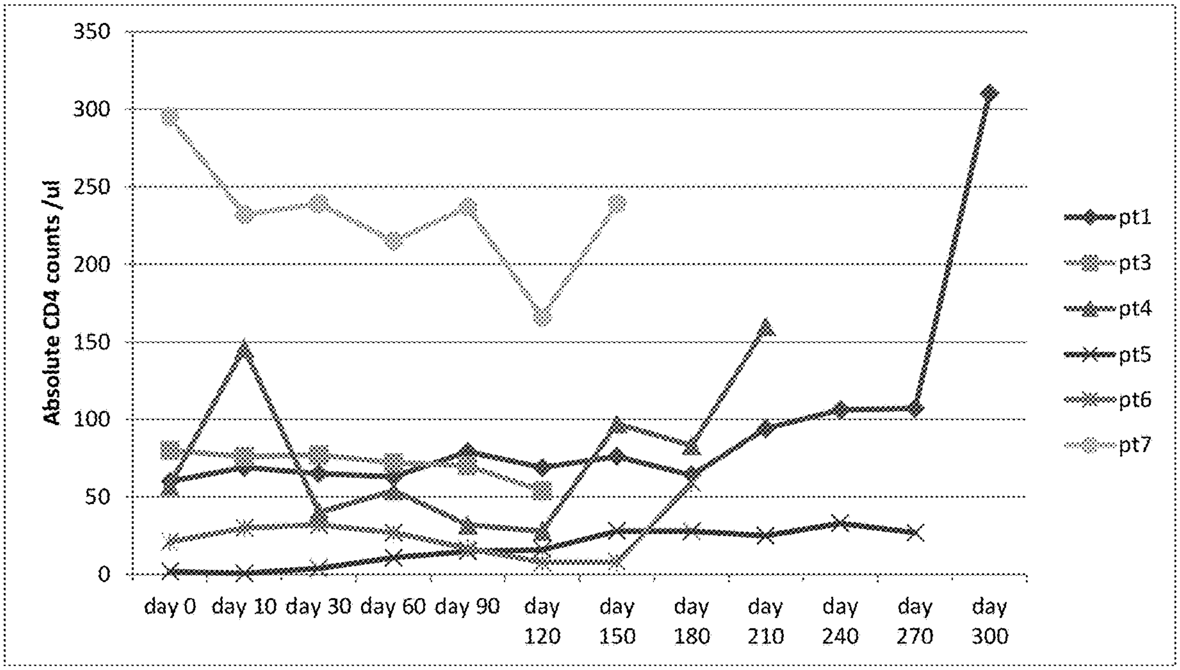

FIG. 8 – Structure of preferred antibodies, according to the present invention. The Figure shows two different groups of light chain that can form an antibody of the present invention (VL group 1 and VL group 3).
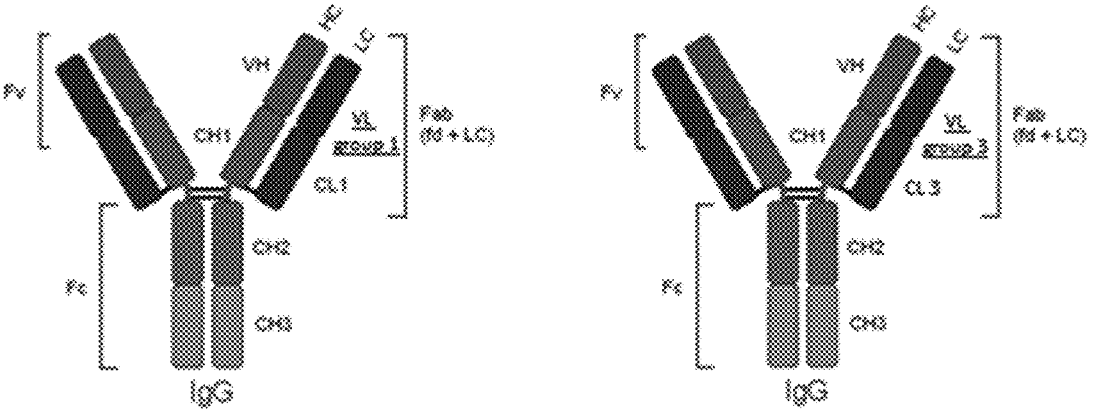
FIG. 9 – Flow cytometry analysis utilized to determine the ability of CDina26 to bind to cell surface expressed CD26.
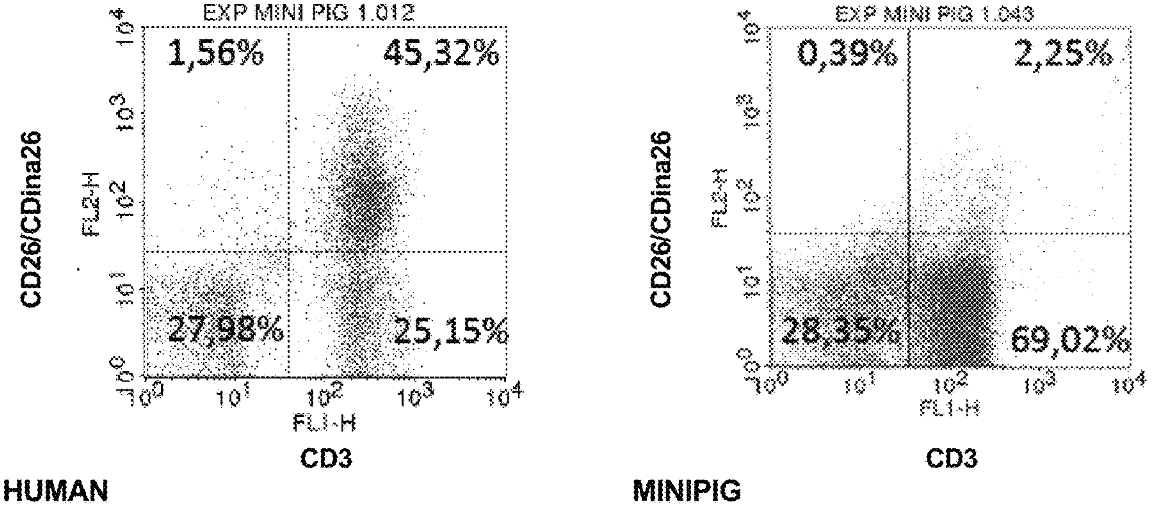

FIG. 10 – CDina26 sequences summary table.

| Type | SEQ N° Amino acidic | SEQ N° Nucleotidic |
|---|---|---|
| CDR-L1 Light group 1 | 129 | |
| CDR-L2 Light group 1 | 130 | |
| CDR-L3 Light group 1 | 2 | |
| CDR-L1 Light group 3 | 131 | |
| CDR-L2 Light group 3 | 132 | |
| CDR-L3 Light group 3 | 3 | |
| CDR-H1 Heavy | 133 | |
| CDR-H2 Heavy | 134 | |
| CDR-H3 Heavy | 1 | |
| VL prevalent (group 1) | 4 | 50 |
| VL group 3 | 5 | 51 |
| VL group 1 | 6 | 52 |
| | 7 | 53 |
| | 8 | 54 |
| | | 55 |
| | 9 | 56 |
| | | 57 |
| | | 58 |
| | | 59 |
| | | 60 |
| | | 61 |
| | | 62 |
| | 10 | 63 |
| | | 64 |
| | | 65 |
| | | 66 |
| | 11 | 67 |
| | 12 | 68 |
| | 13 | 69 |
| | 14 | 70 |
| | 15 | 71 |
| | 16 | 72 |
| | 17 | 73 |
| | 18 | 74 |
| | 19 | 75 |
| | 20 | 76 |
| | 21 | 77 |
| VH group 1 | 22 | 78 |
| | | 79 |
| | | 80 |
| | | 81 |
| | | 82 |
| | 23 | 83 |
| | | 84 |
| | | 85 |
| | | 86 |
| | 24 | 87 |
| | | 88 |
| | | 89 |
| | | 90 |
| | | 91 |

| Type | SEQ N° Amino acidic | SEQ N° Nucleotidic |
|---|---|---|
| ABR1 Light group 1 | 135 | |
| ABR2 Light group 1 | 136 | |
| ABR3 Light group 1 | 137 | |
| ABR1* Light group 3 | 138 | |
| ABR2* Light group 3 | 139 | |
| ABR3* Light group 3 | 140 | |
| ABR1h Heavy group 1 | 141 | |
| ABR2h Heavy group 2 | 142 | |
| ABR3h Heavy group 3 | 143 | |
| VH group 1 | 25 | 92 |
| | | 93 |
| | 26 | 94 |
| | | 95 |
| | | 96 |
| | | 97 |
| | | 98 |
| | 27 | 99 |
| | | 100 |
| | | 101 |
| | 28 | 102 |
| | | 103 |
| | | 104 |
| | 29 | 105 |
| | 30 | 106 |
| | | 107 |
| | 31 | 108 |
| | | 109 |
| | 32 | 110 |
| | | 111 |
| | 33 | 112 |
| | 34 | 113 |
| | 35 | 114 |
| | 36 | 115 |
| | 37 | 116 |
| | 38 | 117 |
| | 39 | 118 |
| | 40 | 119 |
| | 41 | 120 |
| | 42 | 121 |
| | 43 | 122 |
| | 44 | 123 |
| | 45 | 124 |
| | 46 | 125 |
| | 47 | 126 |
| CL | 48 | 127 |
| CH1-CH2-CH3 | 49 | 128 |

FIG. 11 – Binding of human (left) and porcine (right) antigen (Ag) on captured CDina26 Measured in Biacore® Resonance Units (RU).
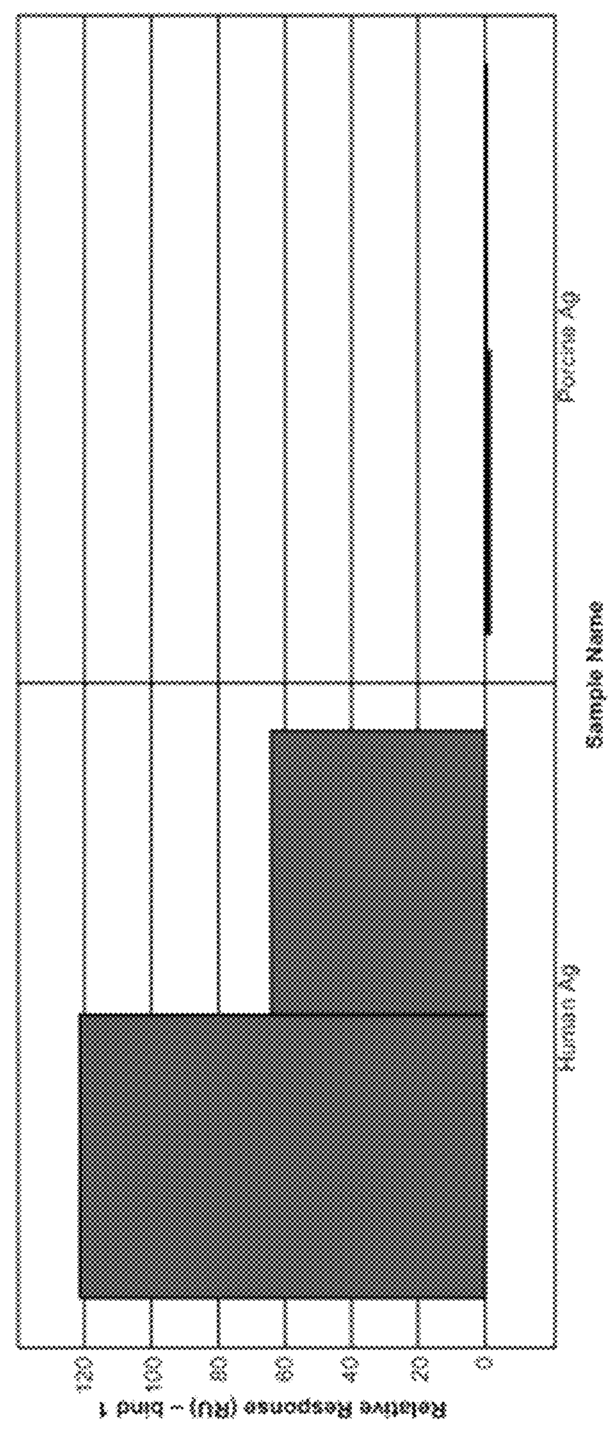

FIG. 12 – Bar plot comparison of CDina26 binding to the 7 identified discontinuous binding regions in CD26.
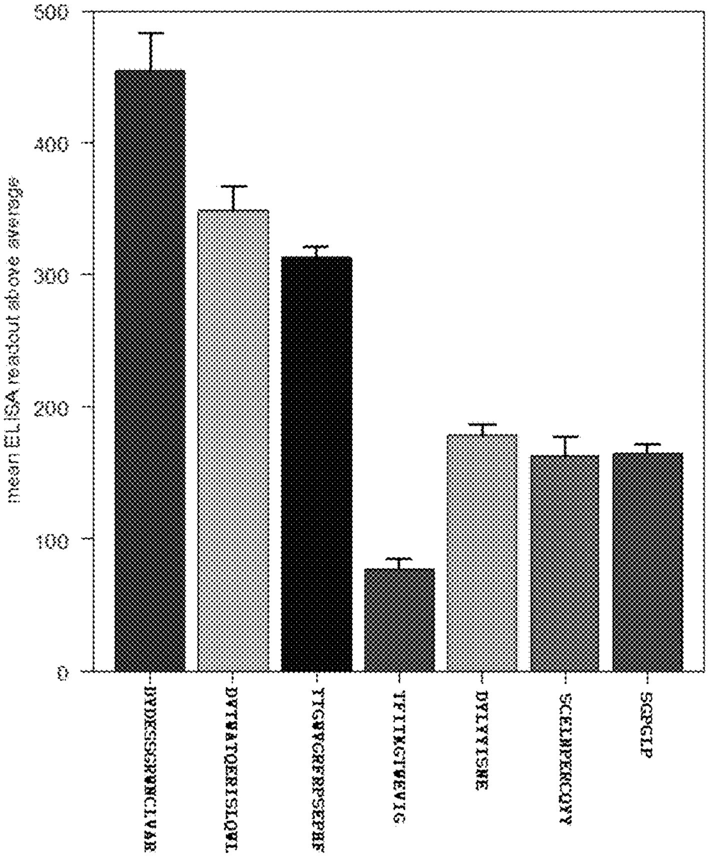

Figure 13A – A view of the amino acids of CD26 involved in epitope binding.
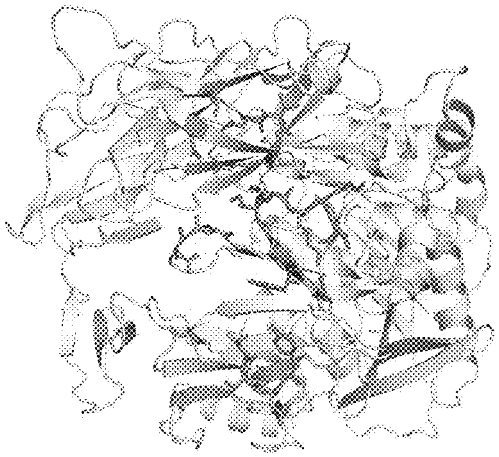
Figure 13B – A rotated view of the binding epitope residues.
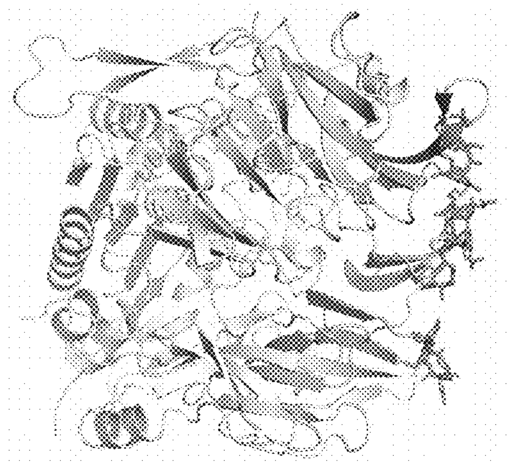
Figure 13C – A CD26 and anti-CD26 antibody Fab complex is shown.
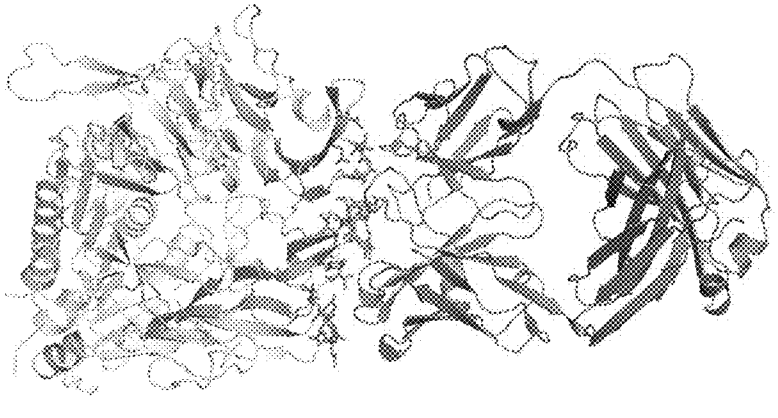

ANTI-CD26 ANTIBODIES

FIELD OF THE INVENTION

The present invention pertains to novel antibodies capable of binding to CD26, as well as to their use as a medicament. Furthermore, the present invention relates to antibodies for use in treating and/or preventing at least one of Graft-versus-Host Disease (GvHD) and Aplastic Anemia, as well as to antibodies for use in promoting engraftment after haematopoietic stem cell transplantation.

BACKGROUND OF THE INVENTION

CD26 is a widely distributed 110 kDa cell surface glycoprotein, initially defined as a T-cell activation antigen (Fox et al. (1984) J. Immunol. 133, 1250-1256, Fleischer (1987) J. Immunol. 138, 1346-1350, and Morimoto et al. (1989) J. Immunol. 143, 3430-3439). This molecule has been shown to have dipeptidyl peptidase IV (DPPIV; EC3.4.14.5) activity in its extracellular domain, and wide tissue distribution (Hegen et al. (1990) J. Immunol. 144, 2908-2914 and Ulmer et al. (1990) J. Immunol. 31, 429-435; WO 2007/014169 A2). CD26 has multiple functions in human T-cell physiology. For instance, evidence suggests that CD26 can deliver a costimulatory signal for T-cell activation (Morimoto et al. (1994) Immunologist 2: 4-7 and Fleischer (1994) Immunol. Today 15:180-184). Further, CD26 has been identified as the ADA binding protein, and the CD26/ADA complex may play a key role in regulating immune system function (Dong et al. (1996) J Immunol. 156(4):1349-55, Kameoka et al. (1993) Science. 261(5120): 466-9, and Morrison et al. (1993) J Exp Med. 177(4):1135-43). A functional association between CD26 and the cellular protein topoisomerase II a has also been reported (Aytac et al. (2003) British Journal of Cancer 88:455-462). Anti-CD26 antibodies are e.g. known from WO 2007/014169 A2.

Haematopoietic stem cell transplantation (HSCT) represents an important therapy for many haematological and numerous epithelial malignancies, as well as for a considerable number of non-malignant diseases (Ferrara et al., 2009, Lancet.; 373: 1550-1561; Sun et al., 2007, Transl. Res.; 150: 197-214). Graft-versus-host disease (GvHD) is a major complication of allogeneic haematopoietic stem cell transplantation (HSCT), and therefore limits the use of these important therapies.

There are two major types of haematopoietic cell transplantation: autologous and allogeneic. Autologous transplantation involves isolation of haematopoietic stem cells (HSC) from a patient, storage of the stem cells, medical treatment of the patient that destroys stem cells remaining in the body, and return of the patient's own stored stem cells to his body. Autologous transplants have the advantage of a lower risk of graft rejection, infection and other correlated diseases. Allogeneic transplantation involves two persons: one is the healthy donor and one is the patient or recipient. Allogeneic HSC donors must have a tissue (HLA human leukocyte antigens) type that matches the recipient and, in addition, the recipient requires immunosuppressive medications. There are three possible sources of haematopoietic stem cells for transplantation: the Bone Marrow (BM), the Peripheral Blood (PB) and the Umbilical Cord Blood (UCB).

The development of novel strategies has helped to expand the indications for allogeneic HSCT over the last several years (Sun et al., 2007, supra). Improvements in infectious prophylaxis, immunosuppressive medications, supportive care and DNA-based tissue typing have also contributed to improved outcomes after allogeneic HSCT (Ferrara et al., 2009, supra). For these reasons, the number of allogeneic haematopoietic cell transplantations continues to increase. However, graft-versus-host disease (GvHD) remains a major complication of allogeneic HSCT.

GvHD occurs when donor T cells identify genetically defined proteins on host cells as not-self and mount an immune response in order to destroy them (Ferrara et al., 2009, supra). Depending on the time at which it occurs after HSCT, GvHD can be either acute or chronic. Acute GvHD (aGvHD) is responsible for 15% to 40% of mortality and is the major cause of morbidity after allogeneic HCT, while chronic GvHD (cGvHD) occurs up to 50% of patients who survive three months after HCT (Sun et al., 2007, Transl. Res.; 150: 197-214).

Acute Graft-versus-Host Disease generally occurs after allogeneic HSCT as reaction of donor immune cells against host tissues. The three main tissues affected by acute GvHD are the skin, liver, and gastrointestinal tract. Clinically, the diagnosis is suspected when a recipient of HSCT develops any or all of the following signs or symptoms: dermatitis (skin rash), cutaneous blisters, crampy abdominal pain with or without diarrhoea, persistent nausea and vomiting, hepatitis (with elevation of bilirubin and/or liver enzymes). Symptoms most frequently start with donor engraftment, before day 100 after the HSCT, but may also occur late. Acute GvHD is a clinical diagnosis confirmed by histological evidences.

Acute GvHD can be staged by the number and extent of organ involvement. The current staging system is derived from Glucksberg first aGvHD classification in 1974 (Glucksberg et al., 1974, Transplantation; 18:4 295-304). Recent data support the use of the grading system, since it is able to subdivide patients into risk categories for complications and mortality. In this system, patients are divided into one of four grades (I-IV) depending on the degree or stage of involvement in three organs. The skin is staged with percent body surface involved, the liver is staged with degree of bilirubin elevation, and the gastrointestinal tract is staged with amount of diarrhoea. Using these criteria, a single grade is assigned to each patient (Jacobsohn et al., 2007, Orphanet J. of Rare Diseases; 2:35).

Various clinical manifestations of GvHD are known. The earliest and most common manifestation is skin GvHD. This is essentially a maculopapular rash that can begin anywhere in the body but often start with palm and sole involvement. The patient may complain of pruritus or tenderness in affected areas. In severe cases, blisters may occur. The gastrointestinal manifestations include diarrhoea, which may become bloody, cramping, nausea, vomiting and failure to thrive. Furthermore, jaundice from hyperbilirubinemia is the hallmark of liver GvHD (Jacobsohn et al., 2007, supra), although a hepatitic variant of GvHD with a rise in liver enzymes like an acute viral hepatitis, has been recognized (Akpek et al., 2002, Blood; 100: 3903-3907). Even if methylprednisolone is not registered in any European Countries for this indication, it is considered current standard of care in first line treatment of acute GvHD.

First line treatment of acute GvHD, with methylprednisolone 2 mg/kg/day is effective in over 50% of patients, but produces durable responses only in ⅓ of the patients. Non responders are offered second line therapy, which is based on combinations of immunosuppressive agents not registered in this indication. Second line therapy is largely unsatisfactory with one year survival of 30% in most large clinical trials. None of these strategies has achieved the level of success required to become standard of care. After 30 years of transplant experience steroid refractory acute GvHD (aGvHD), remains largely an untreatable disease. It has to be emphasized that aGvHD patients resistant to steroid therapy have very limited therapeutic options and that there are no currently authorized treatments for this clinical situation. This condition is life-threatening in particular due to the increased mortality in this patient population, particularly secondary to infection.

Any clinically relevant result in this patient population would be of significant benefit as it would offer a clinically relevant advantage for steroid resistant aGvHD patients.

Moreover, approaches for facilitating engraftment after haematopoietic stem cell transplantation, will be useful. Engraftment is the process in which the transplanted stem cells find their way to the bone marrow spaces in the centre of the large bones of the body. Only then can the transplanted stem cells begin to produce new blood cells. Experts are not completely certain how this process happens but it is generally acknowledged that this is a long process: it takes approximately two to four weeks after the bone marrow is infused for engraftment to occur. Until the blood stem cells engraft, the patient will be at risk of developing an infection. This is because the transplanted patient has been normally subjected to radiation and/or chemotherapy, whose result is the destruction of the white blood cells in the patient's body. While waiting for the engraftment, a transplanted patient could suffer of serious complication due to an infection (caused by bacteria, virus or fungus), which is one of the main cause of transplant related mortality after Bone Marrow Transplantation (BMT). Accordingly, there is a need in the art for an agent able to improve engraftment. Such an agent will be of significant value for BM transplanted patients. If homing and engraftment can be enhanced, the time to recovery of hematopoietic lineages can be reduced resulting in less engraftment failures and better overall survival, especially in UCB transplantation (Broxmeyer, H. E. (2006). Umbilical Cord Blood Stem Cells: Collection, Processing, and Transplantation. Blood Banking and Transfusion Medicine: Basic Principles and Practice. C. D. Hillyer et al., Churchill Livingston, an imprint of Elsevier, Inc.: 823-832; Lewis, 2002, Intern Med J 32(12): 601-9).

Aplastic anemia is a type of anemia, wherein bone marrow fails to produce sufficient amounts of blood cells for replenishing blood cells. In particular, a congenital and an acquired form of aplastic anemia may exist. Acquired aplastic anemia (AA) is a rare bone marrow failure state characterized by marrow hypocellularity and low peripheral blood cell counts [Young N S, Maciejewski J P. The pathophysiology of acquired aplastic anemia. N Eng J Med 1997, 336:1365-1372]. The evidence of an autoimmune pathogenesis is mostly indirect and the characterization of the underlying immune response is incomplete mainly due to technical difficulties resulting from the disease-specific hypocellularity. Acquired Aplastic anemia is thought to be an immunomediated disease, and current standard non transplant therapy is anti-thymocyte globulin (ATG) plus cyclosporin A (CsA). Failures include patients not responding to first line (30%) and patients relapsing after a first response (30%), such that event free survival does not exceed 30-40% (Bacigalupo A., Passweg J., 2009, Hematol Oncol Clin North Am. 23: 159-70).

Untreated aplastic anemia may lead to death, in some cases even within a short period of merely several months. Current treatments of aplastic anemia encompass for example bone marrow transplantation or immunosuppressive drug therapies. Immunosuppressive drug therapies fail however in a significant number of cases and bone marrow transplantation is not possible in absence of an appropriate donor. Thus, there is also a need in the art to provide alternative agent(s) for treating aplastic anemia, which preferably may be effective for treating patients which are non-responsive to at least one other therapy.

BRIEF DESCRIPTION OF THE INVENTION

The present invention is concerned with the provision of an agent which can be used for treating and/or preventing disease(s), disorder(s) and condition(s), in particular immune-system related disease(s), disorder(s) and condition(s). In particular, the present inventors aimed at the provision of an agent which may be used for treating and/or preventing at least one of Graft-versus-Host disease (GvHD) and Aplastic Anemia or which may be used for promoting engraftment after haematopoietic stem cell transplantation. Preferably, this agent should be moreover essentially well tolerated by patients. In particular, the present inventors aimed at the provision of an agent which prevents and/or treats at least one of GvHD and Aplastic Anemia or promotes engraftment, in patients, in particular in one or more groups of patients, which are non-responsive to another treatment, in particular to another treatment with an immunosuppressive agent, for example a treatment with a steroid, or show an insufficient response thereto.

As a solution to these problems, the present inventors provide inter alia an antibody, a pharmaceutical composition, an isolated nucleic acid molecule, a vector, a composition comprising an antibody mixture, a recombinant host cell, a kit of parts and a process for manufacturing an antibody.

According to a first aspect, an antibody is provided, which antibody can specifically bind CD26, in particular human CD26, said antibody can comprise a heavy chain variable region and a light chain variable region, wherein said heavy chain variable region can comprise the sequence VVIVVGPGYFDV (SEQ ID NO: 1), and/or wherein said light chain variable region can comprise the sequence QQRSSYPNT (SEQ ID NO: 2) and/or the sequence GQGYSYPYT (SEQ ID NO: 3). Furthermore, an antibody of the present invention can have a light chain variable region, which light chain variable region comprises an amino acid sequence selected from the group consisting of SEQ ID NOs: 4, 5, 6 to 21, a variant of the amino acid sequence of SEQ ID NO: 4, and a variant of the amino acid sequence of SEQ ID NO: 5. Moreover, an antibody of the present invention specifically binds CD26 and can have a heavy chain variable region, which heavy chain variable region comprises an amino acid sequence selected from the group consisting of SEQ ID NOs: 22 to 47 and variant(s) thereof. In a particular embodiment, an antibody of the present invention specifically binds CD26 and can have a heavy chain variable region comprising the amino acid sequence of SEQ ID NO: 26 and a light chain variable region comprising the amino acid sequence of SEQ ID NO: 4 or SEQ ID NO:5.

According to another aspect, the present inventors provide an isolated nucleic acid molecule comprising (a) a nucleotide sequence encoding an antibody of the present invention; or (b) a nucleotide sequence complementary to (a). According to still another aspect, an isolated nucleic acid molecule is provided, which comprises a nucleotide sequence selected from the group consisting of SEQ ID NOs: 50 to 128 and a variant thereof, said variant having at least 90% sequence identity to the nucleotide sequence selected from the group consisting of SEQ ID NOs: 50 to 128. According to yet another aspect, the present inventors provide an expression vector comprising a nucleic acid molecule of the present invention, wherein said nucleic acid molecule is operatively linked to an expression control sequence. According to still another aspect, a recombinant host cell is provided, which comprises a nucleic acid molecule of the present invention.

According to yet another aspect, an antibody is provided, which is produced from the hybridoma cell line deposited on the 11 Sep. 2012 under the Budapest Treaty at the Centro di Biotecnologie Avanzate (CBA)—Interlab Cell Line Collection (ICLC) of Genoa (L.go R. Benzi, 10, Genoa, Italy) as PD 12002 or a derivative of said hybridoma cell line. The hybridoma cell line material deposited is also referred to herein shortly as PD 12002 hybridoma deposit. All restrictions as to the availability of these deposits will be withdrawn upon first publication of this application or another application which claims benefit of priority to this application. According to still another aspect, the present inventors provide an antibody that binds the epitope bound by an antibody produced by the hybridoma cell line deposited at CBA-ICLC of Genoa (Italy) as PD 12002.

According to yet another aspect, a process of manufacturing an antibody of the present invention is provided.

According to still another aspect, the present inventors provide a pharmaceutical composition comprising at least one antibody of the present invention and optionally at least one pharmaceutically acceptable excipient. According to yet another aspect, a pharmaceutical composition of the present invention for use as a medicament is provided. According to still another aspect, the present inventors provide a pharmaceutical composition of the present invention for use in promoting engraftment after haematopoietic stem cell transplantation, and/or for use in preventing and/or treating Graft-versus-Host disease (GvHD), in particular after haematopoietic stem cell transplantation, and/or for use in preventing and/or treating Aplastic Anemia.

According to yet another aspect, an antibody or an antibody mixture of the present invention, in particular a composition comprising an antibody mixture of the present invention, for use as a medicament is provided. According to still another aspect, the present inventors provide the antibody of the present invention or the antibody mixture, in particular the composition comprising an antibody mixture, for use in promoting engraftment after haematopoietic stem cell transplantation, and/or for use in preventing and/or treating Graft-versus-Host disease (GvHD), preferably after haematopoietic stem cell transplantation, and/or for use in preventing and/or treating Aplastic Anemia, preferably Severe Aplastic Anemia. According to yet another aspect, a kit of parts is provided, which comprises: (i) at least one antibody of the present invention, in particular a composition comprising an antibody mixture of the present invention, and additionally (ii) a) at least one immunosuppressive drug or b) at least one corticosteroid and/or at least one antihistamine.

DESCRIPTION OF THE FIGURES

FIG. 1*a* shows full CD26 human sequence.

FIG. 1*b* shows full CD26 porcine sequence.

FIG. 1*c* shows aligned full CD26 human and porcine sequence.

FIG. 2*a* shows CDR3 sequences, which can be present in an antibody according to the present invention.

FIG. 2*b* shows the list of sequences of the VH CDR1, VH CDR2, VH CDR3, VL CDR1, VL CDR2, and VL CDR3 of CD26 specific antibodies.

FIG. 2*c* shows the list of sequences of the VH ABR1, VH ABR2, VH ABR3, VL ABR1, VL ABR2, and VL ABR3 of CD26 specific antibodies.

FIGS. 3*a* and 3*b* show the sequence similarity seen in the various VH and VL regions, which can be present in an antibody according to the present invention. The VH sequences within VH group1, and the VL sequences within VL group 1 comprise identical CDRs.

FIG. 4*a* shows a diagram illustrating Grading of Skin GvHD of patients enrolled in a study concerned with the administration of CDina26.

FIG. 4*b* shows a diagram illustrating Grading of liver GvHD of patients enrolled in a study concerned with the administration of CDina26.

FIG. 4*c* shows a diagram illustrating Grading of gut GvHD of patients enrolled in a study concerned with the administration of CDina26.

FIG. 5 shows a diagram illustrating absolute CD4 counts.

FIG. 8 illustrates the structure of preferred antibodies according to the present invention. The Figure shows two different groups of light chain that can form an antibody of the present invention (VL group 1 and VL group 3).

FIG. 9 illustrates Flow cytometry analysis utilized to determine the ability of CDina26 to bind to cell surface expressed CD26.

FIG. 10 Summary of SEQ ID NOs. Each one of the VL amino acid sequences can be present in combination with one of the VH amino acid sequences in an antibody of the present invention, optionally further in combination with the CL amino acid sequence having SEQ ID NO:48 and a CH1-CH2-CH3 sequence having SEQ ID NO:49. FIG. 10 also indicates nucleotide sequences having SEQ ID NO:s 50 to 128, corresponding to amino acid sequences having SEQ ID NO:s 4 to 49.

FIG. 11 shows binding of Human (left) and Porcine (right) Antigen (Ag) on captured CDina26, measured in Biacore® Resonance Units (RU).

FIG. 12 shows a bar plot comparison of CDina26 binding to the 7 identified discontinuous binding regions in CD26: DYDESSGRWNCLVAR (SEQ ID NO: 146); DVTWATQERISLQWL (SEQ ID NO: 147); TTGWVGRFRPSEPHF (SEQ ID NO: 153); TFITKGTWEVIG (SEQ ID NO: 155); DYLYYISNE (SEQ ID NO: 156); SCELNPERCQYY (SEQ ID NO: 157); and SGPGLP (SEQ ID NO: 158).

FIG. 13A-13C shows an illustration of the CD26 epitope binding. FIGS. 13A and 13B show alternate viewing angles of CD26 residues involved in epitope binding for an anti-CD26 monoclonal antibody. FIG. 13C shows a CD26/anti-CD26 monoclonal antibody Fab binding complex.

DETAILED DESCRIPTION OF THE INVENTION

Figure 6:
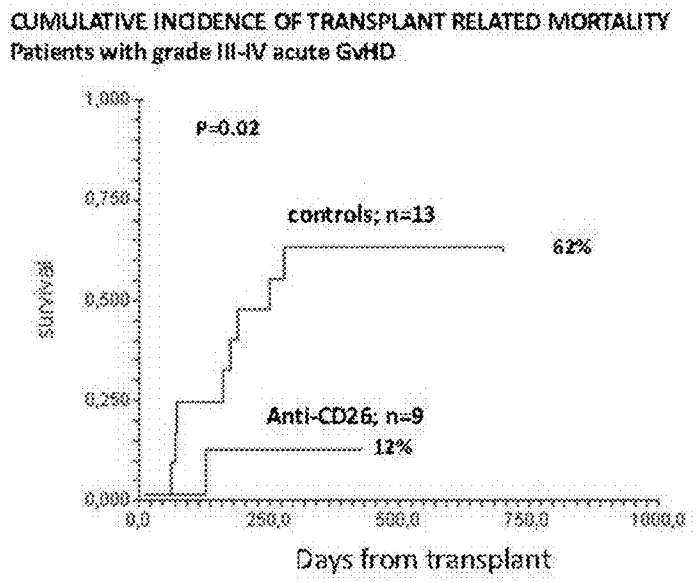
FIG. 6 shows a diagram illustrating the projected cumulative incidence of transplant related mortality of 13 control patients with grade III-IV acute GvHD, treated with steroids, cyclosporine and other immunosuppressive drugs, compared with 9 patients treated with steroids, cyclosporine and CDina26.

During numerous experiments leading to the present invention, the inventors surprisingly found an antibody which can be used with highly beneficial and promising results as a medicament, in particular for treating and/or preventing at least one of Graft-versus-Host Disease (GvHD) and Aplastic Anemia, as well as for promoting engraftment after haematopoietic stem cell transplantation. The antibody of the present invention can exhibit specific binding to CD26, in particular to human CD26, especially human CD26 present on a stem cell or expressed on an activated T lymphocyte. Binding of an antibody of the present invention to human CD26 expressed on activated T lymphocytes (in particular subpopulations of CD16+ CD3+ T and CD56+ CD3+ T) is a particularly advantageous property of an antibody of the present invention, as discussed below. The rationale for the use of murine monoclonal antibody against CD26 for treating aGvHD steroid resistant is mainly supported by its ability to block CD26 activity. Experiments performed by the present inventors show that CD26 is over-expressed in stimulated T cells and over-expressed in lower amount in stimulated Natural Killer cells. On the contrary, this molecule is low expressed on resting cells. B cells, monocytes and dendritic cells never express CD26, neither do mesenchymal stem cells, endothelial cells and fibroblasts express CD26. An anti-CD26 of the present invention specifically binds to activated regulatory T cells, interfering with their expansion and with their role in the modulation of the immune response. While not wishing to be bound by any theory, it is currently assumed that activated lymphocytes are a target of anti-CD26 and that a partial depletion of activated lymphocytes could lead to a clinically relevant modulation of at least one of GvHD, in particular aGvHD, especially steroid resistant aGvHD, of Aplastic Anemia, and of disease(s), disorder(s) and/or condition(s) present before and/or during and/or after haematopoietic stem cell transplantation, as well as could promote engraftment after haematopoietic stem cell transplantation. While not wishing to be bound by any theory, it is currently assumed that donor T lymphocytes can still mount a reaction directly against tumour cells.

Haematopoietic stem cell transplantation (HCT) represents a standard treatment for hematologic diseases and malignancies.

While not wishing to be bound by any theory, it is currently assumed that inhibition or depletion of CD26 on donor cells by administering one or more antibodies of the present invention, in particular CDina26, can enhance engraftment, in particular short-term engraftment, as well as can enhance repopulation, in particular competitive repopulation, secondary transplantation and survival of the treated subject, for example humans and mice. Furthermore, while not wishing to be bound by any theory, it is currently assumed that if homing and engraftment is enhanced, in particular by administering at least one antibody of the present invention, especially CDina26, the time to recovery of haematopoietic lineages can be reduced resulting in less engraftment failure and better overall survival, especially in hUCB (human umbilical cord blood cell) transplantation.

An antibody of the present invention for use as a medicament or a therapy using this antibody can provide more patients with best chances of a successful outcome after haematopoietic cell transplantation. Furthermore, one or more antibodies of the present invention against CD26 antigen, in particular, CDina26, can give important clinical benefit in patients who have undergone haematopoietic stem cell transplantation for at least one of treating steroid resistant acute GvHD and improving the engraftment that is correlated, directly, with overall survival.

While not wishing to be bound by any theory, it is currently assumed that administering at least one antibody of the present invention, in particular CDina26, can provide a beneficial activity, in particular promoting engraftment after haematopoietic stem cell transplantation and/or preventing and/or treating at least one of Graft-versus-Host Disease and Aplastic Anemia, through the binding to CD26 as membrane glycoprotein that mediates signaling pathway.

Surprisingly, the present inventors provide one or more antibodies, in particular CDina26, solving the before-mentioned problems.

According to one aspect, the present invention provides an antibody, which antibody can specifically bind to CD26 glycoprotein. In particular, this antibody can specifically bind to human CD26, especially to human CD26 present on stem cell(s) (in particular human stem cell(s)) and/or to human CD26 expressed on T lymphocytes (in particular subpopulations of CD16+ CD3+ T and CD56+ CD3+ T), especially on activated T lymphocyte(s) (in particular subpopulations of CD16+ CD3+ T and CD56+ CD3+ T). Unless explicitly indicated otherwise, the terms CD26 and CD26 glycoprotein are used interchangeably herein.

This antibody can comprise a heavy chain variable region and a light chain variable region. The heavy chain variable region of this antibody can comprise the sequence set forth in SEQ ID NO: 1. The light chain variable region of this antibody can comprise the sequence set forth in SEQ ID NO: 2 or the sequence set forth in SEQ ID NO: 3 or both the sequence set forth in SEQ ID NO: 2 and the sequence set forth in SEQ ID NO: 3. The heavy chain variable region can comprise a CDR3 comprising the sequence set forth in SEQ ID NO: 1. The light chain variable region can comprise a CDR3 comprising the sequence set forth in SEQ ID NO: 3 or the sequence set forth in SEQ ID NO: 2 or both the sequence set forth in SEQ ID NO: 2 and the sequence set forth in SEQ ID NO: 3. The heavy chain variable region comprising the sequence set forth in SEQ ID NO: 1, in particular comprising a CDR3 comprising the sequence set forth in SEQ ID NO: 1, can furthermore comprise a CDR1 and a CDR2, wherein the amino acid sequences of the CDR1 of the heavy chain variable region and the CDR2 of the heavy chain variable region are those of a heavy chain variable region of an antibody produced by the hybridoma cell line deposited at CBA-ICLC of Genoa (Italy) as PD 12002, said heavy chain variable region of an antibody produced by the hybridoma cell line deposited at CBA-ICLC as PD 12002 comprising SEQ ID NO: 1, in particular a CDR3 comprising SEQ ID NO: 1. The light chain variable region comprising the sequence set forth in SEQ ID NO: 2, in particular comprising a CDR3 comprising the sequence set forth in SEQ ID NO: 2, can furthermore comprise a CDR1 and a CDR2, wherein the amino acid sequences of the CDR1 of the light chain variable region and the CDR2 of the light chain variable region are those of a light chain variable region of an antibody produced by the hybridoma cell line deposited at CBA-ICLC as PD 12002, said light chain variable region of an antibody produced by the hybridoma cell line deposited at CBA-ICLC as PD 12002 comprising SEQ ID NO: 2, in particular a CDR3 comprising SEQ ID NO: 2. The light chain variable region comprising the sequence set forth in SEQ ID NO: 3, in particular comprising a CDR3 comprising the sequence set forth in SEQ ID NO: 3, can furthermore comprise a CDR1 and a CDR2, wherein the amino acid sequences of the CDR1 of the light chain variable region and the CDR2 of the light chain variable region are those of a light chain variable region of an antibody produced by the hybridoma cell line deposited at CBA-ICLC as PD 12002, said light chain variable region of an antibody produced by the hybridoma cell line deposited at CBA-ICLC as PD 12002 comprising SEQ ID NO: 3, in particular a CDR3 comprising SEQ ID NO: 3. In particular, the CDR1 and CDR2 of the light chain variable region can be those of a light chain variable region of an antibody produced by the hybridoma cell line deposited at CBA-ICLC as PD 12002 and the CDR1 and CDR2 of the heavy chain variable region can be those of a heavy chain variable region of said antibody produced by said hybridoma cell line deposited at CBA-ICLC as PD 12002.

Additionally or alternatively, an antibody, which can specifically bind to CD26, can comprise a heavy chain variable region comprising a CDR3 (SEQ ID NO: 1) and a light chain variable region comprising a CDR3 (SEQ ID NO: 2 and/or 3), wherein the amino acid sequence of the CDR3 of the heavy chain variable region is that of a heavy chain variable region of an antibody produced by the hybridoma cell line deposited at CBA-ICLC of Genoa (Italy) as PD 12002, and the amino acid sequence of the CDR3 of the light chain variable region is that of a light chain variable region of an antibody produced by the hybridoma cell line deposited as PD 12002. In particular, the antibody, which can specifically bind to CD26, can comprise a heavy chain comprising this heavy chain variable region and a light chain comprising this light chain variable region. CDR3 sequences abovementioned are listed in FIG. 2*a*.

Additionally or alternatively, an antibody, which can specifically bind to CD26, can comprise a heavy chain variable region comprising a CDR1, a CDR2, and a CDR3 and a light chain variable region comprising a CDR1, a CDR2, and a CDR3, wherein the amino acid sequences of the CDR1, CDR2, and CDR3 of the heavy chain variable region are those of a heavy chain variable region of an antibody produced by the hybridoma cell line deposited at CBA-ICLC of Genoa (Italy) as PD 12002, and the amino acid sequences of the CDR1, CDR2, and CDR3 of the light chain variable region are those of a light chain variable region of an antibody produced by the hybridoma cell line deposited as PD 12002. In particular, this antibody which can specifically bind to CD26, can comprise a heavy chain comprising this heavy chain variable region and a light chain comprising this light chain variable region. CDR1, CDR2 and CDR3 sequences abovementioned are listed in FIG. 2*b*.

Additionally or alternatively, the antibody, which can specifically bind to CD26, can comprise a heavy chain variable region and a light chain variable region, wherein the amino acid sequences of the heavy chain variable region are those of a heavy chain variable region of an antibody produced by the hybridoma cell line deposited at CBA-ICLC of Genoa (Italy) as PD 12002, and the amino acid sequences of the light chain variable region are those of a light chain variable region of this antibody produced by the hybridoma cell line deposited as PD 12002. In particular, the antibody, which can specifically bind to CD26, can comprise a heavy chain comprising this heavy chain variable region and a light chain comprising this light chain variable region. In particular, the amino acid sequences of the heavy chain can be those of a heavy chain of an antibody produced by the hybridoma cell line deposited as PD 12002, and/or the amino acid sequences of the light chain can be those of a light chain of this antibody produced by the hybridoma cell line deposited as PD 12002. In particular, the antibody, which can specifically bind to CD26, can comprise the same heavy chain sequences and the same light chain sequences as an antibody produced by the hybridoma cell line deposited as PD 12002.

Additionally or alternatively, the antibody, which can specifically bind to CD26, can comprise a heavy chain variable region and a light chain variable region, wherein the amino acid sequences of the heavy chain variable region are those of a heavy chain variable region of an antibody produced by the hybridoma cell line deposited at CBA-ICLC of Genoa (Italy) as PD 12002, and the amino acid sequences of the light chain variable region are those of a light chain variable region of an antibody produced by the hybridoma cell line deposited as PD 12002. In a specific embodiment, an antibody of the present invention can comprise a heavy chain variable region comprising sequence ID NO: 26 and a light chain variable region comprising sequence ID NO: 4 and/or sequence ID NO: 5. In particular, the antibody, which can specifically bind to CD26, can comprise a heavy chain comprising this heavy chain variable region and a light chain comprising this light chain variable region. In particular, the amino acid sequences of the heavy chain are those of a heavy chain of an antibody produced by the hybridoma cell line deposited as PD 12002, and/or the amino acid sequences of the light chain are those of a light chain of an antibody produced by the hybridoma cell line deposited as PD 12002.

According to a preferred embodiment, the antibody of the present invention can bind to the region of amino acid positions 290-550 of the human CD26 sequence, referring to the human CD26 sequence as published in the prior art.

According to a further embodiment, the antibody of the present invention does not specifically bind to porcine CD26. According to one embodiment, the epitope of an anti-human CD26 antibody of the present invention comprises at least one, for example, one, two, three, four, five, or more of the 358 amino acid residues resulting from the difference between human and porcine CD26. Thus, according to this embodiment of the invention, the antibody therefore recognizes such different region between human and porcine CD26.

According to one embodiment of the present invention, the antibody mixture of the present invention does not comprise an antibody not specifically binding to human CD26.

Additionally or alternatively, an antibody, which can specifically bind to CD26, can comprise a heavy chain variable region comprising an ABR1, an ABR2, and an ABR3 and a light chain variable region comprising an ABR1, an ABR2, and an ABR3, wherein the amino acid sequences of the ABR1, ABR2, and ABR3 of the heavy chain variable region are those of a heavy chain variable region of an antibody produced by the hybridoma cell line deposited at CBA-ICLC of Genoa (Italy) as PD 12002, and the amino acid sequences of the ABR1, ABR2, and ABR3 of the light chain variable region are those of a light chain variable region of an antibody produced by the hybridoma cell line deposited as PD 12002. ABR1, ABR2 and ABR3 sequences abovementioned are listed in FIG. 2*c*.

According to one embodiment of the present invention, the following Antigen Binding Regions (ABRs) are present in the antibody of the present invention:

ABR1 (light chain) comprises the amino acid sequence: SSVSYMN (SEQ ID NO: 135), ABR2 (light chain) comprises the amino acid sequence: LWIYSTSNLAS (SEQ ID NO: 136), ABR3 (light chain) comprises the amino acid sequence: QQRSSYPN (SEQ ID NO: 137), wherein preferably ABR3 is included in SEQ ID NO:2, or ABR1 (light chain) comprises the amino acid sequence: ENVVTYVS (ABR1*) (SEQ ID NO: 138), ABR2 (light chain) comprises the amino acid sequence: LLIYGASNRYT (ABR2*) (SEQ ID NO: 139), ABR3 (light chain) comprises the amino acid sequence: GQGYSYPY (ABR3*) (SEQ ID NO: 140), wherein preferably ABR3 is included in SEQ ID NO:3.

According to a further embodiment of the present invention, the sequences ABR1 to 3 or ABR1* to 3* are present in an antibody of the invention together with the following Antigen Binding Regions (ABRs):

ABR1 (heavy chain) comprising the amino acid sequence: YTFRSYDIN (ABR1h) (SEQ ID NO: 141), ABR2 (heavy chain) comprising the amino acid sequence: WIGWIFPGDGSTKY (ABR2h) (SEQ ID NO: 142), ABR3 (heavy chain) comprising the amino acid sequence: RWTVVGPGYFDV (ABR3h) (SEQ ID NO: 143), wherein preferably ABR3 (heavy chain) is included in SEQ ID NO:1.

According to one embodiment, the ABRs are determined according to the "Paratome tool" as published in Kunik V, Peters B, Ofran Y (2012) "Structural Consensus among Antibodies Defines the Antigen Binding Site", PLoS Comput Biol 8(2): e1002388.doi:10.1371/journal.pcbi.1002388; Editor: Brian Baker, University of Notre Dame, United States of America; Published Feb. 23, 2012; see also http://ofranservices.biu.acilisiteiservicesiparatome/index.html. $V_H/V_L$ ABR sequences abovementioned are listed in FIG. 2*b*.

The term "antibody" as used in the context of the present application can encompass whole antibody molecules, full-length immunoglobulin molecules, in particular naturally occurring full-length immunoglobulin molecules or full-length immunoglobulin molecules formed by immunoglobulin gene fragment recombinatorial processes, as well as antibody fragments. Antibody fragments can be in particular antibody fragments comprising at least one antibody-antigen binding site. Antibody fragments can in particular exhibit specific binding to CD26, in particular human CD26, which can be for example present on a stem cell (in particular human stem cell) and/or expressed on T lymphocyte(s) (in particular subpopulations of CD16+ CD3+ T and CD56+ CD3+ T), in particular on activated T lymphocyte(s). Furthermore, the term "antibody" as used in the context of the present application can encompass fusion proteins, in particular exhibiting specific binding to CD26, especially human CD26, which can be present on a stem cell and/or expressed on T lymphocyte(s), in particular on activated T lymphocyte(s). An antibody-antigen binding site can be in particular an antigen binding site of an antibody comprising at least one CDR sequence.

The term "antibody" can include e.g. monoclonal, polyclonal, multispecific (for example bispecific), recombinant, human, chimeric and humanized antibodies. Furthermore, the term "antibody" can also encompass recombinantly expressed antigen binding proteins and antigen binding synthetic peptides. In particular, the term "antibody" can e.g. encompass minibodies, and diabodies, all of which preferably can exhibit specific binding to CD26, especially human CD26. Furthermore, the term "antibody", as used herein, can encompass immunoglobulins produced in vivo, as well as those produced in vitro, in particular by a hybridoma. Moreover, the terms "antibody" or "at least one antibody" can encompass antibody mixtures. The term "antibody mixture" in particular encompasses a mixture comprising or consisting of two or more antibodies exhibiting specific binding to CD26, especially human CD26, in particular comprising at least one antibody of the present invention. The two or more antibodies present in the mixture can be two or more different antibodies, for example two or more antibodies which do not have identical amino acid sequences. In particular, an antibody different from another antibody can be an antibody having an amino acid sequence, wherein at least one amino acid residue has been deleted, inserted or replaced with a different amino acid residue, compared to the amino acid sequence of said another antibody. A particularly useful antibody mixture according to the invention comprises or consists of the antibodies produced by the hybridoma cell line deposited as PD 12002, or comprises at least one of the antibodies produced by the hybridoma cell line deposited as PD 12002.

An antibody according to present invention can be a recombinantly produced antibody. An antibody of the present invention can be a monoclonal and/or murine antibody, in particular a murine monoclonal antibody. As mentioned above, at least one antibody of the present invention can be an antibody mixture comprising at least one antibody of the present invention, in particular comprising or consisting of the antibodies produced by the PD 12002 hybridoma deposit, CDina26.

The term "monoclonal antibody" refers to a substantially homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g. murine) sequences. Typically, humanized antibodies are human immunoglobulins in which residues from the complementary determining region (CDR) are replaced by residues from the CDR of a non-human species (e.g. mouse, rat, rabbit, and hamster) that have the desired specificity, affinity, and capability (Jones et al., 1986, Nature, 321:522-525; Riechmann et al., 1988, Nature, 332:323-327; Verhoeyen et al., 1988, Science, 239: 1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of 60 mammals (e.g. mouse, rat, rabbit, etc.) with the desired specificity, affinity, and capability while the constant regions are homologous to the sequences in antibodies derived from another (usually human) to avoid eliciting an immune response in these species. Typically chimeric antibodies utilize rodent variable regions (VH and VL) and human constant regions, in order to produce an antibody with predominantly human domains. The production of such chimeric antibodies is well known in the art, and may be achieved by standard means. Sequences of human constant regions will be apparent to the skilled person and/or are available in public databases (e.g. National center for Biotechnology Information (NCBI), U.S. National Library of Medicine).

The term "antibody fragment" can refer to a fragment, such as $F(ab')_2$, Fab, $F(ab)_2$, Fab', Fv, dAb, scFv, heavy chain variable region CDR1, heavy chain variable region CDR2, heavy chain variable region CDR3, light chain variable region CDR1, light chain variable region CDR2, light chain variable region CDR3, single chain variable fragment (scFv), VH, VL, and the like, all of which preferably can exhibit specific binding to CD26, especially human CD26. An "antibody fragment" can specifically bind with the same antigen that is recognized by the whole antibody or full-length antibody. An "antibody fragment" can be in particular a portion of an intact antibody.

Antibody fragments which recognize specific epitopes, in particular which specifically bind to CD26, can be generated by a skilled person applying techniques known in the art. Fragments of an antibody, in particular fragments of an antibody, which can specifically bind to CD26, especially human CD26, such as e.g. fragments of one or more anti-CD26 antibodies produced by the PD 12002 hybridoma deposit, CDina26, can be e.g. prepared by enzymatically treating the antibody to obtain antibody fragments. Furthermore, an antibody fragment can be produced by expression of DNA coding for the fragment in a host, such as e.g. *E. coli, B. subtilis, P. pastoris, K. lactis*. An antibody fragment can be e.g. prepared by proteolytic hydrolysis of a full length antibody. Enzymes, in particular proteolytic enzymes, for obtaining antibody fragments are known to a skilled person and include, but are not limited to, e.g. papain, pepsin and/or plasmin. In particular, an antibody fragment can be e.g. prepared by pepsin or papain digestion of full length antibodies by applying procedures known to a skilled person, as mentioned e.g. in US 2010/0196266 A1. Such procedures are described, for example, in Goldenberg, U.S. Pat. Nos. 4,036,945 and 4,331,647, as well as in the references cited therein. Procedures for preparing antibody fragments are known in the art and are described e.g. in Nisonoff et al., Arch Biochem. Biophys. 89: 230 (1960); Porter, Biochem. J. 73: 119 (1959), Edelman, METHODS IN ENZYMOLOGY VOL. 1, page 422 (Academic Press 1967), and Coligan et al., CURRENT PROTOCOLS IN IMMUNOLOGY, VOL. 1, (John Wiley & Sons 1991), p. 2.8.1-2.8.10 and 2.10.-2.10.4.

As used herein, the term "heavy chain" includes a full-length heavy chain and fragments thereof, which are preferably capable of specifically binding to CD26, especially human CD26. A full-length heavy chain can include a heavy chain variable region, VH, and three regions, CH1, CH2, and CH3.

As used herein, the term "light chain" can in particular refer to a full-length light chain and fragments thereof, which preferably are capable of specifically binding to CD26, especially human CD26. A full-length light chain can comprise a light chain variable region, VL, and a light chain constant region, CL.

As used herein, the term "variable region" of an antibody can refer to a variable region of the antibody light chain or to a variable region of the antibody heavy chain or to a combination of the before-mentioned variable regions. The variable regions of the light and heavy chain can each comprise four framework regions (FR) connected by three complementarity determining regions (CDRs). Two definitions of CDR location are currently in use in the art. The first one is the "sequence variability" definition of Kabat et al. ("Sequences of Proteins of Immunological Interest", $4^{th}$ ed., Washington, D.C., Public Health Service, N.I.H., which is incorporated herewith by reference). According to a preferred embodiment, the definition of Kabat et al. is used in the present application. Alternatively, the CDR regions can also be defined using the structural variability definition of Chothia and Lesk (Chothia et al., J. Mol. Biol. 1987, 196(4):901-17, which is incorporated herewith by reference).

As used herein, the term "constant region" of an antibody refers to a constant region of the antibody light chain or a constant region of the antibody heavy chain or to a combination of before-mentioned constant regions.

For producing antibodies, in particular human, humanized, chimeric antibodies, and fragments thereof, for example any of the methods as disclosed in US 2010/0196266 A1, which document is incorporated herein by reference, can be used.

Antibody fragments can be produced by several methods including, but not limited to, the following methods, such as e.g. described in US 2010/0196266 A1:

$F(ab')_2$ fragments can be generated by pepsin digestion of the antibody molecule. Fab' fragments can be for example obtained by reducing disulfide bridge(s) of the $F(ab')_2$ fragments. Alternatively, Fab' expression libraries can be for example constructed as described e.g. by Huse et al. (Science 1989, 246:1274-1281). Fab' expression libraries allow an identification of monoclonal Fab' fragments having a specificity of interest, in particular of fragments binding to CD26.

$F(ab)_2$ fragments can be produced by papain digestion of an antibody. Fab fragments can be obtained by disulfide reduction. A "Fab fragment" represents in particular a fragment that is comprised of one light chain and the CH1 and variable regions of one heavy chain. The heavy chain of a Fab molecule cannot bind via a disulfide bond to another heavy chain molecule.

Furthermore, an antibody fragment can be also a single variable region or a peptide consisting of or comprising a single complementarity-determining region (CDR).

Moreover, the antibody of the present invention can be a diabody. As used herein, "diabodies" can describe in particular small antibody fragments with two antigen-binding sites, which fragments comprise a heavy chain variable domain (VH) connected to a light chain variable domain (VL) in the same polypeptide chain (VH-VL). Unless explicitly mentioned to the contrary, the terms variable domain and variable region are used herein interchangeably. Diabodies and techniques for their production are discussed for example in EP 404 097, WO 93/11161, and in Hollinger et al., 1993, Proc. Natl. Acad Sci. USA 90: 6444-6448.

Furthermore, the antibody of the present invention can be a single chain Fv molecule. A single chain Fv molecule (abbreviated as scFv) comprises a VL domain and a VH domain, which can associate to form a binding site, in particular for CD26. These two domains are further covalently linked by a peptide linker, such as e.g. by a peptide comprising 1 to 25 amino acid residues. Unless explicitly mentioned to the contrary, the terms VL domain and VL region are used herein interchangeably. Moreover, unless explicitly mentioned to the contrary, the terms VH domain and VH region are used herein interchangeably. Methods for obtaining scFv molecules are for example described in U.S. Pat. Nos. 4,704,692, 4,946,778, R. Raag and M. Whitlow, "Single Chain Fvs." FASEB Vol. 9:73-80 (1995) and R. E. Bird and B. W. Walker, "Single Chain Antibody Variable Regions," TIBTECH, Vol. 9: 132-137 (1991).

Furthermore, the term antibody as used herein also encompasses single domain antibodies. Methods for preparing single domain antibodies (DABs) are known to a skilled person and are for example described in Cossins et al. (2006, Prot Express Purif 51:253-259), incorporated herein by reference.

According to one embodiment, an antibody or fragment thereof according to the present invention can contain at least a heavy chain CDR3, and at least a light chain CDR3; in particular, an antibody or fragment thereof according to the present invention can contain the sequence set forth in SEQ ID NO: 1, as well as at least one of the sequences set forth in SEQ ID NO: 2 and 3.

Antibody fragments can comprise at least 4 amino acids, at least 5 amino acids, at least 7 amino acids, at least 9 amino acids, in particular at least 15 amino acids. An antibody fragment of the present invention can have any upper size limit, and can have for example merely one amino acid residue less than the full-length antibody from which it is obtained.

The antibody of the present invention can be a bispecific antibody, which is capable of binding to CD26, in particular human CD26. Bispecific antibodies can be produced by several methods including e.g. fusion of hybridomas or linking of Fab' fragments. Such methods are described e.g. in Songsivilai et al., 1990, Clin. Exp. Immunol. 79: 315-321; Kostelny et al., 1992, J. Immunol. 148: 1547-1553.

According to an embodiment, the antibody of the present invention can be a monoclonal antibody. Methods for preparing monoclonal antibodies against a target antigen are known in the art, as may be seen for example from Coligan et al. (eds.), CURRENT PROTOCOLS IN IMMUNOLOGY, VOL. 1, pages 2.5.1-2.6.7 (John Wiley & Sons 1991), Kohler and Milstein, Nature 256: 495 (1975), and US 2010/0196266 A1. Monoclonal antibodies are for example obtainable by methods known to a skilled person, such as disclosed in US 2010/0196266 A1. In particular, monoclonal antibodies are obtainable by methods comprising one or more, preferably all, of the following steps: injecting mammal(s), for example a mouse with a composition comprising an antigen, removing spleen from these injected mammal(s) to obtain B-lymphocytes, fusing the so obtained B-lymphocytes with myeloma cells to produce hybridomas, cloning the hybridomas, selecting at least one positive clone producing antibodies to the antigen, culturing the at least one positive clone producing antibodies to the antigen, and isolating the antibodies from the hybridoma cultures.

MAbs (monoclonal antibodies) can be isolated and purified from hybridoma cultures using known procedures, such as disclosed in US 2010/0196266 A1. In particular, one or more isolation and/or purification procedures selected from the group consisting of size-exclusion chromatography, affinity chromatography, in particular with Protein-A Sepharose, and ion-exchange chromatography can be applied. Isolation and/or purification techniques for antibodies are for example disclosed in Baines et al., "Purification of Immunoglobulin G (IgG)," in METHODS IN MOLECULAR BIOLOGY, VOL. 10, pages 79-104 (The Humana Press, Inc. 1992), as well as in Coligan et al., supra, pages 2.7.1-2.7.12 and pages 2.9.1-2.9.3.

The term "monoclonal antibody" can in particular describe an antibody obtained from a population of substantially homogeneous antibodies, wherein the individual antibodies are identical except for possible naturally occurring mutations that can be present in low amounts.

After the initial raising of antibodies to the immunogen, in particular after the initial raising of antibodies that can specifically bind to CD26, the antibodies can be sequenced and then produced using recombinant techniques. Humanization and chimerization of non-human mammal (e.g. murine) antibodies and antibody fragments are well known to the skilled person.

The antibody of the present invention can be a humanized antibody, in particular a humanized monoclonal antibody. The term "humanized antibody" can in particular encompass antibodies produced by recombinant DNA techniques, in which some or all of the amino acids of a human immunoglobulin light or heavy chain that are not required for antigen binding (such as e.g. some or all of the amino acids of constant regions and framework regions of variable domains) are used to substitute for the corresponding amino acids from the light or heavy chain of the non-human mammal antibody (e.g. murine) antibody. Methods for producing humanized monoclonal antibodies are known in the art and are described for example in the following publications: Jones et al., Nature 321: 522 (1986), Carter et al., Proc. Nat'l Acad. Sci. USA 89: 4285 (1992), Riechmann et al., Nature 332: 323 (1988), Verhoeyen et al., Science 239: 1534 (1988), Sandhu, Crit. Rev. Biotech. 12: 437 (1992), and Singer et al., J. Immun. 150: 2844 (1993). An antibody, such as e.g. a chimeric or non-human mammal (e.g. murine) monoclonal antibody, in particular a chimeric or non-human mammalian (e.g. murine) monoclonal antibody of the present invention, can be humanized by transferring the non-human mammal (e.g. mouse) CDRs from the light and heavy variable chains of the non-human mammal immunoglobulin, for example mouse immunoglobulin, into the corresponding variable domains of a human antibody, as described e.g. in US 2010/0196266 A1. The non-human mammal framework regions (FR), for example mouse framework regions (FR), in the chimeric monoclonal antibody can be also replaced with human FR sequences. For example, an antibody of the present invention which is a humanized version of a non-human mammal (e.g. murine) antibody to CD26 can have on both of its heavy and light chains constant regions of a human antibody and/or framework regions from the variable domains of a human antibody, and/or CDRs from the non-human mammal (e.g. murine) antibody.

For improving the antibody affinity of a humanized antibody, in particular for improving its capability of binding to CD26, additional modification steps can be carried out, as described e.g. in US 2010/0196266 A1. In particular, one or more amino acid residues in the human FR regions can be replaced with amino acid residues present at corresponding positions in the non-human, in particular murine, antibody in order to maintain or improve the binding affinity of the humanized antibody to the antigen. Methods which can be applied by a skilled person are for example described in Tempest et al., Biotechnology 9:266 (1991), and Verhoeyen et al., Science 239: 1534 (1988). For example, human FR (framework region) amino acid residues which differ from their non-human mammal counterparts, for example murine counterparts, and are located close to or directly adjacent to one or more CDR amino acid residues can represent candidates for substitution.

The antibody of the present invention can be a human antibody. The term "human antibody" can in particular encompass an antibody, which has an amino acid sequence corresponding to that of an antibody produced by a human and/or has been made using known techniques for producing human antibodies. In particular, the term "human antibody" can include antibodies comprising at least one human heavy chain polypeptide or at least one human light chain polypeptide.

In particular, the antibody of the present invention can be a fully human antibody. In the context of the present application, the term "fully human antibody" can in particular refer to an antibody containing human heavy chain and human light chain polypeptides. Methods for producing human antibodies, in particular fully human antibodies, using for example combinatorial approaches or transgenic animals transformed with human immunoglobulin loci, are known to a skilled person, as may be seen e.g. from US 2010/0196266 A1. Such methods are for example described in Conrad and Scheller, 2005, Comb. Chem. High Throughput Screen. 8:117-26; Mancini et al., 2004, New Microbiol. 27:315-28; Brekke and Loset, 2003, Curr. Opin. Pharmacol. 3:544-50). A fully human antibody is for example also obtainable using genetic or chromosomal transfection methods or using phage display technology. Genetic or chromosomal transfection methods, as well as phage display technology are known in the art and are described for example in McCafferty et al., 1990, Nature 348:552-553. In particular, human antibodies can be also obtained by introducing human immunoglobulin loci into transgenic animals, such as e.g. mice, goats or cows, wherein the endogenous immunoglobulin genes were completely or partially inactivated. Such procedures are described e.g. in U.S. Pat. Nos. 5,545,806, 5,633,425, and 5,661,016. According to an alternative procedure, the human antibody can be obtained by immortalizing human B lymphocytes that produce an antibody directed against a target antigen, in particular that produce an antibody to CD26. Such procedures are known in the art and are described e.g. in Cole et al., Monoclonal Antibodies and Cancer Therapy, Alan R. Liss, p. 77 (1985); Boerner et al., 1991, J. Immunol., 147 (I):86-95.

In particular, the phage display technique can be used for generating a human antibody, as known in the art and as described e.g. in Dantas-Barbosa et al., 2005, Genet. Mol. Res. 4:126-40 and US 2010/0196266 A1. Human antibodies can be generated from normal humans or from humans having a particular disease state (Dantas-Barbosa et al., 2005). This technique allows constructing human antibodies from a diseased individual.

For example, a phage display library of human Fab antibody fragments from osteosarcoma patients can be constructed, as disclosed in Dantas-Barbosa et al. (2005, supra) and as discussed e.g. in US 2010/0196266 A1. In particular, total RNA can be obtained from circulating blood lymphocytes (Id.). Recombinant Fab can be cloned from μ, γ and κ chain antibody repertoires and inserted into a phage display library (Id.). RNAs can be converted to cDNAs and used to provide Fab cDNA libraries using specific primers against heavy and light chain immunoglobulin sequences (Marks et al., 1991, J. Mol. Biol. 222:581-97). In a next step, library construction can be performed as known to a skilled person and as described for example by Andris-Widhopf et al. (2000), Phage Display Laboratory Manual, $1^{st}$ edition, Cold Spring Harbor Laboratory Press, pp. 9.1 to 9.22). The final Fab fragments can be digested with restriction endonucleases and inserted into a bacteriophage genome to produce the phage display library. Finally, the so obtained libraries can be screened using standard phage display methods, as known in the art and as described e.g. in Pasqualini and Ruoslahti, 1996, Nature 380:364-366; Pasqualini, 1999, The Quart. J. Nucl. Med. 43:159-162). Phage display can be performed in several formats, as may be seen e.g. from Johnson and Chiswell, 1993, *Current Opinion in Structural Biology* 3:5564-571.

Moreover, human antibodies can be generated by in vitro activated B cells. This procedure is described e.g. in U.S. Pat. Nos. 5,567,610 and 5,229,275, which both are incorporated herein by reference.

The antibody of the present invention can be a chimeric antibody. In particular, a chimeric antibody can be a recombinant protein, wherein the variable regions of a human antibody have been replaced by the variable regions of a non-human mammal antibody, such as e.g. a mouse antibody or a rabbit antibody, including the complementarity-determining regions (CDRs) of the non-human mammal antibody, e.g. the mouse antibody or rabbit antibody. Procedures for cloning non-human mammal immunoglobulin variable domains, in particular murine immunoglobulin variable domains, are known in the art and are for example described by Orlandi et al., Proc. Nat'l Acad. Sci. USA 86: 3833 (1989), and US 2010/0196266 A1. Methods for obtaining chimeric antibodies are known to the skilled person, as may be e.g. seen from Leung et al., Hybridoma 13:469 (1994), wherein the production of an LL2 chimera is described.

Antibodies of the present invention can furthermore comprise one or more additional moieties to effect desired functions. In particular, the antibodies can include one or more toxin moieties (such as e.g. a tetanus toxoid) or radionuclide(s), and/or one or more moieties (such as e.g. biotin, fluorescent moiety, radioactive moiety, histidine tag or other peptide tags) for facilitating isolation and/or detection and/or targeting, wherein said tag preferably does not or does essentially not alter the binding specificity of said antibody.

The terms "has specificity for", "exhibits a specific binding to", "capable of specifically binding to" and "specifically binds to" are used interchangeably in the present application and can in particular indicate that the antibody reacts or associates more frequently, more rapidly, with greater duration, with greater affinity, or with some combination of the above to an epitope or protein than with alternative substances, including unrelated proteins. According to one embodiment, "binding" and "specifically binding", as well as "antibody binding to" and "antibody specifically binding to" may be used interchangeably in the context of the present invention.

In certain embodiments, an anti-CD26 disclosed herein binds to human CD26 with a kinetic dissociation rate ($K_{off}$) of about $1 \cdot e^{-3}$ to $1 \cdot e^{-5}$ $s^{-1}$, preferably $5 \cdot e^{-3}$ to $5 \cdot e^{-4}$ $s^{-1}$, more preferably $8 \cdot e^{-3}$ to $3 \cdot e^{-4}$ $s^{-1}$ in particular about $1.32 \cdot e^{-4}$ $s^{-1}$.

In certain embodiments, an anti-CD26 disclosed herein binds to human CD26 with a kinetic dissociation constant ($K_D$) of about $5 \cdot e^{-8}$ to $5 \cdot e^{-10}$ M, preferably $2 \cdot e^{-9}$ to $1 \cdot e^{-10}$ M, more preferably $3 \cdot e^{-9}$ to $7 \cdot e^{-9}$ M, in particular about $5.02 \cdot e^{-9}$ M.

In certain embodiments, an anti-CD26 disclosed herein binds to human CD26 with a kinetic association constant ($K_{on}$) of about $5 \cdot e^3$ to $1 \cdot e^5$ 1/Ms, preferably $1 \cdot e^4$ to $5 \cdot e^4$ 1/Ms, more preferably $1.5 \cdot e^4$ to $3.5 \cdot e^4$ 1/Ms, in particular about $2.63 \cdot e^4$ 1/Ms.

In certain embodiments, an anti-CD26 antibody disclosed herein binds to human CD26 with a dissociation constant of about 1 nM or less, about 3 nM or less, about 6 nM or less, about 12 nM or less, about 30 nM or less, about 60 nM or less, about 200 nM or less.

In some embodiments an anti-CD26 antibody disclosed herein binds to human CD26 with a dissociation constant of about 0.1 nM to about 10 nM, about 0.1 nM to about 6 nM, about 0.1 nM to about 3 nM, or about 0.1 nM to about 1 nM.

The antibodies of the present invention can be assayed for specific binding by any method known to a skilled person, including, but not limited to, competitive and non-competitive assay systems using techniques such as Biacore® analysis, FACS analysis, immunofluorescence, immunocytochemistry, Western blots, radioimmunoassays, ELISA, "sandwich" immunoassays, immunoprecipitation assays, precipitation reactions, immunodiffusion assays, agglutination assays, complement-fixation assays, immunoradiometric assays, fluorescent immunoassays, and protein A immunoassays. Such assays are described e.g. in Ausubel et al., eds., 1994, Current Protocols in Molecular Biology, Vol. 1, John Wiley & Sons, Inc., New York and U.S. Pat. No. 7,982,013 B2, which are incorporated by reference herein in entirety. Preferably, Biacore® analysis may be carried out.

Native antibodies can be made up of two or more heterodimeric subunits each containing one heavy (H) and one light (L) chain. An individual native antibody can have one type of L chain and one type of H chain, which are held together by disulfide bonds to form a heterodimeric subunit.

The term "peptide" can in particular refer to a compound that includes two or more amino acids. The amino acids can be linked together by a peptide bond. A peptide can comprise naturally occurring amino acids and/or non-naturally occurring amino acids; in particular a peptide can comprise L-amino acids and/or D-amino acids. Short peptides, e.g., peptides having less than ten amino acid units, are sometimes referred to as "oligopeptides". Other peptides having a large number of amino acid residues, e.g. up to 100 or more, can be referred to as "polypeptides". As used herein, the term "polypeptide" can refer to any peptide containing three or more amino acids. As used herein, any reference to a "polypeptide" also includes an oligopeptide, and any reference to a "peptide" includes polypeptides, oligopeptides, and proteins.

An antibody of the present invention can be an antibody of any class. In particular, an antibody of the present invention can have an antibody isotype selected from the group consisting of IgG1, IgG2, IgG3, IgG4, IgM, IgA, IgD and IgE. In particular an antibody of the present invention can be of IgG2 class, especially of IgG 2B class. The term "isotype", as used herein, can in particular refer to the antibody class (such as e.g. IgG) that is encoded by heavy chain constant region genes. Sequences of human immunoglobulin constant regions will be apparent to the skilled person and/or are available in public databases (e.g. National Center for Biotechnology Information (NCBI), U.S. National Library of Medicine).

Furthermore, an antibody of the present invention specifically binds CD26 and can have a light chain variable region, which light chain variable region comprises a variant of a VL CDR1, VL CDR2, or VL CDR3 of the light chain variable region of an antibody produced by the hybridoma cell line deposited as PD 12002. Moreover, an antibody of the present invention specifically binds CD26 and can have a heavy chain variable region, which heavy chain variable region comprises a variant of a VH CDR1, VH CDR2, or VH CDR3 of the heavy chain variable region of an antibody produced by the hybridoma cell line deposited as PD 12002. In one embodiment, a variant VH or VL CDR can have at least 90%, preferably at least 98%, more preferably at least 99% sequence identity to the corresponding VH or VL CDR of an antibody produced by the hybridoma cell line deposited as PD 12002. Alternatively, a variant VH or VL CDR can be a VH or VL CDR of an antibody produced by the hybridoma cell line deposited as PD 12002, wherein not more than 5, 4, 3, 2, more preferably 1 amino acid residue(s), respectively, have been deleted, inserted or replaced by an amino acid residue different from the replaced amino acid residue. In one embodiment, the amino acid replacement is a conservative change. In one embodiment, the VH and VL CDRs of an antibody produced by the hybridoma cell line deposited as PD 12002 are listed in FIG. 2*b*.

Furthermore, an antibody of the present invention specifically binds CD26 and can have a light chain variable region, which light chain variable region comprises an amino acid sequence selected from the group consisting of SEQ ID NOs: 4, 5, 6 to 21, a variant of the amino acid sequence of SEQ ID NO: 4, and a variant of the amino acid sequence of SEQ ID NO: 5. Moreover, an antibody of the present invention specifically binds CD26 and can have a light chain variable region, which light chain variable region comprises an amino acid sequence selected from variants of an amino acid sequence selected from the group consisting of SEQ ID NOs: 6 to 21. The variant of SEQ ID NO: 4 can have at least 90%, preferably at least 98%, more preferably at least 99% sequence identity to SEQ ID NO: 4. The variant of SEQ ID NO: 5 can have at least 90%, preferably at least 98%, more preferably at least 99% sequence identity to SEQ ID NO: 5. A variant of an amino acid sequence selected from the group consisting of SEQ ID NOs: 6 to 21 can have at least 90%, preferably at least 98%, more preferably at least 99% sequence identity to the amino acid sequence selected from the group consisting of SEQ ID NOs: 6 to 21. Alternatively, a variant of an amino acid sequence selected from the group consisting of SEQ ID NOs: 4, 5, 6 to 21 can be an amino acid sequence selected from the group consisting of SEQ ID NOs: 4, 5, 6 to 21, wherein not more than 8, preferably not more than 5, more preferably 1 amino acid residue(s), respectively, have been deleted, inserted or replaced by an amino acid residue different from the replaced amino acid residue. In one embodiment, the amino acid replacement is a conservative change. In particular, an anti-CD26 antibody of the present invention can be an antibody, wherein the light chain variable region can comprise or consist of an amino acid sequence selected from the group consisting of SEQ ID NOs: 4 to 21 or variants thereof, as shown e.g. in FIG. 3. Furthermore, an antibody of the present invention specifically binds CD26 and can have a light chain variable region, which light chain variable region comprises amino acid residues 8-104 of SEQ ID NO: 4 or 5.

A "conservative amino acid change" is a change, wherein one amino acid residue is replaced with another amino acid residue having a similar side chain. The term is interchangeably used with "conservative amino acid substitution" or "conservative amino acid variation". Families of amino acid residues having similar side chains are known in the art, including basic side chains, acidic side chains, uncharged polar side chains, nonpolar side chains, beta-branched side chains and aromatic side chains, as discussed e.g. in U.S. Pat. No. 7,982,013 B2, in particular column 22 thereof. For example, substitution of a phenylalanine for a tyrosine is a conservative substitution. Preferably, the antibody obtained after conservative substitution specifically binds to CD26, in particular human CD26. Methods for identifying nucleotide and amino acid conservative substitutions which do not eliminate antigen binding are known in the art (see, e.g., Brummell et al., Biochem. 32: 1180-1 187 (1993); Kobayashi et al., Protein Eng. 12(10):879-884 (1999); and Burks et al., Proc. Natl. Acad. Sci. USA 94:412-417 (1997)).

According to one embodiment, in variants of amino acid sequences comprising one or more CDR sequences, all CDR sequences or at least all CDR3 sequence(s) can remain unchanged. In particular, in variants of amino acid sequences comprising one or more amino acid sequences set forth in SEQ ID NOs: 1, 2 and 3, the one or more amino acid sequences set forth in SEQ ID NOs: 1, 2 and 3 can remain unchanged. According to one embodiment, in variants of nucleotide sequences comprising sections coding for one or more CDR sequences, all sections coding for CDR sequences or at least all nucleotide sequence sections coding for CDR3 sequence(s) can remain unchanged. In particular, in variants of nucleotide sequences comprising one or more sequences coding for one or more sequences set forth in SEQ ID NOs: 1, 2 and 3, at least nucleotide sequence sections coding for one or more of SEQ ID NOs: 1, 2 and 3 can remain unchanged. According to one embodiment, in an antibody comprising a variant of an amino acid sequence selected from the group consisting of SEQ ID NOs: 4 to 21, the light chain variable region can comprise amino acid residues 8-104 of SEQ ID NO: 4 or 5 and/or in an antibody comprising a variant of an amino acid sequence selected from the group consisting of SEQ ID NOs: 22 to 47, the heavy chain variable region can comprise amino acid residues 7-112 of SEQ ID NO: 26.

"Percent (%) amino acid sequence identity" with respect to a polypeptide sequence as set forth herein is defined as the percentage of amino acid residues in a candidate sequence of interest to be compared that are identical with the amino acid residues in a particular polypeptide sequence as set forth herein (e.g. a particular polypeptide sequence characterized by a SEQ. ID. NO. in the sequence listings), after aligning the sequences and introducing gaps, if necessary, to achieve the maximum percent sequence identity, and not considering any conservative substitutions as part of the sequence identity. A sequence alignment performed for determining percent amino acid sequence identity can be carried out according to procedures known in the art, as described for example in EP 1 241 179 B1, which is incorporated herewith by reference, including in particular page 9, line 35 to page 10, line 40 with the definitions used therein and Table 1 regarding possible conservative substitutions. For example, a skilled person can use publicly available computer software. Computer program methods for determining sequence identity include, but are not limited to BLAST, BLAST-2, ALIGN or Megalign (DNASTAR) software. According to one preferred embodiment, the software alignment program used can be BLAST. A skilled person can determine appropriate parameters for measuring alignment, including any algorithms needed to achieve maximal alignment over the full length of the sequences subjected to comparison. According to a preferred embodiment, the % identity values can be generated using the WU-BLAST-2 computer program (Altschul et al., 1996, Methods in Enzymology 266: 460-480, which is incorporated herewith by reference), as described e.g. in EP 1 241 179 B1. According to a preferred embodiment, the following parameters are used, when carrying out the WU-BLAST-2 computer program: Most of the WU-BLAST-2 search parameters were set to the default values. The adjustable parameters were set with the following values: overlap span=1, overlap fraction=0.125, word threshold (T)=11, and scoring matrix=BLOSUM62. The HSP S and HSP S2 parameters, which are dynamic values used by BLAST-2, are established by the program itself depending upon the composition of the sequence of interest and composition of the database against which the sequence is being searched. However, the values can be adjusted to increase sensitivity. A % sequence identity value can be determined by dividing (a) the number of matching identical amino acid residues between a particular amino acid sequence as set forth herein which is subjected to comparison (e.g. a particular polypeptide sequence characterized by a SEQ. ID. NO. in the sequence listings) and the candidate amino acid sequence of interest to be compared, for example the number of matching identical amino acid residues as determined by WU-BLAST-2, by (b) the total number of amino acid residues of the polypeptide sequence as set forth herein which is subjected to comparison (e.g. a particular polypeptide sequence characterized by a SEQ. ID. NO. in the sequence listings).

"Percent (%) nucleic acid sequence identity" with respect to a nucleic acid sequence as set forth herein is defined as the percentage of nucleotides in a candidate sequence of interest to be compared that are identical with the nucleotides in a particular nucleic acid sequence as set forth herein (e.g. a particular polypeptide sequence characterized by a SEQ. ID. NO. in the sequence listings), after aligning the sequences and introducing gaps, if necessary, to achieve the maximum percent sequence identity. An alignment for purposes of determining percent nucleic acid sequence identity can be carried out according to procedures known in the art, as described for example in EP 1 241 179 B1. For example, a skilled person can use publicly available computer software, such as using publicly available computer software such as BLAST, BLAST-2, ALIGN or Megalign (DNASTAR) software. A skilled person can determine appropriate parameters for measuring alignment, including any algorithms needed to achieve maximal alignment over the full length of the sequences subjected to comparison. According to a preferred embodiment, the % identity values can be generated using the WU-BLAST-2 computer program, as described for example in EP 1 241 179 B1. According to a preferred embodiment, the following computer program and parameters are used: The identity values used herein are generated by the BLASTN module of WU-BLAST-2 set to the default parameters, with overlap span and overlap fraction set to 1 and 0.125, respectively. A nucleic acid sequence identity value can be obtained by dividing (a) the number of matching identical nucleotides between a particular nucleic acid sequence as set forth herein which is subjected to comparison (e.g. a particular nucleic acid sequence characterized by a SEQ. ID. NO. in the sequence listings), and the comparison nucleic acid molecule of interest to be compared, for example the number of matching identical nucleotides as determined by WU-BLAST-2, by (b) the total number of nucleotide residues of the particular nucleic acid sequence as set forth herein which is subjected to comparison (e.g. a particular nucleic acid sequence characterized by a SEQ. ID. NO. in the sequence listings).

In particular, sequence identity can be determined over the full length of a respective amino acid sequence as set forth in one of SEQ ID NO: 1 to 49 or over the full length of a respective nucleotide sequence as set forth in one of SEQ ID NO: 50 to 128.

The term "positives", in the context of sequence comparison performed as described above and in EP 1 241 179

B1, includes residues in the sequences compared that are not identical but have similar properties (e.g. as a result of conservative substitutions). The % value of positives is determined by the fraction of residues scoring a positive value in the BLOSUM 62 matrix divided by the total number of residues in the aligned region.

Moreover, an antibody of the present invention specifically binds CD26 and can have a heavy chain variable region, which heavy chain variable region comprises an amino acid sequence selected from the group consisting of SEQ ID NOs: 22 to 47 and variant(s) thereof. A variant of an amino acid sequence selected from the group consisting of SEQ ID NOs: 22 to 47 can have at least 90%, preferably at least 98%, more preferably at least 99% sequence identity to the amino acid sequence selected from the group consisting of SEQ ID NOs: 22 to 47. Alternatively, a variant of an amino acid sequence selected from the group consisting of SEQ ID NOs: 22 to 47 can be an amino acid sequence, wherein not more than 8, preferably not more than 5, more preferably 1 amino acid residue(s), respectively, have been deleted, inserted or replaced by an amino acid residue different from the replaced amino acid residue. In one embodiment, the amino acid replacement is a conservative change. In particular, an anti-CD26 antibody of the present invention can be an antibody, wherein the heavy chain variable region can comprise or consist of an amino acid sequence selected from the group consisting of SEQ ID NOs: 22 to 47 or variants thereof. Furthermore, an antibody of the present invention specifically binds CD26 and can have a heavy chain variable region, which heavy chain variable region comprises amino acid residues 7-112 of SEQ ID NO: 26. In one embodiment, an antibody of the present invention can be a chimeric antibody comprising human light chain and heavy chain constant regions.

Furthermore, an antibody of the present invention can comprise a light chain constant region, said light chain constant region comprising an amino acid sequence selected from the group consisting of SEQ ID NO: 48 and variant(s) thereof. A variant of the amino acid sequence as set forth in SEQ ID NO: 48 can have at least 90%, preferably at least 98%, more preferably at least 99% sequence identity to SEQ ID NO: 48. Alternatively, a variant of SEQ ID NO: 48 can be an amino acid sequence of SEQ ID NO: 48, wherein not more than 8, preferably not more than 5, more preferably 1 amino acid residue(s), respectively, have been deleted, inserted or replaced by an amino acid residue different from the replaced amino acid residue. In one embodiment, the amino acid replacement is a conservative change. In particular, an antibody of the present invention can be an antibody, wherein the light chain constant region can comprise or consist of an amino acid sequence set forth in SEQ ID NO: 48 or a variant thereof.

In an alternative embodiment, an antibody of the present invention can be a chimeric antibody comprising human light chain constant regions.

Moreover, an antibody of the present invention can comprise an amino acid sequence set forth in SEQ ID NO: 49, or a variant thereof. A variant of the amino acid sequence as set forth in SEQ ID NO: 49 may have at least 90%, preferably at least 98%, more preferably at least 99% sequence identity to SEQ ID NO: 49. Alternatively, a variant of SEQ ID NO: 49 can be an amino acid sequence, wherein not more than 8, preferably not more than 5, more preferably 1 amino acid residue(s), respectively, have been deleted, inserted or replaced by an amino acid residue different from the replaced amino acid residue. In one embodiment, the amino acid replacement is a conservative change. In particular, an antibody of the present invention can be an antibody, wherein the CH1-CH2-CH3 chain can comprise or consist of an amino acid sequence set forth in SEQ ID NO: 49 or a variant thereof.

In an alternative embodiment, an antibody of the present invention can be a chimeric antibody comprising human heavy chain constant region.

In particular, an antibody of the present invention can be of IgG 2B class, and can comprise an amino acid sequence set forth in SEQ ID NO: 49, or a variant thereof, as defined supra.

As may be seen from the sequence listings annexed, a group of sequences has been identified for heavy chain variable region (VH), and 2 different groups of sequences have been identified for light chain variable region (VL). Alignments of sequences of each group, showing their similarity, are shown in FIG. 3. A VL sequence (SEQ. ID. NO: 4) present in high frequency in antibodies of the present invention has been identified and the corresponding CL sequence (SEQ. ID. NO: 48) has been recognized. A VH sequence present in high frequency has been identified (SEQ. ID. NO: 26) and the corresponding CH1-CH2-CH3 sequence (SEQ. ID. NO: 49) has been recognized.

An antibody of the present invention can be an antibody which specifically binds to CD26, comprises a light chain variable region comprising an amino acid sequence set forth in SEQ ID NO: 4 or a variant thereof and/or an amino acid sequence set forth in SEQ ID NO: 5 or a variant thereof and comprises a light chain constant region comprising an amino acid sequence set forth in SEQ ID NO: 48 or a variant thereof. An antibody of the present invention can be an antibody which specifically binds CD26, comprises a heavy chain variable region comprising an amino acid sequence set forth in SEQ ID NO: 26 or a variant thereof and comprises a CH1-CH2-CH3 chain comprising an amino acid sequence set forth in SEQ ID NO: 49 or a variant thereof. Furthermore, an antibody of the present invention can be an antibody which specifically binds CD26, comprises a light chain variable region comprising an amino acid sequence set forth in SEQ ID NO: 4 or a variant thereof and optionally further comprises a light chain constant region comprising an amino acid sequence set forth in SEQ ID NO: 48 or a variant thereof and optionally further comprises a CH1-CH2-CH3 chain comprising an amino acid sequence set forth in SEQ ID NO: 49 or a variant thereof and optionally further comprises a heavy chain variable region comprising an amino acid sequence set forth in SEQ ID NO: 26 or a variant thereof. In particular, an antibody of the present invention can comprise a light chain variable region comprising an amino acid sequence set forth in SEQ ID NO: 4 or a variant thereof, a light chain constant region comprising an amino acid sequence set forth in SEQ ID NO: 48 or a variant thereof, a CH1-CH2-CH3 chain comprising an amino acid sequence set forth in SEQ ID NO: 49 or a variant thereof and a heavy chain variable region comprising an amino acid sequence set forth in SEQ ID NO: 26 or a variant thereof. Alternatively, an antibody of the present invention can be a chimeric antibody comprising a human light chain and/or heavy chain constant region.

In particular, an antibody of the present invention can be an antibody which specifically binds to CD26, comprises a light chain variable region comprising amino acid residues 8-104 of SEQ ID NO: 4, a light chain constant region comprising an amino acid sequence set forth in SEQ ID NO: 48 or a variant thereof, a CH1-CH2-CH3 chain comprising an amino acid sequence set forth in SEQ ID NO: 49 or a variant thereof and a heavy chain variable region comprising amino acid residues 7-112 of SEQ ID NO: 26. Alternatively, an antibody of the present invention can be a chimeric antibody comprising a human light chain and/or heavy chain constant region.

In particular, an antibody of the present invention can be an antibody which specifically binds to CD26, comprises a light chain variable region comprising an amino acid sequence set forth in SEQ ID NO: 5 or a variant thereof, a CH1-CH2-CH3 chain comprising an amino acid sequence set forth in SEQ ID NO: 49 or a variant thereof and a heavy chain variable region comprising amino acid residues 7-112 of SEQ ID NO: 22. Alternatively, an antibody of the present invention can be a chimeric antibody comprising a human light chain and/or heavy chain constant region.

An antibody of the present invention can be in particular an antibody which specifically binds to CD26, comprises a light chain variable region comprising an amino acid sequence selected from the group consisting of SEQ ID NOs: 4, 5, 6, 7, 8, 9, 10, 11, 12, 13, 14, 15, 16, 17, 18, 19, 20, 21 or variant(s) thereof and comprises a light chain constant region comprising an amino acid sequence set forth in SEQ ID NO: 48 or a variant thereof and comprises a CH1-CH2-CH3 chain comprising an amino acid sequence set forth in SEQ ID NO: 49 or a variant thereof; optionally, this antibody furthermore comprises a heavy chain variable region comprising an amino acid sequence selected from the group consisting of SEQ ID NO: 22, 23, 24, 25, 26, 27, 28, 29, 30, 31, 32, 33, 34, 35, 36, 37, 38, 39, 40, 41, 42, 43, 44, 45, 46, 47 or variant(s) thereof. Alternatively, an antibody of the present invention can be a chimeric antibody comprising a human light chain and/or heavy chain constant region.

An antibody of the present invention can be in particular an antibody which specifically binds to CD26, comprises a light chain variable region comprising an amino acid sequence set forth in SEQ ID NO: 4 or variant(s) thereof and comprises a light chain constant region comprising an amino acid sequence set forth in SEQ ID NO: 48 or a variant thereof and comprises a CH1-CH2-CH3 chain comprising an amino acid sequence set forth in SEQ ID NO: 49 or a variant thereof; optionally, this antibody furthermore comprises a heavy chain variable region comprising an amino acid sequence selected from the group consisting of SEQ ID NO: 22, 23, 24, 25, 26, 27, 28, 29, 30, 31, 32, 33, 34, 35, 36, 37, 38, 39, 40, 41, 42, 43, 44, 45, 46, 47 or variant(s) thereof. Alternatively, an antibody of the present invention can be a chimeric antibody comprising a human light chain and/or heavy chain constant region.

An antibody of the present invention can be in particular an antibody which specifically binds to CD26, comprises a light chain variable region comprising an amino acid sequence set forth in SEQ ID NO: 5 or variant(s) thereof and comprises a CH1-CH2-CH3 chain comprising an amino acid sequence set forth in SEQ ID NO: 49 or a variant thereof; this antibody can optionally furthermore comprise a heavy chain variable region comprising an amino acid sequence selected from the group consisting of SEQ ID NO: 22, 23, 24, 25, 26, 27, 28, 29, 30, 31, 32, 33, 34, 35, 36, 37, 38, 39, 40, 41, 42, 43, 44, 45, 46, 47 or variant(s) thereof. Alternatively, an antibody of the present invention can be a chimeric antibody comprising a human light chain and/or heavy chain constant region.

An antibody of the present invention can be in particular an antibody which specifically binds to CD26, comprises a heavy chain variable region comprising an amino acid sequence set forth in SEQ ID NO: 26 or variant(s) thereof and comprises a light chain constant region comprising an amino acid sequence set forth in SEQ ID NO: 48 or a variant thereof and comprises a CH1-CH2-CH3 chain comprising an amino acid sequence set forth in SEQ ID NO: 49 or a variant thereof; this antibody can optionally furthermore comprise a light chain variable region comprising an amino acid sequence selected from the group consisting of SEQ ID NOs: 4, 5, 6, 7, 8, 9, 10, 11, 12, 13, 14, 15, 16, 17, 18, 19, 20, 21 or variant(s) thereof. Alternatively, an antibody of the present invention can be a chimeric antibody comprising a human light chain and/or heavy chain constant region.

A variant of any one of the sequences selected from the group of sequences SEQ ID NO: 1 to 128 can have at least 90%, preferably at least 98%, more preferably at least 99% sequence identity to said sequence selected from said group of sequences.

Moreover, an antibody of the present invention specifically binds CD26 and can comprise a heavy chain variable region and a light chain variable region, wherein the amino acid sequences of the heavy chain variable region are those of a heavy chain variable region of an antibody produced by the hybridoma cell line deposited at CBA-ICLC of Genoa (Italy) as PD 12002, and the amino acid sequences of the light chain variable region are those of a light chain variable region of an or this antibody produced by the hybridoma cell line deposited as PD 12002. In particular, the amino acid sequences of the heavy chain can be those of a heavy chain of an antibody produced by the hybridoma cell line deposited as PD 12002, and/or the amino acid sequences of the light chain can be those of a light chain of an or this antibody produced by the hybridoma cell line deposited as PD 12002. In particular, the antibody of the present invention specifically binding to CD26 can comprise the same heavy chain sequences and the same light chain sequences as an antibody produced by the hybridoma cell line deposited as PD 12002. Alternatively, an antibody of the present invention can be a chimeric antibody comprising a human light chain and/or heavy chain constant region.

An anti-CD26 antibody of the present invention (e.g. an antibody that specifically binds CD26 and comprises a heavy chain variable region comprising SEQ ID NO:1, and/or comprises a light chain variable region comprising SEQ ID NO:2 and/or SEQ ID NO:3) can be an antibody, wherein furthermore the amino acid sequences of the heavy chain variable region can be those of a heavy chain variable region of an antibody produced by the hybridoma cell line deposited at CBA-ICLC of Genoa (Italy) as PD 12002, and the amino acid sequences of the light chain variable region can be those of a light chain variable region of an antibody produced by the hybridoma cell line deposited as PD 12002. Optionally, the amino acid sequence of the CDR3 of the heavy chain variable region can be that of a heavy chain variable region of an antibody produced by the hybridoma cell line deposited as PD 12002. Optionally, the amino acid sequence of the CDR3 of the light chain variable region can be that of a light chain variable region of an antibody produced by the hybridoma cell line deposited as PD 12002. Alternatively, an antibody of the present invention can be a chimeric antibody comprising a human light chain and/or heavy chain constant region.

The term "hybridoma cell line" also includes the progeny of the hybridoma cell line, whether or not the progeny is identical in morphology or in genetic make-up. Because certain modifications may occur, for example due to mutation and/or environmental influences, such progeny may not be identical to the parent cell line. Preferably, cell progeny of this hybridoma cell line will produce an antibody, or an antibody fragment, capable of binding to CD26, especially to human CD26, in particular will produce an antibody of the present invention. Moreover, the term "hybridoma cell line" can also encompass mixtures of hybridoma cell lines, producing an antibody mixture.

According to another aspect, the present invention provides an antibody mixture. The present invention also provides a composition, in particular an isolated composition, comprising the antibody mixture. This antibody mixture can comprise at least two different antibodies, which at least two different antibodies preferably can specifically bind to CD26, especially human CD26. Optionally, at least one antibody which does not bind to CD26 can be present in the antibody mixture. According to one embodiment, at least two or all antibodies of the composition can specifically bind to CD26, especially human CD26. In particular, one or more or all of the antibodies present in the antibody mixture can be antibodies of the present invention and can optionally have further features of the antibodies of the present invention as disclosed supra. This antibody mixture can comprise a first antibody, said first antibody comprising a light chain variable region comprising the sequence set forth in SEQ ID NO: 2 and/or the sequence set forth in SEQ ID NO: 3, in particular in SEQ ID NO: 3, and a second antibody, said second antibody comprising a light chain variable region comprising the sequence set forth in SEQ ID NO: 2. The first antibody and/or the second antibody can be antibodies of the present invention and can optionally have one or more further features of antibodies of present invention as discussed in detail supra. In one embodiment, the antibody mixture comprises or consists of antibodies having a heavy chain variable region comprising a VH CDR1 of SEQ ID NO: 133, a VH CDR2 of SEQ ID NO: 134, and a VH CDR3 of SEQ ID NO: 1.

According to a preferred embodiment of the invention, the antibody mixture comprises at least one or comprises or consists of two antibodies having the following combination of sequences (each antibody comprising one of the light chain sequences indicated below together with the heavy chain sequence indicated below):

One of the following two different light chains comprising a) Light chain variable region comprising SEQ ID NO: 4, or a variant of SEQ ID NO: 4, in particular any of SEQ ID NO: 6 to SEQ ID NO: 21, together with light chain constant region comprising SEQ ID NO: 48; or b) Light chain variable region comprising SEQ ID NO: 5, Together with a heavy chain comprising:

Heavy chain variable region comprising SEQ ID NO: 26 or a variant of SEQ ID NO: 26, in particular any sequence selected from of SEQ ID NO: 22 to SEQ ID NO: 25 and SEQ ID NO: 27 to SEQ ID NO: 47, together with heavy chain constant region (CH1-CH2-CH3) comprising SEQ ID NO: 49.

In one embodiment, the antibody mixture comprises or consists of the antibodies produced by the PD 12002 hybridoma deposit. In one embodiment, the isolated composition comprises at least one of the antibodies produced by the PD 12002 hybridoma deposit, in particular comprises the antibodies produced by the PD 12002 hybridoma deposit.

During the numerous experiments performed by the present inventors, the antibodies produced by the PD 12002 hybridoma deposit showed up to have surprisingly beneficial activities for use as a medicament, in particular for promoting engraftment after haematopoietic stem cell transplantation and/or preventing and/or treating at least one of Graft-versus-Host Disease and Aplastic Anemia.

The PD 12002 hybridoma cell line as deposited is stable in storage and culture and has been cultivated and verified for stability and identity over more than 5 years.

In another aspect, the invention provides an agent (in particular antibody or fragment thereof) that competes for specific binding to CD26, in particular to human CD26, with an antibody in a competitive binding assay (e.g., in an in vitro competitive binding assay), wherein the antibody is an antibody of the present invention; in particular, this agent can compete for specific binding to CD26, in particular to human CD26, with an antibody which can comprise a) a heavy chain variable region comprising the sequence set forth in SEQ ID NO: 1 and/or a light chain variable region comprising the sequence set forth in SEQ ID NO: 2 and/or the sequence set forth in SEQ ID NO: 3;

b) a heavy chain variable region of an antibody produced by the hybridoma cell line deposited at CBA-ICLC, Genoa, Italy as PD12002 and a light chain variable region of said antibody produced by said hybridoma cell line deposited at CBA-ICLC, Genoa, Italy as PD12002. According to one embodiment, the antibody can be an antibody which can comprise a) a heavy chain variable region comprising an amino acid sequence selected from the group consisting of SEQ ID NOs: 22 to 47 and variant(s) thereof, and/or a light chain variable region comprising an amino acid sequence selected from the group consisting of SEQ ID NOs: 4, 5, 6 to 21, and variant(s) thereof, or an antibody which can comprise b) a heavy chain and a light chain of an antibody produced by the hybridoma cell line deposited at CBA-ICLC, Genoa, Italy as PD12002. According to a preferred embodiment, the invention provides an agent (in particular antibody or fragment thereof) that competes for specific binding to CD26, in particular to human CD26, in a competitive binding assay (e.g., in an in vitro competitive binding assay) with an antibody comprising a heavy chain variable region sequence ID NO: 26 and a light chain variable region sequence ID NO: 4 and/or sequence ID NO: 5. Competitive binding assay can be used to determine whether two antibodies bind the same epitope by recognizing identical or sterically overlapping epitopes (Dong et. al 1998). Any competitive binding assay known to one of skill can be used to identify an agent that competes for specific binding to CD26 with an antibody of the present invention. For example, assays in which a CD26 antigen is immobilized on a multi-well plate and the ability of unlabelled antibody to block the binding of labelled antibodies is measured can be used. Common labels for such competition assays are radioactive labels or enzyme labels.

According to another aspect, an isolated nucleic acid molecule comprising (a) a nucleotide sequence encoding an antibody of the present invention or (b) a nucleotide sequence complementary to (a) is provided by the inventors.

In the context of the present invention, the term "nucleic acid molecule" is used as known in the art and can in particular refer to two or more nucleotides or nucleotide analogs linked by a covalent bond. The term "nucleic acid molecule" encompasses oligonucleotides, which generally comprise not more than about fifty nucleotides, and polynucleotides, which can have essentially any length. Furthermore, the term "nucleic acid molecule" can encompass DNA, such as a cDNA or a gene, or RNA. The nucleotides comprising a nucleic acid molecule can be for example selected from the group comprising naturally occurring deoxyribonucleotides, ribonucleotides and nucleotide analogs, such as non-naturally occurring synthetic nucleotides or modified naturally occurring nucleotides. Nucleotide analogs are known in the art and are described e.g. in Lin et al., 1994, Nucl. Acids Res. 22:5220-5234; Jellinek et al., 1995, Biochem. 34:11363-11372; Pagratis et al., 1997, Nature Biotechnol. 15:68-73.

An "isolated" compound or composition, such as e.g. a polypeptide, antibody, nucleic acid molecule, vector, cell, or a mixture thereof, can be in particular a compound or composition which is present in a form not found in nature. Isolated compounds (e.g. polypeptides, nucleic acid molecules, antibodies, vectors, cells) or compositions include those which have been purified to an extent that they are no longer in a form in which they are found in nature.

The present invention also provides an isolated nucleic acid molecule comprising a nucleotide sequence selected from the group consisting of SEQ ID NOs: 50 to 128 and variant(s) thereof. A variant of the nucleotide sequence selected from the group consisting of SEQ ID NOs: 50 to 128 can have at least 90%, preferably at least 98%, more preferably at least 99% sequence identity to the nucleotide sequence selected from the group consisting of SEQ ID NOs: 50 to 128. A nucleotide sequence selected from the group consisting of SEQ ID NOs: 50 to 77 or a variant thereof can encode a light chain variable region (VL) or a section thereof. Alternatively, a variant of a nucleotide sequence selected from the group consisting of SEQ ID NOs: 50 to 128 can be a nucleotide sequence selected from the group consisting of SEQ ID NOs: 50 to 128, wherein not more than 12, preferably not more than 5, more preferably not more than 1 nucleotide residue(s), respectively, have been deleted, inserted or replaced by a nucleotide residue different from the replaced nucleotide residue. A nucleotide sequence selected from the group consisting of SEQ ID NOs: 78 to 126 or a variant thereof can encode a heavy chain variable region (VH) or a section thereof. The nucleotide sequence set forth in SEQ ID NO: 127 or a variant thereof can encode a light chain constant region (CL) or a section thereof. The nucleotide sequence set forth in SEQ ID NO: 128 or a variant thereof can encode a CH1-CH2-CH3 chain or a section thereof. According to an embodiment, the nucleotide sequence encoding the VL chain can be a productive IGK (Ig kappa locus) rearranged sequence (in-frame junction and no stop codon). According to an embodiment, the nucleotide sequence encoding the VH chain can be a productive IGH (Ig heavy chain gene) rearranged sequence (in-frame junction and no stop codon).

The before-mentioned variants of the nucleic acid molecules can be for example obtained by means of "parsimonious mutagenesis" (Shier, R., et al., 1996, Gene 169: 147) or by means of other methods of random or directed mutagenesis of nucleotide sequences of the present invention (Marks, J. D., et al., 1992, *J. Biol. Chem.* 267: 16007) performed in order to improve some of the properties of antibodies, as for instance the affinity, while preferably maintaining binding specificity for CD26.

The nucleic acid molecules of the present invention can be cloned in vectors suitable for their amplification, further mutagenesis or modification or expression. The present invention also provides a vector comprising a nucleotide sequence encoding for an antibody of the present invention. Preferably, the vector is capable of effectively expressing an antibody according to the present invention. In particular, a nucleic acid vector can comprise a first nucleic acid molecule covalently and operatively linked to a second nucleic acid molecule such that a host containing the vector expresses the polypeptide coded for by the first nucleic acid molecule, the first nucleic acid molecule being a nucleic acid molecule according to the present invention, in particular a nucleic acid molecule comprising a nucleotide sequence selected from the group consisting of SEQ ID NOs: 50 to 128 and variant(s) thereof. These vectors can be used for the preparation of recombinant antibodies or of chimeric proteins in a suitable host and following methods known in the art.

In accordance to a currently preferred embodiment of the present invention, the recombinant antibodies are preferably cloned and expressed in prokaryotic cells or eukaryotic host cells: particularly preferred is *E. coli*, but also other prokaryotic cells can be used, such as *B. subtilis, P. pastoris, K. lactis*, or eukaryotic cells of plant or animal origin, in particular of murine origin.

According to yet another aspect, an expression vector comprising a nucleic acid molecule of the present invention, wherein said nucleic acid molecule is operatively linked to an expression control sequence, is provided.

The term "vector" can in particular refer to a molecule, for example a nucleic acid molecule, plasmid, or virus, used to transfer coding information to a host cell. In particular, a "vector" can be a nucleic acid molecule, preferably self-replicating, which can transfer an inserted nucleic acid molecule into and/or between host cells. Examples of vectors include, but are not limited to, viral vector, wherein additional DNA segment(s) can be ligated into the viral genome, naked DNA or RNA expression vectors, DNA or RNA expression vectors encapsulated in liposomes, plasmid, such as for example a circular double stranded DNA loop into which additional DNA segment(s) can be ligated, cosmid or phage vector, a vector, which is capable of autonomous replication in a host cell into which the vector has been introduced, and DNA or RNA expression vectors associated with cationic condensing agents. In particular, a vector can be integrated into the genome of a host cell upon introduction into the host cell, what permits that it is subsequently replicated along with the host genome. In particular, the term "vector" encompasses expression vectors. As used herein, the term "expression vector" can in particular refer to a vector which is capable of directing the expression of one or more gene(s) to which the expression vector is operatively linked. Expression vectors containing nucleotide sequences as described herein can be optimised for expression in a host cell, in particular by insertion of suitable regulator regions, promoters, transcriptional terminators or activators, or replication origin.

In the context of the present application, components which are "operatively linked" can be in particular components which are in a relationship permitting the components to function in their intended manner. An expression control sequence operatively linked to a coding sequence can be in particular ligated such that expression of the coding sequence is achieved under conditions compatible with the one or more expression control sequence(s). The term "expression control sequence" encompasses, but is not limited to one or more nucleotide sequence(s) that regulate the expression of a nucleotide sequence to which the expression control sequence is operatively linked. Operatively linked expression control sequences can include, but are not limited to, expression control sequences that are contiguous with the gene of interest and expression control sequences that act in trans or at a distance for controlling a gene of interest.

According to one embodiment, an expression control sequence operatively linked to a nucleic acid sequence can control and regulate the transcription and, when appropriate, translation of the nucleic acid sequence. Expression control sequences can include, but are not limited to, one or more sequences selected from the group consisting of promoter sequences, enhancer sequences, transcription terminators, splicing signal for intron(s), if intron(s) are present, start codon, in particular in front of a protein-encoding gene, sequences ensuring a proper translation of mRNA, and stop codons. According to one embodiment, an expression vector can for example contain an origin of replication, a promoter, and optionally one or more genes which allow phenotypic selection of transformed cells.

According to yet another aspect, the present invention provides a recombinant host cell comprising a nucleic acid molecule of the present invention.

In the context of the present application, the term "host cell" can in particular refer to a cell that has been transformed, or is capable of being transformed, with a nucleic acid sequence. After having been transformed a host cell can express a selected gene of interest. The term "host cell" not only encompasses the cell obtained after transformation, but also includes the progeny of the cell obtained after transformation, whether or not the progeny is identical in morphology or in genetic make-up to the original parent cell. Because certain modifications may occur, for example due to mutation and/or environmental influences, such progeny may not be identical to the parent cell. Preferably, the progeny produces an antibody or an antibody fragment, which are capable of binding to CD26, especially human CD26. The term "host cell" can also encompass mixtures of host cells. In mixtures of host cells, the host cells may produce one antibody or one fragment thereof or two or more different antibodies or fragments thereof.

An antibody of the present invention can be an antibody produced from the hybridoma cell line deposited at CBA-ICLC of Genoa (Italy) as PD 12002 or a derivative of said hybridoma cell line. In particular, a derivative of the hybridoma cell line deposited as PD 12002 is a cell line comprising a polynucleotide comprising a sequence, which is a variant of one or more of SEQ ID NOs: 50 to 128. An antibody of the present invention can be an antibody that binds the epitope bound by an antibody produced by the hybridoma cell line deposited at CBA-ICLC of Genoa (Italy) as PD 12002. As used herein, the term "epitope" may in particular refer to a portion of an antigen capable of being recognized and specifically bound by a particular antibody. Usually, an epitope can include at least 3, and more usually, at least 4, or 8 to 10 amino acids in a particular spatial conformation. Since an antibody can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, at least 8, at least 9, at least 10, at least 15, at least 20, at least 25, or between about 5 to about 30, about 10 to about 30 or about 15 to about 35 contiguous or non-contiguous amino acids of CD26.

In one embodiment, an anti-CD26 monoclonal antibody of the present invention is capable of binding a CD26 epitope comprising one or more amino acid sequences selected from the group consisting of SEQ ID NO: 146-159. In specific embodiments the epitope can be a continuous epitope or a discontinuous epitope. In one embodiment, an anti-CD26 monoclonal antibody of the present invention is capable of binding a CD26 epitope comprising one or more amino acid sequences selected from the group consisting SEQ ID NO: 146-148, 152, 154, 158, and 159. In one embodiment, an anti-CD26 monoclonal antibody of the present invention is capable of binding a CD26 epitope comprising an amino acid sequences selected from the group consisting SEQ ID NO: 146-148, 152, 154, 158, and 159. In another embodiment, an anti-CD26 monoclonal antibody of the present invention is capable of binding a CD26 epitope comprising SEQ ID NO: 146. In a further embodiment, an anti-CD26 monoclonal antibody of the present invention is capable of binding a CD26 epitope comprising SEQ ID NO: 146 and or more amino acid sequences selected from the group consisting of SEQ ID NO: 147, 148, 152, 154, and 159. In a particular embodiment, an anti-CD26 monoclonal antibody of the present invention is capable of binding a CD26 epitope comprising SEQ ID NOs: 146, 147, and 148; or SEQ ID NOs 146, 147, and 152; or SEQ ID NOs 146 and 147; or SEQ ID NOs 146 and 152.

In one embodiment, an anti-CD26 monoclonal antibody of the present invention is capable of binding a CD26 epitope comprising one or more amino acids of SEQ ID NO: 144 or a corresponding sequence. In specific embodiments the epitope can be composed of one or more groups of continuous sequences. In one embodiment, an anti-CD26 monoclonal antibody of the present invention is capable of binding a CD26 epitope comprising one or more amino acids selected from Asp329, Asn338, Leu340, Val341, Ala342, Arg343, Asp367, Asn369, Tyr386, Gln388, Ile389, Asp390, Lys391, Lys392, Asp393, Thr395, Ser412, Leu436, Ser437, Asp438 and Tyr439 of SEQ ID NO: 144 or a corresponding sequence. In one embodiment, an anti-CD26 monoclonal antibody of the present invention is capable of binding a CD26 epitope comprising amino acids Asp329, Asn338, Leu340, Val341, Ala342, Arg343, Asp367, Asn369, Tyr386, Gln388, Ile389, Asp390, Lys391, Lys392, Asp393, Thr395, Ser412, Leu436, Ser437, Asp438 and Tyr439 of SEQ ID NO: 144 or a corresponding sequence.

In some embodiments, an anti-CD26 monoclonal antibody of the present invention is capable of binding a CD26 epitope comprising one or more amino acids selected from Asp329, Asn338, Leu340, Val341, Ala342, and Arg343 of SEQ ID NO: 144 or a corresponding sequence. In some embodiments, an anti-CD26 monoclonal antibody of the present invention is capable of binding a CD26 epitope comprising amino acids Asp329, Asn338, Leu340, Val341, Ala342, and Arg343 of SEQ ID NO: 144 or a corresponding sequence.

In some embodiments, an anti-CD26 monoclonal antibody of the present invention is capable of binding a CD26 epitope comprising amino acids Asp367 and Asn369 of SEQ ID NO: 144 or a corresponding sequence. In some embodiments, an anti-CD26 monoclonal antibody of the present invention is capable of binding a CD26 epitope comprising amino acids Tyr386, Gln388, 11e389, Asp390, Lys391, Lys392, Asp393, and Thr395 of SEQ ID NO: 144 or a corresponding sequence. In some embodiments, an anti-CD26 monoclonal antibody of the present invention is capable of binding a CD26 epitope comprising amino acid Ser412 of SEQ ID NO: 144 or a corresponding sequence. In some embodiments, an anti-CD26 monoclonal antibody of the present invention is capable of binding a CD26 epitope comprising amino acids Leu436, Ser437, Asp438 and Tyr439 of SEQ ID NO: 144 or a corresponding sequence.

According to yet another aspect, the present inventors provide an antibody produced from the hybridoma cell line deposited at CBA-ICLC of Genoa (Italy) as PD 12002 or a derivative of said hybridoma cell line.

According to another aspect, an antibody that binds the epitope bound by an antibody produced by the hybridoma cell line deposited at CBA-ICLC of Genoa (Italy) as PD 12002 is provided.

According to yet another aspect, a process of manufacturing an antibody of the present invention is provided. This process comprises the steps of:

(i) providing a host cell of the present invention, in particular the hybridoma cell line deposited at CBA-ICLC of Genoa (Italy) as PD 12002;

(ii) culturing the host cell of the present invention in a culture medium; and (iii) obtaining the antibody from the medium;

(iv) optionally purifying the antibody, for example by filtration and/or nanofiltration.

According to one embodiment, transgenic animals that have been genetically engineered to produce antibodies, in particular human antibodies, can be used to generate an antibody against an immunogenic target as mentioned in the present application, in particular an antibody to CD26. Transgenic animals and antibodies produced by these transgenic animals are obtainable using techniques known in the art, in particular using standard immunization protocols, as described e.g. in US 2010/0196266 A1. Methods for obtaining human antibodies from transgenic animals, in particular transgenic mice, are described e.g. in Green et al., Nature Genet. 7:13 (1994), Lonberg et al., Nature 368:856 (1994), and Taylor et al., Int. Immun. 6:579 (1994). A non-limiting example for a transgenic animal producing antibodies, in particular human antibodies, is a transgenic mouse, in particular the XenoMouse® from Abgenix (Fremont, Calif., USA), as described for example in Green et al., 1999, J. Immunol. Methods 231:11-23). In a transgenic animal, such as the XenoMouse®, the antibody genes of a non-human mammal subjected to genetically engineering, for example the mouse antibody genes, have been inactivated and replaced by functional human antibody genes, while the remainder of immune system of the non-human mammal subjected to genetic engineering, for example the mouse immune system, remains intact.

Human antibodies produced by transgenic animals can show therapeutic potential, while retaining the pharmacokinetic properties of normal human antibodies (Green et al., 1999, supra, US 2010/0196266 B1). The use of the XenoMouse® system has been merely exemplarily mentioned in the present application for producing antibodies. On the basis of the general knowledge in the art, a skilled person can also use another transgenic animal, in particular e.g. transgenic rodents, sheep, goats or cows, for producing antibodies of the present invention, in particular human antibodies.

Unless explicitly indicated otherwise, all before-mentioned techniques are exemplary techniques and any known method for producing antibodies or antibody fragments can be utilized. For carrying out the present invention, unless indicated otherwise, conventional techniques of cell biology, organic chemistry, biochemistry, molecular biology, cell culture, microbiology, protein chemistry, recombinant DNA, and immunology, can be employed. Such conventional techniques are for example described in: Molecular Cloning: A Laboratory Manual, $2^{nd}$ edition (Sambrook et al., Eds.), 1989; Oligonucleotide Synthesis, (M. J. Gait, Ed.), 1984; U.S. Pat. No. 4,683,195 (Mullis et al.); Nucleic Acid Hybridization, (B. D. Hames et al.), 1984; Methods in Enzymology, Volumes 154 and 155 (Wu et al.), Academic Press, New York; Transcription and Translation, (B. D. Hames and S. J. Higgins), 1984; Culture of Animal Cells (R. I. Freshney, ed.), 1987; Immobilized Cells and Enzymes, IRL Press, 1986; A Practical Guide to Molecular Cloning (B. Perbal), 1984; Gene Transfer Vectors for Mammalian Cells (J. H. Miller and M. P. Calos, Eds.), 1987; Immunochemical Methods in Cell and Molecular Biology (Mayer and Walker, eds.), 1987; Handbook of Experiment Immunology, Volumes I-IV (D. M. Weir and C. C. Blackwell, eds.), 1986; Manipulating the Mouse Embryo, 1986.

Unless otherwise required by context, singular terms shall include pluralities and plural terms shall include the singular.

According to another aspect, antibodies of the present invention are antibodies for use as a medicament. In particular, antibodies of the present invention are antibodies for use in preventing and/or treating Graft-versus-Host Disease (GvHD), preferably after haematopoietic stem cell transplantation. Furthermore, the antibodies of the present invention are antibodies for use in preventing and/or treating Aplastic Anemia, preferably Severe Aplastic Anemia. Moreover, an antibody of the present invention can be an antibody for use in promoting engraftment after haematopoietic stem cell transplantation. An antibody of the present invention can also be an antibody which is for use in preventing and/or treating Graft-versus-Host Disease (GvHD), preferably after haematopoietic stem cell transplantation, and for use in preventing and/or treating Aplastic Anemia, preferably Severe Aplastic Anemia, and for use in promoting engraftment after haematopoietic stem cell transplantation.

Graft-versus-Host Disease, Aplastic Anemia and the condition of a subject before and/or during and/or after haematopoietic stem cell transplantation are considered as being CD26 mediated disease(s), disorder(s) or condition(s), i.e. disease(s), disorder(s) or condition(s) which can be treated and/or prevented by an administration of agent(s), in particular one or more antibodies that can specifically bind to CD26, especially human CD26.

Moreover, the present invention also provides an antibody mixture of the present invention, in particular a composition, especially an isolated composition, comprising an antibody mixture of the present invention, for use as a medicament. In particular, the antibody mixture, especially the isolated composition comprising an antibody mixture of the invention, can be for use in promoting engraftment after haematopoietic stem cell transplantation, and/or for use in preventing and/or treating Graft-versus-Host disease (GvHD), preferably after haematopoietic stem cell transplantation, and/or for use in preventing and/or treating Aplastic Anemia, preferably Severe Aplastic Anemia. In particular, the antibody mixture can comprise a first antibody of the present invention, said first antibody comprising a light chain variable region comprising the sequence set forth in SEQ ID NO: 2 and/or the sequence set forth in SEQ ID NO: 3, in particular the sequence set forth in SEQ ID NO: 3, and a second antibody of the present invention, said second antibody comprising a light chain variable region comprising the sequence set forth in SEQ ID NO: 2. In one embodiment, the antibody mixture comprises or consists of the antibodies produced by the PD 12002 hybridoma deposit. Furthermore, the antibody mixture can comprise an antibody (e.g., human or humanized antibody) of the present invention comprising all 6 CDRs sequences of an antibody produced by the hybridoma cell line deposited as PD12002.

Acquired aplastic anemia (AA) is a rare bone marrow failure state characterized by marrow hypocellularity and low peripheral blood cell counts [Young N. S. et al., 1997 N Eng J Med 336:1365-1372]. Similar to other autoimmune diseases, antigen-specific T cells could be expanded from the bone marrow of AA patients and are likely to mediate organ-specific cytotoxicity to haematopoietic stem cells and progenitor cells [Nakao S. et al., *Blood* 1997, 89:3691-3699].

Differentially expressed genes, which were exclusively found in BM-infiltrating T-cells, were classified into several functional categories. These differentially expressed genes included molecules involved in immune responses as PF-4, CD26, Ncf-1, CCR2 and other chemokine receptors and ligands. Moreover, it has been supposed that AA results from auto aggressive destruction of haematopoietic stem cells and progenitors mediated by T-cells recognizing inciting target antigens [Young N. S. et al., 1997, supra]. Several groups have identified clonal T-cell expansion [Zeng W. et al., *Blood* 1999, 93(9):3008-3016; Zeng W. et al., *J Clin Invest* 2001, 108(5):765-773; Risitano A. M. et al., *Blood* 2002, 100(1):178-183], proinflammatory cytokine production [Maciejewski J. P. et al., *Blood* 1995, 85:3183-3190] and T-cell mediated cytotoxicity to CD34+ stem cells [Nakao S. et al., 1997, supra; Maciejewski J. P., Selleri C., Sato T. et al., *Br J Haematol* 1995, 91:245-252] supporting an antigen-driven T-cell response. The regulation of 483 genes also demonstrates that the bone marrow failure results from a rather complex genetic program involving chemokines, cytokines, growth factors, and their receptors. Franzke and colleagues identify the induction of several molecules playing key roles in the regulation of Th1 immune responses [Anke Franzke et al., *BMC Genomics* 2006, 7:263], such as CCR2 and CX3CR1 [Charo I. F. et al., *Microcirculation* 2003, 10(3-4):259-264; Fraticelli P. et al., *J Clin Invest* 2001, 107(9):1173-1181], which are also important in other autoimmune diseases such as multiple sclerosis [Lock C. et al., *Nat Med* 2002, 8(5):500-508; Jee Y. et al., *J Neuroimmunol* 2002, 128(1-2):49-57], and CD26, a surface-bound ectopeptidase expressed at high levels on Th1 differentiated T-cells [Dang N. H. et al., *Histol Histopathol* 2002, 17(4):1213-1226; Willheim M. et al., *J Allergy Clin Immunol* 1997, 100:348-255].

While not wishing to be bound to any theory, it is currently assumed that an antibody of the present invention capable of binding to CD26, in particular capable of specifically binding to CD26, especially to human CD26, might play a key role in the immunpathogenesis of AA and recovery of haematopoiesis after immunosuppression.

A monoclonal antibody against CD26 antigen can be therefore used for treating aplastic anemia (in particular congenital or acquired aplastic anemia), especially severe aplastic anemia.

The terms "treatment" and "prevention" as used in the present application can in particular refer to any type of treatment or prevention that imparts a benefit to a subject afflicted with a disease, a disorder or a condition or at risk of developing a disease, a disorder or a condition, in particular at least one of Graft-versus-Host disease (GvHD) and Aplastic Anemia. Moreover, the terms "treatment" and "prevention" can also refer to any type of treatment or prevention that imparts a benefit to a person with respect to engraftment after haematopoietic stem cell transplantation. The benefit imparted by the treatment or the prevention can be the benefit of providing an improvement in the condition of the subject (for example in one or more symptoms), the benefit of providing a delay in the progression of the disease, disorder or condition to be treated and/or prevented, the benefit of delaying the onset of one or more symptoms, the benefit of alleviating the disease, disorder or condition to be treated and/or prevented and/or the benefit of providing a slower progression of symptoms, etc. Moreover, the terms "treatment" and "prevention" as used in the present application are not necessarily meant to imply cure or complete abolition of symptoms.

The term "Graft-versus-Host disease" encompasses acute and/or chronic Graft-versus-Host disease, in particular Graft-versus-Host disease after haematopoietic stem cell transplantation. The term "Aplastic Anemia" encompasses both acquired and congenital aplastic anemia, as well as severe aplastic anemia.

The use of an antibody of the present invention can provide treatment and/or prevention for human subjects, in particular for medical purposes, and for animal subjects, in particular for veterinary and drug screening and development purposes. Suitable animal subjects include mammals, such as for example rabbits, primates, bovines, etc. Human subjects are the most preferred. Human subjects include neonatal, infant, juvenile and adult subjects. The terms "patient" and "subject" are used interchangeably herein. As used herein, the term "patient" may refer to humans, but is not restricted to humans.

According to another aspect, the present invention provides a pharmaceutical composition comprising at least one antibody of the present invention (for example one antibody, or two or more, or three or more antibodies of the present invention) or an antibody mixture comprising at least one antibody of the present invention or an isolated composition comprising at least one antibody of the present invention, and optionally at least one pharmaceutically acceptable excipient. In one embodiment, a pharmaceutical composition can comprise an antibody (e.g., human or humanized antibody) comprising the 6 CDRs sequences of an antibody produced by the hybridoma cell line deposited as PD 12002. In another embodiment, a pharmaceutical composition can comprise an antibody (e.g., chimeric antibody) comprising the VH and VL regions of an antibody produced by the hybridoma cell line deposited as PD 12002. In a further embodiment, a pharmaceutical composition can comprise an antibody mixture comprising a first antibody of the present invention, said first antibody comprising a light chain variable region comprising the sequence set forth in SEQ ID NO: 2 and/or the sequence set forth in SEQ ID NO: 3, in particular the sequence set forth in SEQ ID NO: 3, and a second antibody of the present invention, said second antibody comprising a light chain variable region comprising the sequence set forth in SEQ ID NO: 2. The first and the second antibody can be different antibodies, in particular the second antibody can have an amino acid sequence, wherein at least one amino acid residue has been deleted, inserted or replaced by a different amino acid residue, when compared to the amino acid sequence of the first antibody. The pharmaceutical composition can comprise the at least one antibody of the present invention, for example an antibody of the present invention or an antibody mixture, or an isolated composition of the present invention, as an effective ingredient. In particular, the pharmaceutical composition can comprise the at least one antibody of the present invention in an amount effective for treating and/or preventing at least one of Graft-versus-Host disease, preferably after haematopoietic stem cell transplantation, and Aplastic Anemia, preferably Severe Aplastic Anemia. Moreover, the pharmaceutical composition can comprise the at least one antibody of the present invention in an amount effective for promoting engraftment after haematopoietic stem cell transplantation.

The pharmaceutical composition comprising at least one antibody of the present invention is a pharmaceutical composition for use as a medicament. In particular, a pharmaceutical composition comprising at least one antibody of the present invention is a pharmaceutical composition for use in promoting engraftment after haematopoietic stem cell transplantation, and/or for use in preventing and/or treating Graft-versus-Host disease (GvHD), preferably after haematopoietic stem cell transplantation, and/or for use in treating and/or preventing Aplastic Anemia, preferably Severe Aplastic Anemia.

The pharmaceutical composition of the present invention can optionally comprise one or more excipients, preferably pharmaceutically acceptable excipients, in particular one or more diluents, preferably pharmaceutically acceptable diluents. Appropriate excipient(s), in particular pharmaceutically acceptable excipient(s), can be chosen by a skilled person on the basis of the general knowledge in the art and on the basis of the teachings provided in the present application. The diluent can be for example a pharmaceutically acceptable solvent or a pharmaceutically acceptable solvent mixture, such as for example water. Examples of suitable excipients, in particular diluents, are well known in the art and can be selected e.g. from the group comprising fluids comprising a pharmaceutically acceptable buffering system, in particular solutions comprising a pharmaceutically acceptable buffering system, for example phosphate buffered saline solutions, water, saline, in particular physiological saline, emulsions, such as oil/water emulsions, one or more wetting agents, sterile solutions, etc. A pharmaceutical composition can also contain one or more pharmaceutically acceptable carriers.

According to one embodiment, a pharmaceutical composition of the present invention can comprise at least one antibody of the present invention, such as at least one e.g. monoclonal or e.g. murine or e.g. monoclonal and murine anti-CD26 antibody according to the present invention, and water and a phosphate buffer, preferably a buffer comprising $M'H_2PO_4$ and $M''M'''HPO_4$, wherein M', M'' and M''' can be independently selected from the group consisting of Na and K. This pharmaceutical composition can optionally comprise one or more of NaCl, KCl and mixtures comprising NaCl and KCl. The at least one antibody of the present invention can comprise or consist of the antibodies produced by the PD 12002 hybridoma deposit or at least one antibody thereof. The pharmaceutical composition of the present invention can be for intravenous administration, in particular intravenous injection or intravenous infusion. In a particular embodiment, a pharmaceutical composition of the present invention can comprise or consist of the antibodies produced by the PD 12002 hybridoma deposit and DPBS.

According to one embodiment, a pharmaceutical composition of the present invention can comprise at least one antibody of the present invention, e.g. a monoclonal antibody anti CD26 according to the present invention, in particular the antibodies produced by the PD 12002 hybridoma deposit or at least one antibody thereof. In one embodiment, the pharmaceutical composition can comprise at least one antibody of the present invention, e.g. the antibodies produced by the PD 12002 hybridoma deposit or at least one antibody thereof, one or more corticosteroids, one or more antihistamines and saline, e.g. physiological saline (especially saline containing about 0.9% w/v NaCl). In particular, these aqueous pharmaceutical compositions can be administered by infusion, especially slow infusion, in particular by intravenous administration.

In one embodiment, a pharmaceutical composition of the invention comprises an antibody of the invention in a concentration range from 1 mg/ml to 10 mg/ml, 1 mg/ml to 50 mg/ml, 1 mg/ml to 100 mg/ml, 10 mg/ml to 100 mg/ml, or 50 mg/ml to 100 mg/ml, In particular embodiment, a pharmaceutical composition of the invention can comprise at least about 1 mg/ml, at least about 1 mg/ml, at least about 5 mg/ml, at least about 10 mg/ml, at least about 20 mg/ml, at least about 30 mg/ml, at least about 40 mg/ml, at least about 50 mg/ml, or at least about 100 mg/ml of an antibody of the invention.

In one embodiment, pharmaceutical compositions can comprise the at least one antibody of the present invention in amount between 1 mg of said at least one antibody/$m^2$ body surface area per day and 4.5 mg of said at least one antibody/$m^2$ body surface area per day for use in the treatment and/or prevention of Graft-versus-Host disease or can comprise at least one antibody of the present invention in an amount between 1 mg of said at least one antibody/$m^2$ body surface area per day and 2 mg of said at least one antibody/$m^2$ body surface area per day for use in the treatment and/or prevention of Aplastic Anemia. Moreover, according to one embodiment the pharmaceutical compositions can comprise currently preferred ranges of amounts and amounts of at least one antibody of the present invention as discussed herein.

The term “pharmaceutically acceptable” as used herein can in particular indicate that the “pharmaceutically acceptable” compound or “pharmaceutically acceptable” composition is suitable for administration to a subject to achieve a treatment and/or prevention of a disease, of a disorder or of a condition, in particular of at least one of Graft-versus-Host disease and Aplastic Anemia or to achieve promoting of engraftment after haematopoietic stem cell transplantation, without unduly deleterious side effects in light of the severity of the disease and necessity of the treatment.

The term “effective amount” as used herein can in particular indicate an amount of the at least one antibody of the present invention, for example of an antibody or of an antibody mixture, sufficient to produce a desirable effect upon a patient inflicted with a disease, disorder or a condition, in particular at least one of Graft-versus-Host disease and Aplastic Anemia, or to produce a desirable effect upon a patient with respect to engraftment after haematopoietic stem cell transplantation, including improvement in the condition of the patient (e.g., in one or more symptoms), delay in the progression of the disease, etc. An effective amount of an antibody described herein can in particular be an amount sufficient to ameliorate, reverse, stabilize, slow and/or delay progression of Graft-versus-Host disease and/or Aplastic Anemia. As known in the art, an effective amount of, for example, an antibody according to the present invention can vary, depending on, inter alia, patient history, administration for prevention or treatment purposes, target indication (Graft-versus-Host disease, Aplastic Anemia, etc.), as well as other factors, such as the type (and/or dosage) of antibody.

A pharmaceutical composition of the present invention can be in solid or liquid form and can be, inter alia, in a form of one or more powder(s), one or more tablet(s), one or more fluids, in particular one or more solution(s), or one or more aerosol(s). A pharmaceutical composition of the invention can also comprise one or more further biologically active agent(s), such as for example active agent(s) for use in the treatment and/or prevention of at least one of Graft-versus-Host disease and Aplastic Anemia or active agent(s) for promoting engraftment after haematopoietic stem cell transplantation. The administration of a pharmaceutical composition of the present invention can be for example an administration selected from the group consisting of intraperitoneal, intravenous, parenteral, intrarenal, subcutaneous, topical, intrabronchial, intrapulmonary and intranasal administration and, if desired for local treatment, intralesional administration. A parenteral administration can be for example an intraperitoneal, intradermal, intramuscular, subcutaneous, intravenous or intraarterial, administration. The compositions of the invention can also be administered directly to the target site, e.g., by biolistic delivery to the target site, like a specific organ afflicted with a disease, disorder or condition, in particular Graft-versus-Host disease.

In particular, said administration can be carried out by injection and/or infusion and/or delivery, such as e.g. intravenous or intraperitoneal injection or infusion. The pharmaceutical composition can be present in the form of an injectable dosage form or a dosage form for administration by infusion, in particular in the form of an injectable dosage form for intravenous or intraperitoneal injection or an infusion dosage form for intravenous or intraperitoneal administration.

A pharmaceutical composition, in particular a pharmaceutical composition in the form of an injectable dosage form, can comprise one or more pharmaceutically acceptable solvents, such as for example water, and/or can be in the form of a fluid, for example in the form of a suspension, emulsion or solution.

A pharmaceutical composition according to the present invention can also comprise preservatives and other additives, such as for example preservatives and other additives selected from the group consisting of antimicrobials, antioxidants, chelating agents, active agent(s) for use in the treatment and/or prevention of at least one of Graft-versus-Host disease and Aplastic Anemia or active agent(s) for promoting engraftment after haematopoietic stem cell transplantation and inert gases and the like, and/or proteinaceous carriers, such as e.g. serum albumin or immunoglobulin, in particular of human origin.

A pharmaceutical composition according to the present invention can be administered to the subject at a suitable dose. The dosage regimen can be for example determined by an attending physician. As well known in the art, dosages for a patient can depend upon many factors, such as the patient's size, body surface area, age, weight, administration for prevention or treatment purposes, target indication (Graft-versus-Host disease, Aplastic Anemia, etc.), the particular compound to be administered, general health, and other drugs being administered concurrently. According to one embodiment, at least one antibody of the present invention (e.g. one or two or three or more antibodies of the present invention), in particular for use in the treatment and/or prevention of Graft-versus-Host disease, can be administered to a patient in an amount between 1 mg of said at least one antibody/$m^2$ body surface area per day and 4.5 mg of said at least one antibody/$m^2$ body surface area per day, in particular in an amount between 2 mg of said at least one antibody/$m^2$ body surface area per day and 4.5 mg of said at least one antibody/$m^2$ body surface area per day. In particular, an amount of about 2 mg of said at least one antibody/$m^2$ body surface area per day or an amount of about 3 mg of said at least one antibody/$m^2$ body surface area per day or an amount of about 4.5 mg of said at least one antibody/$m^2$ body surface area per day can be administered to a patient. The at least one antibody of the present invention may be present in the above-mentioned amounts in a pharmaceutical composition. As used herein, the term "at least one antibody" encompasses one antibody or two or more (e.g. three or more) antibodies.

According to one embodiment, a pharmaceutical composition of the present invention can be a pharmaceutical composition which comprises an antibody mixture produced by hybridoma cell line deposit PD 12002, and optionally at least one pharmaceutically acceptable excipient.

The pharmaceutical composition can—according to one embodiment—comprise the antibodies produced by hybridoma cell line deposit PD 12002, in particular for use in the treatment and/or prevention of Graft-versus-Host disease for administration to a patient in an amount between 1 mg of said antibody mixture (produced by hybridoma cell line deposit PD 12002)/$m^2$ body surface area per day and 4.5 mg of said antibody mixture (produced by hybridoma cell line deposit PD 12002)/$m^2$ body surface area per day, in particular in an amount between 2 mg of said antibody mixture (produced by hybridoma cell line deposit PD 12002)/$m^2$ body surface area per day and 4.5 mg of said antibody mixture (produced by hybridoma cell line deposit PD 12002)/$m^2$ body surface area per day. According to one embodiment, an amount of about 2 mg of said antibody mixture/$m^2$ body surface area per day or an amount of about 3 mg of said antibody mixture/$m^2$ body surface area per day or an amount of about 4.5 mg of said antibody mixture/$m^2$ body surface area per day can be administered to a patient. The amounts of: 2, 3, or 4.5 mg of antibody mixture produced by hybridoma cell line deposit PD 12002/$m^2$ body surface area per day being successfully used in a clinical setting. According to a further embodiment, a pharmaceutical composition for administration to patients comprises the antibody in an amount between 0.1 and 10 mg/$m^2$ body surface area per day.

According to one embodiment, the administration of pharmaceutical compositions of the present invention is intravenous administration, e.g. intravenous infusion or intravenous injection. Optionally additionally at least one immunosuppressive drug, e.g. at least one immunosuppressive drug selected from the group consisting of corticosteroids, and cyclosporine (in particular cyclosporine A) can be administered to the patient, together with the antibody or separately.

Body surface area (BSA) can be calculated according to any known method. For example, the body surface area (BSA) of a patient can be calculated according to the Mosteller formula of BSA ($m^2$)=([Height (cm)×Weight (kg)]/3600)$^{1/2}$ (Mosteller R D., N Engl J Med 1987 Oct. 22; 317(17):1098, which is incorporated herewith by reference) or according to the DuBois and DuBois formula of BSA ($m^2$)=0.20247×Height (m)$^{0.725}$×Weight (kg)$^{0.425}$ (DuBois D; DuBois E F., Arch Int Med 1916 17:863-71, which is incorporated herewith by reference). According to a preferred embodiment, the Mosteller formula is used for calculating the body surface area (BSA) of a patient.

A pharmaceutical composition for use in the treatment of Aplastic Anemia can comprise at least one antibody of the present invention, and optionally at least one pharmaceutically acceptable excipient. Said at least one antibody (e.g. one or two or more antibodies) of the present invention can be administered to a patient in an amount between 1 mg of said at least one antibody/$m^2$ body surface area per day and 2 mg of said at least one antibody/$m^2$ body surface area per day, in particular in an amount of about 2 mg of said at least one antibody/$m^2$ body surface area per day for use in the treatment of Aplastic Anemia. The at least one antibody of the present invention can be present in a pharmaceutical composition in the above-mentioned amounts or ranges of amounts. In particular, the pharmaceutical compositions can be administered by intravenous administration, e.g. infusion or injection. Optionally, additionally at least one immunosuppressive drug, in particular cyclosporine A, can be administered to the patient, together with the at least one antibody or separately. According to one embodiment, the pharmaceutical composition for use in the treatment of Aplastic Anemia can comprise an antibody mixture produced by hybridoma cell line deposit PD 12002, and optionally at least one pharmaceutically acceptable excipient.

According to one embodiment, an antibody mixture produced by hybridoma cell line deposit PD 12002 can be administered for use in the treatment of Aplastic Anemia to a patient in an amount between 1 mg of said antibody mixture (produced by hybridoma cell line deposit PD 12002)/m$^2$ body surface area per day and 2 mg of said antibody mixture (produced by hybridoma cell line deposit PD 12002)/m$^2$ body surface area per day, in particular in an amount of about 2 mg of said antibody mixture (produced by hybridoma cell line deposit PD 12002)/m$^2$ body surface area per day.

Moreover, doses of an antibody of the present invention below or above the above indicated exemplary ranges can be administered, e.g. for treating and/or preventing at least one of Graft-versus-Host disease and Aplastic Anemia or for promoting engraftment after hematopoietic stem cell transplantation, especially considering the aforementioned factors. A pharmaceutical composition of the present invention can be formulated to be short-acting, fast-releasing, long-acting, or sustained-releasing.

Furthermore, a pharmaceutical composition of the present invention can comprise further biologically active agents, depending on the intended use of the pharmaceutical composition.

The pharmaceutical composition of the present invention can further comprise at least one immunosuppressive drug, in particular an effective amount of at least one immunosuppressive drug. The immunosuppressive drug can be for example at least one drug selected from the group consisting of corticosteroids, in particular 6-methylprednisolone, and cyclosporine, in particular cyclosporine A. Moreover, the pharmaceutical composition can comprise a combination of therapies where the second active ingredient is not included in the same composition as the anti-CD26 antibody.

In one embodiment, the pharmaceutical composition of the present invention (e.g. for treating and/or preventing at least one of Graft-versus-Host disease and Aplastic Anemia or for promoting engraftment after hematopoietic stem cell transplantation) comprising at least one antibody of the present invention, in particular an antibody mixture of the present invention, can comprise one or more corticosteroids, one or more antihistamines, water and sodium chloride. In particular, the pharmaceutical composition can further comprise one or more corticosteroids, one or more antihistamines and saline, e.g. physiological saline (especially saline containing about 0.9% w/v NaCl). In particular, these aqueous pharmaceutical compositions can be administered by infusion, especially slow infusion, in particular by intravenous administration. The at least one antibody of the present invention, in particular the antibodies produced by hybridoma cell line deposit PD 12002, one or more corticosteroids, and one or more antihistamines, each alone or in combination, can be preferably present in a therapeutically effective amount. In particular, the pharmaceutical composition can comprise the at least one antibody of the present invention in amount between 1 mg of said at least one antibody/m$^2$ body surface area per day and 4.5 mg of said at least one antibody/m$^2$ body surface area per day for use in the treatment and/or prevention of Graft-versus-Host disease or can comprise for use in the treatment and/or prevention of Aplastic Anemia at least one antibody of the present invention in an amount between 1 mg of said at least one antibody/m$^2$ body surface area per day and 2 mg of said at least one antibody/m$^2$ body surface area per day. Moreover, the pharmaceutical composition can comprise currently preferred ranges of amounts and amounts of at least one antibody of the present invention, in particular the antibody mixture as discussed herein. Moreover, the pharmaceutical composition can comprise a combination of therapies where the second active ingredient is not included in the same composition as the anti-CD26 antibody.

Corticosteroids are well known in the art and can comprise in particular mineralocorticoids and glucocorticoids. Glucocorticoids can be anti-inflammatory agents. As used herein, the term corticosteroids can include steroids which can be in particular produced in the adrenal cortex of vertebrates, as well as can encompass synthetic corticosteroids or synthetic or natural corticosteroid analogs, including compounds that mimic the activity of natural steroid hormones, such as e.g. cortisone and hydrocortisone. Corticosteroid analogs may in particular encompass synthetic or natural chemical compounds which resemble in structure and/or function any of naturally occurring steroids elaborated by the adrenal cortex.

One or more corticosteroids can be selected from the group consisting of alclometasone dipropionate, amcinonide, amcinafel, amcinafide, beclamethasone, betamethasone, betamethasone dipropionate, betamethasone valerate, clobetasone propionate, chloroprednisone, clocortelone, cortisol, cortisone, cortodoxone, difluorosone diacetate, descinolone, desonide, defluprednate, dihydroxycortisone, desoximetasone, dexamethasone, deflazacort, diflorasone, diflorasone diacetate, dichlorisone, esters of betamethasone, fluazacort, flucetonide, flucloronide, fludrotisone, fluorocortisone, flumethasone, flunisolide, fluocinonide, fluocinolone, fluocinolone acetonide, flucortolone, fluperolone, fluprednisolone, fluroandrenolone acetonide, fluocinolone acetonide, flurandrenolide, fluorametholone, fluticasone propionate, hydrocortisone, hydrocortisone butyrate, hydrocortisone valerate, hydrocortamate, loteprendol, medrysone, meprednisone, methylprednisone, methylprednisolone, 6-methylprednisolone, mometasone furoate, paramethasone, paramethasone acetate, prednisone, prednisolone, prednidone, prednicarbate, triamcinolone acetonide, triamcinolone hexacatonide, tixocortol prednisolone, and triamcinolone, pharmaceutically acceptable salts thereof, derivatives thereof, and mixtures thereof.

Antihistamines are known in the art and can be in particular pharmaceutical drugs that can reduce or counteract the action of histamine. In particular, an antihistamine can be a $H_1$-receptor antagonist.

One or more antihistamine drugs can be in particular selected from the group consisting of astemizole, azelastine, buclizine, brompheniramine, chlorpheniramine, cetirizine, clemastine, cyclizine, desloratidine, dexbrompheniramine, diphenhydramine, doxylamine, ebastine, emedastine, epinastine, fexofenadine, hydroxyzine, ketotifen, levocabastine, levocetirizine, loratidine, mequitazine, mizolastine, olopatadine, oxatomide, phenindamine, pheniramine, pyrilamine, terfenidine, triprolidine, pharmaceutically acceptable salts, isomers or prodrugs thereof.

According to another aspect, the present invention provides a kit comprising: (i) at least one antibody of the present invention, in particular an antibody mixture of the invention or a composition comprising an antibody mixture of the present invention; and additionally (ii) a) at least one immunosuppressive drug, e.g. at least one immunosuppressive drug selected from the group consisting of corticosteroids, and cyclosporine, in particular cyclosporine A or b) at least one corticosteroid and at least one antihistamine. The at least one antibody can comprise or consist of the antibodies produced by hybridoma cell line deposit PD 12002. In particular, the kit can comprise the at least one antibody of the present invention in amount between 1 mg of said at least one antibody/$m^2$ body surface area per day and 4.5 mg of said at least one antibody/$m^2$ body surface area per day for use in the treatment and/or prevention of Graft-versus-Host disease or can comprise for use in the treatment and/or prevention of Aplastic Anemia at least one antibody of the present invention in an amount between 1 mg of said at least one antibody/$m^2$ body surface area per day and 2 mg of said at least one antibody/$m^2$ body surface area per day. Moreover, the pharmaceutical composition can comprise currently preferred ranges of amounts and amounts of at least one antibody of the present invention as discussed herein.

The kit can be a kit for use as a medicament, in particular a kit for preventing and/or treating Graft-versus-Host disease (GvHD), preferably after haematopoietic stem cell transplantation, and/or a kit for use in treating Aplastic Anemia, preferably Severe Aplastic Anemia, and/or a kit for promoting engraftment after haematopoietic stem cell transplantation. The terms kit of parts and kit are used interchangeably herein.

In vivo and in vitro production of antibodies of the invention in transgenic animals, obtained by genetic manipulation of non-human animals, in particular non-human mammals, using at least one of the nucleotide sequences described in the present invention by methods known to a skilled person, is also comprised within the scope of the present invention.

In the following, the present invention will be described in more detail with reference to the following non-limiting examples. It is, however, understood that the present invention is not limited to the following examples.

EXAMPLES

Example 1

Determining the Nucleotide Sequences

This process can be summarized into three phases:

Phase I—Cloning of Genes Encoding for Antibody Chains

- Extraction of total RNA from Hybridoma cells producing CDina26 (Hybridoma cell line deposit under the reference PD 12002, see above);
- Reverse transcription;
- Amplification of the gene of interest using specific oligonucleotides as primers;
- Cloning of gene using a prokaryotic vector;
- Bacterial transformation;
- Control of cloning procedure, selecting suitable transformed clones.

Phase II—Sequencing of Genes Encoding for Antibody Variable Chains and Bioinformatics Analysis:

- Picking and sequencing of 100 colonies for both VH and VL chains;
- Bioinformatics analysis of sequences;
- Generation of a consensus sequence, if required, for the VL and VH chains and indication of the consensus sequence differing bases and their percentage.

Phase III—Sequencing of Genes Encoding for Antibody Constant Chains:

- Sequencing of the corresponding CL chain for VL chain;
- Sequencing of corresponding CH1-CH2-CH3 chain for VH chain.

The results show the presence in mRNA samples of three groups of VL chain sequences (VL group 1, VL group 2 and VL group 3) and two groups of VH chain sequences (VH group 1 and VH group 2).

Determining the Amino Acid Sequence

Mass spectrometry analysis and N-terminal sequencing were used to confirm the amino acid sequence present in CDina26 sample. In CDina26 sample was confirmed the presence of VL group 1 and its related CL sequence, of VL group 3 chain and of VH group 1 related to its CH1-CH2-CH3 chain. Neither VL Sequences group 2 nor VH sequences group 2 have been detected as aminoacidic sequences in the CDina26 antibody sample.

Example 2

CDina26 Binding to Human and Porcine CD26

The binding of CDina26 to human CD26 has been compared to its binding to minipig CD26 by Biacore® assay and multiparametric flow cytometry. CDina26 is not able to recognize Porcine Antigen neither as soluble protein or as a transmembrane protein expressed on T lymphocytes.

1. Flow cytometry analysis was utilized to determine the ability of CDina26 to bind to cell surface expressed CD26.
   - Lymphocytes were isolated from human or minipig peripheral blood samples by centrifugation on gradient density. The Binding of CDina26 to human T Lymphocytes was analyzed by multiparametric flow cytometry.
   - More than 45% of Human T lymphocytes expressing CD3 marker bind to CDina26. On the contrary only 2% of porcine T lymphocytes expressing CD3 marker bind to CDina26. This may be seen from FIG. 9.
2. Binding of CDina26 to either Human or Porcine Antigen (purchased from Sigma CAT #D4943 and D 7052) was analysed by Biacore®.
   - CDina26 was captured on the matrix by a polyclonal anti-mouse Ig antibody previously immobilized on a flow cell of Biacore® T100 sensor chip. Either Human or Porcine Antigen were injected in solution over the immobilized CDina26.
   - Human antigen, injected at two concentrations over immobilized CDina26, gave a dose dependent response with a high affinity binding, indicated by a kinetic dissociation rate of $2.8\times10^{-5}$ $s^{-1}$.
   - Porcine antigen, injected over immobilized CDina26, gave no binding.

FIG. 11 shows binding of Human (left) and Porcine (right) Antigen (Ag) on captured CDina26, measured in Biacore® Resonance Units (RU).

Example 3

Antibody Production

CDina26 is produced by hybridoma cell line deposit at CBA-ICLC of Genoa (Italy) under reference PD 12002. The hybridomas may be cultured in serum free medium. CDina26 comprises a mixture of murine antibodies. In particular, CDina26 comprises a murine, monoclonal antibody, which is of IgG 2B class and specifically binds to human CD26.

A pharmaceutical composition comprising CDina26 is present in the form of a clear colourless solution containing CDina26, which solution can be used for intravenous infusion (e.g. 1 mg of CDina26/1 ml of solution; the solution can be contained in a vial).

Example 4

Pharmacodynamic Study In Vitro

In vitro pharmacodynamics studies were performed for the characterization of murine monoclonal antibody against CD26, in particular for the characterization of the antibodies produced by PD 12002 hybridoma cell line deposit, referred to herein as CDina26.

The aim of these studies was to evaluate the expression of and specific binding to CD26 on the surface of cell population involved in the immune response, in particular:

- T lymphocytes
- B lymphocytes
- NK (natural killer) cells
- Monocytes
- Dendritic cells Example 4a CDina26 antigen expression was evaluated in resting T, B and NK cells ($T_0$) purified from 5 healthy donors (corresponding to "ESP.1" to "ESP.5" in Table 1) and then in cells activated via allogeneic stimuli (mixed lymphocyte culture (MLC)), mitogeneic stimuli (phytohemagglutinin (PHA)) or antigenic stimuli (*Candida albicans*).

In the present application, the abbreviation MFIR is used as abbreviation for mean Relative Fluorescence Intensity as known in the art.

TABLE 1

Evaluation of percentage of CDina26 + cells and MFIR index within lymphocyte subpopulations in healthy donors before and after mitogenic stimuli with PHA.

| | % CD26 | | MFIR | |
|---|---|---|---|---|
| ESP. 1 PHA subpopulations | | | | |
| T CD3+/CD4+ | 86→84 | D | 5→ 3 | D |
| T CD3+/CD8+ | 75→67 | D | 6→14 | A |
| T CD3+/CD16+ | 16→61 | A | 1→ 6 | A |
| T CD3+/CD56+ | 36→68 | A | 4→7 | A |
| NK CD3−/CD16+ | 11→58 | A | 0→1 | A |
| NK CD3−/CD56+ | 10→32 | A | 0→1 | A |
| B CD19+/CD20+ | 13→80 | A | 2→10 | A |
| ESP. 2 PHA subpopulations | | | | |
| T CD3+/CD4+ | 74→91 | A | 10→ 9 | D |
| T CD3+/CD8+ | 57→93 | A | 15→15 | |
| T CD3+/CD16+ | 16→85 | A | 2→6 | A |
| T CD3+/CD56+ | 38→97 | A | 6→18 | A |
| NK CD3−/CD16+ | 15→50 | A | 2→1 | D |
| NK CD3−/CD56+ | 10→38 | A | 1→1 | |
| B CD19+/CD20+ | 11→95 | A | 2→11 | A |
| ESP. 3 PHA subpopulations | | | | |
| T CD3+/CD4+ | 75→82 | A | 8→7 | D |
| T CD3+/CD8+ | 45→82 | A | 4→9 | A |
| T CD3+/CD16+ | 15→69 | A | 1→6 | A |
| T CD3+/CD56+ | 41→92 | A | 4→9 | A |
| NK CD3−/CD16+ | 7→14 | A | 1→2 | A |

TABLE 1-continued

Evaluation of percentage of CDina26 + cells and MFIR index within lymphocyte subpopulations in healthy donors before and after mitogenic stimuli with PHA.

| | % CD26 | | MFIR | |
|---|---|---|---|---|
| NK CD3−/CD56+ | 6→25 | A | 1→3 | A |
| B CD19+/CD20+ | 14→92 | A | 8→10 | A |
| ESP. 4 PHA subpopulations | | | | |
| T CD3+/CD4+ | 81→83 | A | 3→10 | A |
| T CD3+/CD8+ | 53→91 | A | 2→13 | A |
| T CD3+/CD16+ | 23→96 | A | 1→18 | A |
| T CD3+/CD56+ | 52→94 | A | 3→14 | A |
| NK CD3−/CD16+ | 23→67 | A | 1→6 | A |
| NK CD3−/CD56+ | 14→45 | A | 0→4 | A |
| B CD19+/CD20+ | 12→92 | A | 0→14 | A |
| ESP. 5 PHA subpopulations | | | | |
| T CD3+/CD4+ | 74→92 | A | 30→10 | D |
| T CD3+/CD8+ | 48→92 | A | 11→12 | A |
| T CD3+/CD16+ | 9→81 | A | 2→13 | A |
| T CD3+/CD56+ | 15→91 | A | 14→11 | D |
| NK CD3−/CD16+ | 8→12 | A | 2→5 | A |
| NK CD3−/CD56+ | 3→20 | A | 2→3 | A |
| B CD19+/CD20+ | 3→90 | A | 2→10 | A |

In the columns entitled "% CD26" and "MFIR", respectively, the first value corresponds to T0, the second value after the arrow corresponds to the stimulated cells:
A, increase in value or a percentage of expression (MFIR)
D, decrease in value or a percentage of expression (MFIR)
T0 being an abbreviation for Time 0, i.e. for the point in time preceding the cell stimulation.

As may be seen from Table 1, CD26 expression on activated lymphocytes showed an increased percentage of CD26+ cells after stimulation with PHA as compared to $T_0$ with the exception of T CD3+CD4+ and T CD3+CD8+ in experiment number 1 ("ESP 1"). Level of expression (MFRI index value) varied among the different T, B and NK subpopulations and the 5 healthy volunteers. Furthermore, mitogeneic stimuli appears to modestly increase the values of MFIR (Table 1).

Example 4b

The analysis of the results reported in Table 2 showed that in all subsets analyzed, with the exception of CD3+ CD4+ T subpopulations of all healthy volunteers, there is an increase in the percentage of lymphocytes expressing CDina26 antigen after antigenic stimuli.

In all experiments, except one ("ESP. 5"), there is an increase of MFIR values. It may be also noted that the increase of MFIR values as compared with time 0 is greater in cultures stimulated with *Candida* than those stimulated with PHA. The Candida antigen stimulation significantly increases the expression of CD26 molecule on the cell membrane, especially in subpopulations T CD3+ CD16+ and T CD56+ CD3+.

TABLE 2

Evaluation of percentage of CDina26 + cells and MFIR index within lymphocyte subpopulations in healthy donors before and after antigenic stimuli with *Candida albicans*.

| | % CD26 | | MFIR | |
|---|---|---|---|---|
| ESP. 1 *Candida* subpopulations | | | | |
| T CD3+/CD4+ | 86→71 | D | 5→ 8 | A |
| T CD3+/CD8+ | 75→80 | A | 6→14 | A |

TABLE 2-continued

Evaluation of percentage of CDina26 + cells and MFIR index within lymphocyte subpopulations in healthy donors before and after antigenic stimuli with *Candida albicans*.

| | % CD26 | | MFIR | |
|---|---|---|---|---|
| T CD3+/CD16+ | 16→46 | A | 1→16 | A |
| T CD3+/CD56+ | 36→68 | A | 4→13 | A |
| NK CD3−/CD16+ | 11→11 | | 0→4 | A |
| NK CD3−/CD56+ | 10→32 | A | 0→4 | A |
| B CD19+/CD20+ | 13→21 | A | 2→3 | A |
| ESP. 2 *Candida* subpopulations | | | | |
| T CD3+/CD4+ | 74→64 | D | 10→11 | A |
| T CD3+/CD8+ | 57→78 | A | 15→29 | A |
| T CD3+/CD16+ | 16→98 | A | 2→36 | A |
| T CD3+/CD56+ | 38→99 | A | 6→38 | A |
| NK CD3−/CD16+ | 15→97 | A | 2→23 | A |
| NK CD3−/CD56+ | 10→91 | A | 1→19 | A |
| B CD19+/CD20+ | 11→26 | A | 2→5 | A |
| ESP. 3 *Candida* subpopulations | | | | |
| T CD3+/CD4+ | 75→60 | D | 8→14 | A |
| T CD3+/CD8+ | 45→59 | A | 4→15 | A |
| T CD3+/CD16+ | 15→30 | A | 1→89 | A |
| T CD3+/CD56+ | 41→71 | A | 4→85 | A |
| NK CD3−/CD16+ | 7→26 | A | 1→9 | A |
| NK CD3−/CD56+ | 6→19 | A | 1→7 | A |
| B CD19+/CD20+ | 14→14 | | 8→5 | D |
| ESP. 4 *Candida* subpopulations | | | | |
| T CD3+/CD4+ | 81→81 | | 3→22 | A |
| T CD3+/CD8+ | 53→65 | A | 2→24 | A |
| T CD3+/CD16+ | 23→90 | A | 1→76 | A |
| T CD3+/CD56+ | 52→94 | A | 3→79 | A |
| NK CD3−/CD16+ | 23→79 | A | 1→46 | A |
| NK CD3−/CD56+ | 14→88 | A | 0→58 | A |
| B CD19+/CD20+ | 12→15 | A | 0→6 | A |
| ESP. 5 *Candida* subpopulations | | | | |
| T CD3+/CD4+ | 74→4 | D | 30→9 | D |
| T CD3+/CD8+ | 48→65 | A | 11→20 | A |
| T CD3+/CD16+ | 9→87 | A | 2→39 | A |
| T CD3+/CD56+ | 15→94 | A | 14→41 | A |
| NK CD3−/CD16+ | 8→91 | A | 2→34 | A |
| NK CD3−/CD56+ | 3→87 | A | 2→30 | A |
| B CD19+/CD20+ | 3→ 6 | A | 2→11 | A |

In the columns entitled "% CD26" and "MFIR", respectively, the first value corresponds to T0, the second value after the arrow corresponds to the stimulated cells:

A, increase in value or a percentage of expression (MFIR)

D, decrease in value or a percentage of expression (MFIR)

Example 4c

Table 3 shows that in all experiments, the percentage of lymphocytes positive for CDina26 antigen increased in all lymphocyte subpopulations present after stimulation with mixed lymphocyte culture with the exception of CD3+ CD4+ T subpopulation.

TABLE 3

Evaluation of percentage of CDina26 + cells and MFIR index within lymphocyte subpopulations in healthy donors before and after allogeneic stimuli with MLC (mixed lymphocyte culture).

| | % CD26 | | MFIR | |
|---|---|---|---|---|
| ESP. 1 MLC subpopulations | | | | |
| T CD3+/CD4+ | 86→67 | D | 5→6 | A |
| T CD3+/CD8+ | 70→75 | A | 6→8 | A |
| T CD3+/CD16+ | 16→83 | A | 1→9 | A |
| T CD3+/CD56+ | 36→89 | A | 4→11 | A |
| NK CD3−/CD16+ | 11→74 | A | 0→5 | A |
| NK CD3−/CD56+ | 10→70 | A | 0→5 | A |
| B CD19+/CD20+ | 13→19 | A | 2→3 | A |
| ESP. 2 MLC subpopulations | | | | |
| T CD3+/CD4+ | 74→63 | D | 10→10 | |
| T CD3+/CD8+ | 57→75 | A | 15→18 | A |
| T CD3+/CD16+ | 16→86 | A | 2→19 | A |
| T CD3+/CD56+ | 38→95 | A | 6→18 | A |
| NK CD3−/CD16+ | 15→17 | A | 2→11 | A |
| NK CD3−/CD56+ | 10→84 | A | 1→9 | A |
| B CD19+/CD20+ | 11→11 | | 2→2 | |
| ESP. 3 MLC subpopulations | | | | |
| T CD3+/CD4+ | 75→57 | D | 8→18 | A |
| T CD3+/CD8+ | 45→53 | A | 4→25 | A |
| T CD3+/CD16+ | 15→48 | A | 1→67 | A |
| T CD3+/CD56+ | 41→77 | A | 4→166 | A |
| NK CD3−/CD16+ | 7→51 | A | 1→13 | A |
| NK CD3−/CD56+ | 6→47 | A | 1→13 | A |
| B CD19+/CD20+ | 14→25 | A | 8→22 | A |
| ESP. 4 MLC subpopulations | | | | |
| T CD3+/CD4+ | 81→76 | D | 3→12 | A |
| T CD3+/CD8+ | 53→78 | A | 2→18 | A |
| T CD3+/CD16+ | 23→83 | A | 1→16 | A |
| T CD3+/CD56+ | 52→89 | A | 3→18 | A |
| NK CD3−/CD16+ | 23→87 | A | 1→10 | A |
| NK CD3−/CD56+ | 14→79 | A | 0→11 | A |
| B CD19+/CD20+ | 12→27 | A | 0→6 | A |
| ESP. 5 MLC subpopulations | | | | |
| T CD3+/CD4+ | 74→62 | D | 30→11 | D |
| T CD3+/CD8+ | 48→68 | A | 11→13 | A |
| T CD3+/CD16+ | 9 →85 | A | 2 →19 | A |
| T CD3+/CD56+ | 15→93 | A | 14→24 | A |
| NK CD3−/CD16+ | 8 →85 | A | 2 →13 | A |
| NK CD3−/CD56+ | 3 →85 | A | 2 →15 | A |
| B CD19+/CD20+ | 3 →28 | A | 2 →11 | A |

In the columns entitled "% CD26" and "MFIR", respectively, the first value corresponds to T0, the second value after the arrow corresponds to the stimulated cells:

A, increase in value or a percentage of expression (MFIR)

D, decrease in value or a percentage of expression (MFIR)

The MFIR index increased after stimulation as compared with time 0 in all subsets and all experiments, with the exception of the subpopulation of CD4+ CD3+ T in experiments number 2 ("ESP.2") and number 5 ("ESP.5").

Similar to the stimulation with Candida, the allogeneic stimulation constantly increases the expression of CDina26 antigen and MFIR index on most lymphocyte subpopulations. A significant increase was observed mainly in subpopulations of CD16+ CD3+ T and CD56+ CD3+ T experiment number 3 ("ESP.3").

Example 4d

Finally, the expression of CDina26 antigen was investigated on leukocyte subpopulations in patients after allo-HSCT. In particular, two patients were assessed during the early tests for monitoring immune reconstitution post-transplant, while four patients who developed acute GvHD, it was possible to carry out the assessment both during the onset of GvHD and after the resolution. Compared with controls, patients showed a highly variable distribution of T, NK and B subpopulations (Table 4), which is compatible with the process of haematopoietic reconstitution that occurs in the months following transplantation.

TABLE 4

Distribution (measured as %) of lymphocyte subpopulations in 6 patients who underwent HSCT evaluated at the time of immune reconstitution and compared with the range obtained by evaluating 5 healthy donors.

| | Percentage (%) | | | | | | |
|---|---|---|---|---|---|---|---|
| | Healthy donors | Patients | | | | | |
| Subpopulation | range | CK | IP | BGL* | BG* | CJ* | DF* |
| T CD3+/CD4+ | 44-58 | 6 | 12 | 22 | 6 | 7 | 12 |
| T CD3+/CD8+ | 20-30 | 69 | 40 | 42 | 50 | 7 | 10 |
| T CD3+/CD16+ | 5-10 | 3 | 4 | 17 | 9 | 4 | 10 |
| T CD3+/CD56+ | 4-10 | 2 | 10 | 11 | 2 | 2 | 13 |
| NK CD3−/CD16+ | 2-9 | 14 | 18 | 13 | 8 | 52 | 34 |
| NK CD3−/CD56+ | 7-15 | 18 | 17 | 1 | 8 | 67 | 67 |
| B CD20+/CD19+ | 3-7 | 0 | 7 | 0 | 1 | 0 | 5 |

*At the time of evaluation, the patients had developed acute GvHD grade II.

Analyzing the percentage of CD26 (Table 5) in all patients there was an increase of the expression of this molecule within subpopulations T CD16+ CD3+ and T CD56+ CD3+ and NK compared to the control range.

TABLE 5

Distribution (measured as %) of CDina26 + cells in lymphocyte subpopulations in 6 patients who underwent HSCT evaluated at the time of immune reconstitution and compared with the range obtained by evaluating 5 healthy donors.

| | % CD26 | | | | | | |
|---|---|---|---|---|---|---|---|
| | Healthy donors | Patients | | | | | |
| Subpopulation | range | CK | IP | BGL* | BG* | CJ* | DF* |
| T CD3+/CD4+ | 74-86 | 58 | 58 | 90 | 60 | 86 | 97 |
| T CD3+/CD8+ | 45-75 | 29 | 22 | 68 | 25 | 74 | 93 |
| T CD3+/CD16+ | 9-23 | 30 | 53 | 90 | 15 | 82 | 96 |
| T CD3+/CD56+ | 15-52 | 54 | 47 | 100 | 90 | 86 | 95 |
| NK CD3−/CD16+ | 7-23 | 33 | 21 | 33 | 17 | 61 | 49 |
| NK CD3−/CD56+ | 3-14 | 36 | 25 | 37 | 19 | 74 | 54 |
| B CD20+/CD19+ | 3-14 | 0 | 36 | 0 | 0 | 0 | 93 |

*At the time of evaluation, the patients had developed acute GvHD grade II.

In patients who developed aGvHD, in some cases, the value of the percentage is higher than in the two patients free of this complication (CK, IP). The patient DF showed significantly higher percentages of CD26 in all subsets, an index of cellular activation was very pronounced and it was not possible to estimate the index of the molecule CD26 MFIR.

In the two patients who did not develop aGvHD, the index showed MFIR values falling in the range of control, while in three patients with aGvHD in progress, MFIR values were increased in almost all subsets, and most especially in the sub-T CD3+ CD16+ and CD3+ T CD56+ (Table 6).

TABLE 6

Distribution (measured as MFIR) of CDina26 + cells in lymphocyte subpopulations in 6 patients who underwent HSCT evaluated at the time of immune reconstitution and compared with the range obtained by evaluating 5 healthy donors.

| | Healthy donors | MFIR index Patients | | | | | |
|---|---|---|---|---|---|---|---|
| Subpopulation | range | CK | IP | BGL* | BG* | CJ* | DF* |
| T CD3+/CD4+ | 3-30 | 3 | 1 | 62 | 25 | 21 | n.a |
| T CD3+/CD8+ | 2-15 | 1 | 2 | 25 | 7 | 23 | n.a |
| T CD3+/CD16+ | 1-2 | 2 | 1 | 89 | 9 | 23 | n.a |
| T CD3+/CD56+ | 3-14 | 4 | 2 | 165 | 37 | 40 | n.a |
| NK CD3−/CD16+ | 0-2 | 1 | 1 | 5 | 5 | 7 | n.a |
| NK CD3−/CD56+ | 0-2 | 1 | 1 | 6 | 3 | 8 | n.a |
| B CD20+/CD19+ | 0-8 | 0 | 1 | 0 | 0 | 0 | n.a |

n.a: not applicable

Example 4e

The expression of CD26 was also studied on mesenchymal stem cells, endothelial cells and fibroblasts.

Three experiments were set up using Mesenchymal Stem Cells (MSCs), propagated in vitro derived from bone marrow of three healthy adults. The analysis by flow cytometry showed that cells positive for CD13 and CD73, markers characteristic of MSCs are, however, negative for the expression of CD26 (CDina26 antigen). Three experiments were set up using endothelial cells (DC) from umbilical cord of three healthy subjects. Endothelial cells are negative for the expression of CD26 (CDina26 antigen).

Three experiments were set up using skin fibroblasts derived from three healthy adults. The analysis by flow cytometry demonstrated that 40% of fibroblasts expressed CD26 (range 32%-45%) with a MFIR index from 4 to 13.

Three experiments were set up using dendritic cells differentiated in vitro. Flow cytometric analysis showed that the cells positive for CD1a, a marker characteristic of DC differentiated in vitro, are however, negative for the expression of CD26.

The flow cytometry showed that monocytes cells positive for CD14 are positive for the expression of CD26 (range 97%-100%), MFIR index variable from 1 to 17.

These data demonstrated that T and NK subpopulations increased both the percentage or the expression of CDina26 antigen (MFIR) on membrane surface.

In aGvHD patients an increased expression of CD26 can be observed in T CD3+CD16+, T CD3+CD56+ and NK as compared with healthy donors.

These data summarize the ability of monoclonal antibodies anti CD26 of CDina26 to specifically bind to activated regulatory T cells, interfering with their expansion and with their role in the modulation of the immune response in aGvHD.

Example 5

Clinical Studies: Treatment of Graft-versus-Host Disease (GvHD)

A clinical study has been conducted for establishing the safety and efficacy of CDina26 in aGvHD (acute Graft-versus-Host Disease) patient.

Summary

Patients enrolled in the study received a fixed dose of CDina26 of 2 mg/day (which corresponds to an average of 1.11 $mg/m^2$ per day) for 5 consecutive days. The composition administered to patients included the antibody of the present invention in a range between 2 and 10 mg according to body surface diluted in 100 ml of sterile saline solution together with corticosteroids and antihistamine. Patients continued to receive their standard GvHD treatment (6-methylprednisolone 1-2 mg/kg/day i.v., and cyclosporine). Supportive care was the conventional antibacterial, antifungal and antiviral therapy. In the present application, the units $mg/m^2$ and mg/($m^2$ body surface area) are used interchangeably.

The main evaluation of this study was the frequency of patients "responding" to the studied treatment, assessed on day 10 after 5 days of therapy.

The definition of responsiveness was based on the following criteria:

COMPLETE RESPONSE (CR)→resolution of all signs of GvHD

PARTIAL RESPONSE (PR)→improvement in grading of GvHD

STABILITY→no change in grading of GvHD

AGGRAVATION→aggravation in grading of GvHD

Patients with complete or partial response were considered responsive.

TABLE 7

Glucksberg acute GvHD staging (Glucksberg et al., 1974)

| Organ | Stage 1 | Stage 2 | Stage 3 | Stage 4 |
|---|---|---|---|---|
| Skin Maculo-papular rash | <25% of body surface | 25-50% of body surface | Generalized erythroderma | Generalized erythroderma with bullae formation and desquamation |
| Liver Bilirubin | 2-3 mg/dl | 3.1-6 mg/dl | 6.1-15 mg/dl | >15 mg/dl |
| GI Diarrhoea | >500 ml/day | >1000 ml/day | >1500 ml/day | >1500 ml/day Severe abdominal pain with or without ileus |

TABLE 8

Glucksberg of acute GVHD grading (Glucksberg et al., 1974)

| Overall grade | Skin | Liver | GI | ECOG |
|---|---|---|---|---|
| I | 1-2 | 0 | 0 | 0 |
| II | 1-3 | 1 | and/or 1 | 0-1 |
| III | 2-3 | 2-4 | and/or 2-3 | 2-3 |
| IV | 2-4 | 2-4 | and/or 2-4 | 3-4 |

GI: gastrointestinal tract

Eastern Cooperative Oncology Group (ECOG) Performance Status:

Additional evaluations include the following:

staging of GvHD, organ for organ (This evaluation is carried out at the day +10 and day +30.);

complications occurrence such as: infection, bleeding, transfusion necessity (This evaluation is carried out until the end of the hospitalization at day +30.);

at the 1 year visit the following parameters are recorded: survival status, Karnofsky index, chronic GvHD, possible relapse of the hematological disease for which transplantation was performed, possible appearance of a new tumor.

Demographic and Other Baseline Characteristics

Eleven patients were included in the data set for the efficacy evaluation. Seven patients had grade III aGvHD, one patient had grade IV GvHD and one patient had grade II GvHD.

The median time to onset of aGvHD was 10 days (range 4-73 days).

All these patients had aGvHD which was considered at high risk because of visceral organ involvement.

Efficacy evaluation: the frequency of patients "responding" to 2 mg of CDina26 i.v. daily, administered for five consecutive days, at the current median follow up of 433 days is 11 on 12 (90%): six (6) complete responses, five (5) partial responses and one (1) non response.

Following the data in four patients (pt. 01, 03, 12, 14) in Glucksberq acute GvHD grading. The following abbreviations are used in the following Table:

pre CDina26 stands for patients' GvHD grade before the treatment with CDina26; best CDina26 stands for best patients' GvHD grade value after the treatment with CDina26; final CDina26 stands for the most recent patients' GvHD grade value; The Follow up values represent the days after CDina26 treatment.

TABLE 9

| | Pre CDina26 | | | | Best CDina26 | | | | Final CDina26 | | | | | |
|---|---|---|---|---|---|---|---|---|---|---|---|---|---|---|
| ID | GvHD Skin | GvHD Liver | GvHD gut | GvHD grade | GvHD Skin | GvHD Liver | GvHD gut | GvHD grade | GvHD Skin | GvHD Liver | GvHD gut | GvHD grade | Follow Up | Response |
| Pt01 | 2 | 0 | 2 | 3 | 0 | 0 | 0 | 0 | 0 | 0 | 0 | 0 | 365 | CR |
| Pt03 | 2 | 0 | 3 | 3 | 0 | 0 | 0 | 0 | 2 | 0 | 0 | 1 | 365 | PR |
| Pt12 | 2 | 0 | 0 | 2 | 0 | 0 | 0 | 0 | 1 | 0 | 1 | 1 | 341 | PR |
| Pt14 | 0 | 0 | 2 | 2 | 0 | 1 | 0 | 0 | 0 | 1 | 0 | 0 | 208 | CR |

FIG. 4*a* shows Grading of Skin GvHD, day 1, 10, 30 and last day ("last" in FIG. 4*a*) of the patient in the study. FIG. 4*b* illustrates Grading of liver GvHD, day 1, 10, 30 and last day of the patient in the study. FIG. 4*c* shows Grading of gut GvHD, day 1, 10, 30 and last day of the patient in the study.

Immune Recovery

Immunodeficiency is common in patients with acute GvHD, especially after prolonged treatment with steroids, and infections are the consequence of severe combined immune deficiency. FIG. 5 outlines absolute CD4 counts in 6 patients. CD4 counts tend to increase or remain essentially stable after CDina26 therapy, rather than showing a decline, as would be expected in case of a strong cytolytic activity of the antibody. The unit "counts/ul" stands for counts per microliter of blood of a patient.

Brief Summary of Adverse Events

The safety of CDina26 has been examined through a review of adverse events. Serious toxicities involving the haematologic and respiratory systems were considered as expected consequences of the conditioning regimen and transplant process. Overall 8 serious and 26 non-serious adverse events were reported as not related to CDina26 treatment. The Most frequently reported adverse events were related to the SOCs (System Organ Classes) "Infections and infestations" (n=5), "Renal and urinary disorders" (n=5), "Respiratory, thoracic and mediastinal disorders" (n=5) and "Skin and subcutaneous tissue disorders" (n=4).

Infections are a frequent complication of acute GvHD and steroid therapy. Therefore it was not unexpected to see a number of infectious episodes in the patients.

Eight fatal adverse events occurred after Day+100. None of these was considered as related to the treatment with CDina26.

Due to the fact that Steroid-resistant acute Graft-versus-Host-Disease following allogeneic haematopoietic stem cell transplantation is associated with a high mortality rate, the transplant related mortality (deaths due to transplant related complications, the majority of which are associated with aGvHD) was evaluated.

Considering all patients treated with CDina26 the incidence of Transplant Related Mortality (TRM) after 6 months from the treatment is 25% (3 of 12). Among TRM, two patients died from GvHD. None of these was related to treatment with CDina26.

FIG. 6 outlines the projected cumulative incidence of transplant related mortality of 13 control patients with grade III-IV acute GvHD, treated with steroids, cyclosporine and other immunosuppressive drugs, compared with 9 patients treated with steroids cyclosporine and CDina26.

Figure 7:
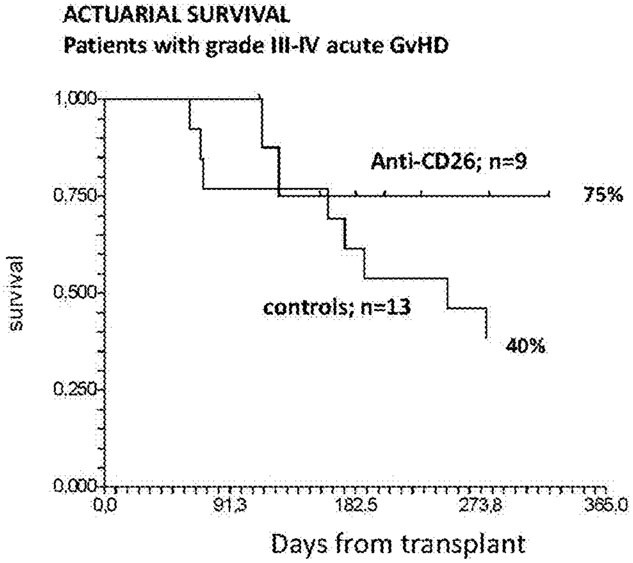
FIG. 7 shows a diagram illustrating the projected actuarial survival of 13 control patients with grade III-IV acute GvHD, treated with steroids, cyclosporine and other immunosuppressive drugs, compared with 9 patients treated with steroids, cyclosporine and CDina26.

The cumulative incidence of transplant related mortality in the 9 patients receiving CDina26 is currently 12%, compared to 62% for matched controls not receiving CDina26 (p=0.02). FIG. 7 outlines the projected actuarial Survival of 13 control patients with grade III-IV acute GvHD, treated with steroids, cyclosporine and other immunosuppressive drugs, compared with 9 patients treated with steroids, cyclosporine and CDina26. The p value is 0.2.

In conclusion, CDina26 patients show a lower mortality than non-CDina26 patients, i.e. patients that were not treated with CDina26.

Conclusions

Results of murine monoclonal antibody against CD26 therapy for steroid refractory acute GvHD in 11 patients have been extremely encouraging, both in terms of response and survival. Given the lack of any effective therapeutic measure in these circumstances, and given the lack of any improvement in therapy and outcome over the past 3 decades CDina26 resulted in a high rate of responses and a high proportion of surviving patients. It has to be pointed out that transplant mortality (TRM) directly attributed to the transplant and its complication is 62% for control patients with GvHD III-IV not receiving murine monoclonal antibody against CD26, and 25% for patients receiving CDina26. We believe these results are very promising for the clinician.

Example 6

A pharmaceutical composition containing at least one antibody of the present invention, in particular containing the antibodies produced by the PD 12002 hybridoma cell line deposit, CDina26, has for example the following composition:

TABLE 10

| Component | Quantity per vial |
|---|---|
| at least one antibody of the present invention, in particular the antibodies produced by PD 12002 hybridoma cell line deposit, CDina26 | 1 mg |
| DPBS (Dulbecco's Phosphate Buffered Saline) | 1 ml |
| 1 ml of DPBS comprising: | |
| KCl | 0.2 mg |
| $KH_2PO_4$ | 0.2 mg |
| NaCl | 8 mg |
| $Na_2HPO_4 \times 7H_2O$ | 2.16 mg |
| Water for injection | To 1 ml |

This pharmaceutical composition can be administered in particular by intravenous injection.

Example 7

Treatment of SAA (Severe Aplastic Anemia)

One patient with acquired SAA developed pancytopenia after an allogeneic HSCT. The patient had mixed CD3 chimerism (37% autologous) suggesting persistence of the auto-aggressive T cells, causing aplasia. Donor chimerism on bone marrow cells was 100% donor.

The patient received a course of anti-CD26 monoclonal antibodies CDina26, 2 mg/day i.v. (2 mg of CDina26 provided in the form of a solution for intravenous administration) for 5 days, as an outpatient, in a Day Hospital. Treatment was well tolerated with no adverse effects.

The blood counts of the patient after treatment are as follows:

| | Hb | WBC | Pt |
|---|---|---|---|
| 120 days before treatment | 10 | 1.7 | 70 |
| 7 days before treatment | 8.9 | 1.6 | 12 |

During Five Days the Treatment with Anti-CD26 Antibodies was Carried Out.

| | | | |
|---|---|---|---|
| 6 days after treatment | 8.4 | 2.6 | 22 |
| 20 days after treatment | 7.6 | 2.5 | 22 |
| 31 days after treatment | 10.4 | 4.8 | 32 |
| 48 days after treatment | 9.2 | 3.9 | 42 |
| 87 days after treatment | 9.7 | 4.4 | 66 |

(Blood counts were obtained 87 days after treatment, i.e. nearly 3 months after treatment, with anti-CD26 antibody). The following abbreviations was used: Hb (Hemoglobin), WBC (White Blood Cells), Pt (Platelet). The data above show that an inhibition of CD26 can be beneficial in patients with acquired SAA, due to its immunomodulatory effect, and the role in stem cell homing.

Example 8

Mapping of the PD 12002 Epitope

The epitopes recognized by the CDina26 antibody produced by hybridoma cell line deposited as PD 12002 have been identified by CLIPS™ Epitope Mapping technology. See, e.g., U.S. Pat. Nos. 7,863,239 and 7,972,993, the disclosures of which are herein incorporated by reference in their entirety. Briefly, CLIPS™ technology structurally fixes peptides into defined three-dimensional structures. This results in functional mimics of even the most complex binding sites. The CLIPS™ reaction takes place between bromo groups of the CLIPS™ scaffold and thiol side chains of cysteines. The reaction is fast and specific under mild conditions (Timmerman et al., J. Mol. Recognit. 2007; 20: 283-29).

CLIPS™ library screening starts with the conversion of the human CD26 target protein into a library of overlapping peptide constructs, using a combinatorial matrix design. On a solid carrier, a matrix of linear peptides is synthesized, which are subsequently shaped into spatially defined CLIPS™ constructs. Constructs representing several parts of a discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail.

First, the adenosine deaminase binding domain (residues 356 to 522 of SEQ ID NO: 144) of the human CD26 protein sequence was selected for in-depth analysis. This region of CD26 was extended and split into two overlapping domains, that of residues 260 to 400, and 380 to 538 of SEQ ID NO: 144. Competitive binding assays revealed that CDina26 recognizes an epitope localized close to residue R358 of human CD26 (SEQ ID NO: 144).

Second, a total of 5833 overlapping peptides of CD26 were synthesized and tested for specific binding by CDina26. The analysis of linear peptides identified multiple regions that were specifically recognized by CDina26. Four regions of CD26 showed significant binding:

VWVSPNGTFLAYAQ (SEQ ID NO: 148 corresponding to residues 215 to 227 of SEQ ID NO: 144), QLRCSGPGLPLYTLH (SEQ ID NO: 149 corresponding to residues 466 to 483 of SEQ ID NO: 144)

LNETKFWYQMILP (SEQ ID NO: 150 corresponding to residues 519 to 531 of SEQ ID NO: 144)

MGFVDNKRIAIWGWSY (SEQ ID NO: 151 corresponding to residues 616 to 631 of SEQ ID NO: 144)

These 4 regions of CD26 appear to be spaced apart on the published crystal structure and therefore may not all form a single discontinuous epitope for CDina26. Furthermore, based on the published CD26 crystal structure, 3 of the 4 regions appear to be almost entirely buried inside CD26. The exception is VWVSPNGTFLAYAQ (SEQ ID NO: 148), which is surface exposed at least at the PNGTF (SEQ ID NO: 152 corresponding to residues 218 to 222 of SEQ ID NO: 144) residues.

Third, three distinct surface regions of CD26 were selected for analysis of discontinuous epitopes. Matrix 1 covers the catalytic area and N-terminal regions in proximity of the catalytic area (corresponding to residues 260 to 400 of SEQ ID NO: 144). Matrix 2 covers the catalytic area and C-terminal regions in proximity of the catalytic area that partially overlaps with set matrix1 (corresponding to residues 380 to 538 of SEQ ID NO: 144). Finally, Matrix 3 covers a specific protruding loop from CD26, which forms an immune-dominant structure (corresponding to residues 226 to 252 of SEQ ID NO: 144).

Compared to linear peptides, the discontinuous peptides showed relatively lower signals, but the signals were more consistent. When results obtained with all 3 matrices were taken together, multiple CDina26 binding regions of CD26 were identified.

Matrix 3, which focused on a protruding loop of CD26 corresponding to residues 226 to 252 of SEQ ID NO: 144, did not identify any regions with significant CDina26 binding.

Matrix 1 (N-terminal of the focus region corresponding to residues 260 to 400 of SEQ ID NO: 144) yielded 3 CDina26 binding regions:

DYDESSGRWNCLVAR (SEQ ID NO: 146 corresponding to residues 329 to 343 of SEQ ID NO: 144).

DVTWATQERISLQWL (SEQ ID NO: 147 corresponding to residues 302 to 316 of SEQ ID NO: 144)

TTGVVVGRFRPSEPHF (SEQ ID NO: 153 corresponding to residues 350 to 364 of SEQ ID NO: 144)

The strongest binding was observed for DYDESSGRWNCLVAR (SEQ ID NO: 146). When only peptides comprising DYDESSGRWNCLVAR (SEQ ID NO: 146) were considered, the best binding peptides were those that also comprised RFRPSEPHF (SEQ ID NO: 154 corresponding to residues 356 to 364 of SEQ ID NO: 144). RFRPSEPHF (SEQ ID NO: 154) includes the specific R358 residue mentioned above. The specific additive effect on binding was consistent with the CDina26 antibody targeting a discontinuous epitope that includes DYDESSGRWNCLVAR (SEQ ID NO: 146) and TTGVVVGRFRPSEPHF (SEQ ID NO: 153). In another embodiment, the epitope further comprises DVTWATQERISLQWL (SEQ ID NO: 147).

Matrix 2 yielded 4 binding regions:

TFITKGTWEVIG (SEQ ID NO: 155 corresponding to residues 395 to 406 of SEQ ID NO: 144)

DYLYYISNE (SEQ ID NO: 156 corresponding to residues 413 to 421 of SEQ ID NO: 144)

SCELNPERCQYY (SEQ ID NO: 157 corresponding to residues 446 to 457 of SEQ ID NO: 144)

SGPGLP (SEQ ID NO: 158 corresponding to residues 473 to 478 of SEQ ID NO: 144)

CDina26 binding to the Matrix 2 regions was weaker than binding to DYDESSGRWNCLVAR (SEQ ID NO: 146). Based on the published CD26 crystal structure, regions DYLYYISNE (SEQ ID NO: 156) and SGPGLP (SEQ ID NO: 158) appear to be mostly hidden inside the protein. Regions TFITKGTWEVIG (SEQ ID NO: 155) and SAELNPERCQYY (SEQ ID NO: 157) are surface exposed and accessible by an antibody.

A visual comparison of CDina26 binding to the 7 identified discontinuous binding regions in CD26 the 7 is shown in FIG. 12 that displays the average binding to all discontinuous peptides that contain one of the identified binding sequences. Here, DYDESSGRWNCLVAR (SEQ ID NO: 146) was the strongest binder, while DVTWATQERISLQWL (SEQ ID NO: 147) was slightly stronger than TTGVVVGRFRPSEPHF (SEQ ID NO: 153).

The strongest binding region, DYDESSGRWNCLVAR (SEQ ID NO: 146), is mostly exposed on the surface based on the published CD26 crystal structure. Region TTGVVVGRFRPSEPHF (SEQ ID NO: 153) is nearly completely hidden inside the protein. Region DVTWATQERISLQWL (SEQ ID NO: 147) is partly exposed on the surface at ATQER (SEQ ID NO: 159 corresponding to residues 306 to 310 of SEQ ID NO: 144), and is located adjacent to DYDESSGRWNCLVAR (SEQ ID NO: 146).

The epitope mapping results were consistent with CDina26 specifically binding a discontinuous epitope of CD26 comprising DYDESSGRWNCLVAR (SEQ ID NO: 146). In one embodiment, the discontinuous epitope further comprises one or both of DVTWATQERISLQWL (SEQ ID NO: 147) and PNGTF (SEQ ID NO: 152). While PNGTF (SEQ ID NO: 152) is conserved between human and pig CD26, the sequence differences in other components of the epitope (such as DYDESSGRWNCLVAR (SEQ ID NO: 146), which is not conserved between human and pig) is enough to abolish binding of CDina26 to the native pig CD26. In another embodiment, the epitope further comprises VWVSPNGTFLAYAQ (SEQ ID NO: 148).

Example 9

Binding Affinity of CDina26 to CD26

Surface Plasmon Resonance system (Biacore®) was used to determine the affinity of CDina26 for human CD26 according to standard protocols. Affinity measurements were taken at 25° C., immobilizing on carboxymethyl dextran chip (CM5) 10.000 RU of an anti-IgG2b antibody (GE Healthcare, 22-0648-97 AC). CDina26 was prepared as stock in HBS-EP (0.01M HEPES, pH 7.4, 0.15M NaCl, 3 mM EDTA, 0.005% Surfactant P20) running buffer in a final concentration of 50 μg/ml, and for each experiment 2.000 RU were reversibly immobilized on the chip by injection with a flow of 10 μl/min in a period of 180 seconds.

Purified recombinant human CD26 (rhDipeptidyl peptidase IV; Creative BioMart; CAT #DPP4-116H) was prepared in a stock concentration of 5.8x10-6 M. CD26 was injected at increasing concentrations of $30\times10^{-9}$, $90\times10^{-9}$ M, $270\times10^{-9}$ M and $810\times10^{-9}$ M. The CD26 samples were injected with a flow of 10 μl/minute; with HBS-EP buffer used as running buffer. A typical recording included a 3 minutes period of injection of the CD26 followed by a period of 8 minutes of dissociation. The raw binding data was analyzed according to standard methods. CM5 chip with immobilized anti-IgG2b antibody was regenerated by injection of 10 mM Glycin-HCl pH 1.7 with a flow of injection of 20 μl/min and for a period of 60 seconds.

The results of the affinity measurements for CDina26 are shown below. Applicants believe that the CDina26 possesses superior binding properties compared to the prior art antibodies, and thus represent a significant improvement over the prior art.

| Ligand CM5 | Ligand Anti-IgG2b | Analyte | $K_{on}$ (1/Ms) | $K_{off}$ (1/s) | $K_D$ (M) |
|---|---|---|---|---|---|
| Anti-IgG2b | CDina26 | Human CD26 | 2.63E+04 | 1.32E−04 | 5.02e−09 |

Various modifications and variations of the described composition and method of the invention will be apparent to those in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those in the relevant fields are intended to be within the scope of the following claims.

Example 10

Contacts between CD26 and an Anti-CD26 Monoclonal Antibody Fab

To investigate the contacts between CD26 and the anti-CD26-Fab, the CCP4 software NCONT(1) was used. The criteria displaying all distances between 0.0-4.0 Å were used. A summary of the contacts is given in Table 11 and all interactions and distances are shown in Tables 12 and 13.

TABLE 11

A summary of interacting residues between CD26 and the anti-CD26-Fab.

| CDR | Anti-CD26 - Fab residues | CD26 residues |
|---|---|---|
| HC-CDR1 | Arg30 | Ser412, Leu436, Ser437 |
| | Ser31 | Tyr386, Gln388 |
| | Tyr32 | Asp367, Asn369, Gln388 |
| | Asp33 | Gln388, Lys391 |
| HC-CDR2 | Trp50 | Lys391, Asp393 |
| | Phe52 | Tyr386, Gln388, Thr395, Tyr439 |
| | Gly54 | Tyr439 |
| | Asp55 | Thr395 |
| | Lys74 | Ser437, Asp438 |
| HC-CDR3 | Trp99 | Asp390 |
| | Thr100 | Gln388, Asp390 |
| | Val101 | Arg343, Ile389, Asp390 |
| | Val102 | Asn369 |
| | Gly103 | Asn369 |
| | Tyr106 | Asp329, Asn338, Leu340, Arg343 |
| LC-CDR1 | Ser30 | Val341 |
| | Tyr31 | Ala342 |

TABLE 11-continued

A summary of interacting residues between CD26 and the anti-CD26-Fab.

| CDR | Anti-CD26 - Fab residues | CD26 residues |
|---|---|---|
| LC-CDR2 | Tyr48 | Leu340, Ala342, Arg343, Asp390 |
| | Ser49 | Leu340, Val341, Ala342 |
| | Asn52 | Asn338, Leu340 |
| LC-CDR3 | Arg90 | Asp390 |
| | Ser91 | Lys392 |
| | Tyr93 | Lys392, Asp393 |

The epitope was defined as all residues within a distance of 0.0-4.0 Å between the CD26 and the anti-CD26-Fab. The following residues were found: Asp329, Asn338, Leu340, Val341, Ala342, Arg343, Asp367, Asn369, Tyr386, Gln388, Ile389, Asp390, Lys391, Lys392, Asp393, Thr395, Ser412, Leu436, Ser437, Asp438 and Tyr439.

TABLE 12

Interaction between the heavy chain of the anti-CD26-Fab and CD26

| SOURCE ATOMS | TARGET ATOMS | DISTANCE (Å) |
|---|---|---|
| /1/H/ 30(ARG)./CD [C]: | /1/A/ 436(LEU)./O [O]: | 3.38 |
| | /1/A/ 436(LEU)./C [C]: | 3.98 |
| /1/H/ 30(ARG)./NE [N]: | /1/A/ 436(LEU)./O [O]: | 3.70 |
| /1/H/ 30(ARG)./CZ [C]: | /1/A/ 412(SER)./O [O]: | 3.91 |
| | /1/A/ 436(LEU)./CB [C]: | 3.79 |
| /1/H/ 30(ARG)./NH1[N]: | /1/A/ 437(SER)./OG [O]: | 3.52 |
| /1/H/ 30(ARG)./NH2[N]: | /1/A/ 412(SER)./O [O]: | 2.94 |
| | /1/A/ 436(LEU)./CB [C]: | 3.72 |
| | /1/A/ 436(LEU)./CD1[C]: | 3.83 |
| /1/H/ 31(SER)./CA [C]: | /1/A/ 386(TYR)./OH [O]: | 3.62 |
| /1/H/ 31(SER)./CB [C]: | /1/A/ 386(TYR)./OH [O]: | 3.66 |
| /1/H/ 31(SER)./C [C]: | /1/A/ 386(TYR)./OH [O]: | 3.51 |
| /1/H/ 31(SER)./O [O]: | /1/A/ 388(GLN)./NE2[N]: | 3.92 |
| | /1/A/ 386(TYR)./CZ [C]: | 3.42 |
| | /1/A/ 386(TYR)./CE2[C]: | 3.29 |
| | /1/A/ 388(GLN)./CG [C]: | 3.87 |
| | /1/A/ 388(GLN)./CD [C]: | 3.83 |
| | /1/A/ 386(TYR)./OH [O]: | 2.71 |
| /1/H/ 32(TYR)./CA [C]: | /1/A/ 388(GLN)./OE1[O]: | 3.61 |
| | /1/A/ 388(GLN)./CD [C]: | 4.00 |
| /1/H/ 32(TYR)./OH [O]: | /1/A/ 369(ASN)./CB [C]: | 3.93 |
| | /1/A/ 367(ASP)./OD1[O]: | 3.90 |
| /1/H/ 32(TYR)./C [C]: | /1/A/ 388(GLN)./OE1[O]: | 3.84 |
| /1/H/ 33(ASP)./N [N]: | /1/A/ 388(GLN)./NE2[N]: | 3.89 |
| | /1/A/ 388(GLN)./OE1[O]: | 3.07 |
| | /1/A/ 388(GLN)./CD [C]: | 3.79 |
| /1/H/ 33(ASP)./CA [C]: | /1/A/ 388(GLN)./OE1[O]: | 3.99 |
| /1/H/ 33(ASP)./CB [C]: | /1/A/ 388(GLN)./OE1[O]: | 3.70 |
| /1/H/ 33(ASP)./CG [C]: | /1/A/ 388(GLN)./NE2[N]: | 3.54 |
| | /1/A/ 391(LYS)./NZ [N]: | 3.63 |
| | /1/A/ 388(GLN)./OE1[O]: | 3.62 |
| /1/H/ 33(ASP)./OD1[O]: | /1/A/ 388(GLN)./NE2[N]: | 2.79 |
| | /1/A/ 391(LYS)./NZ [N]: | 3.52 |
| | /1/A/ 388(GLN)./OE1[O]: | 3.52 |
| | /1/A/ 388(GLN)./CD [C]: | 3.58 |
| /1/H/ 33(ASP)./OD2[O]: | /1/A/ 391(LYS)./CE [C]: | 3.29 |
| | /1/A/ 391(LYS)./NZ [N]: | 2.96 |
| | /1/A/ 391(LYS)./CD [C]: | 3.35 |
| /1/H/ 50(TRP)./CE2[C]: | /1/A/ 391(LYS)./CE [C]: | 3.83 |
| | /1/A/ 391(LYS)./NZ [N]: | 3.84 |
| /1/H/ 50(TRP)./CE3[C]: | /1/A/ 391(LYS)./NZ [N]: | 3.94 |
| /1/H/ 50(TRP)./CZ3[C]: | /1/A/ 391(LYS)./NZ [N]: | 3.53 |
| /1/H/ 50(TRP)./CH2[C]: | /1/A/ 391(LYS)./CE [C]: | 4.00 |
| | /1/A/ 391(LYS)./NZ [N]: | 3.27 |
| /1/H/ 50(TRP)./CZ2[C]: | /1/A/ 393(ASP)./OD2[O]: | 3.29 |
| | /1/A/ 391(LYS)./CE [C]: | 3.64 |
| | /1/A/ 391(LYS)./NZ [N]: | 3.45 |

TABLE 12-continued

Interaction between the heavy chain of the anti-CD26-Fab and CD26

| SOURCE ATOMS | TARGET ATOMS | DISTANCE (Å) |
|---|---|---|
| /1/H/ 52(PHE)./CD1[C]: | /1/A/ 388(GLN)./NE2[N]: | 3.64 |
| /1/H/ 52(PHE)./CE1[C]: | /1/A/ 388(GLN)./NE2[N]: | 3.91 |
| | /1/A/ 386(TYR)./CE2[C]: | 3.59 |
| | /1/A/ 386(TYR)./CD2[C]: | 3.94 |
| /1/H/ 52(PHE)./CZ [C]: | /1/A/ 386(TYR)./CE2[C]: | 3.54 |
| | /1/A/ 386(TYR)./CD2[C]: | 3.47 |
| | /1/A/ 439(TYR)./OH [O]: | 3.73 |
| /1/H/ 52(PHE)./CE2[C]: | /1/A/ 395(THR)./CG2[C]: | 3.90 |
| | /1/A/ 439(TYR)./CE2[C]: | 4.00 |
| /1/H/ 52(PHE)./CD2[C]: | /1/A/ 395(THR)./CG2[C]: | 3.74 |
| | /1/A/ 395(THR)./CB [C]: | 3.95 |
| | /1/A/ 395(THR)./OG1[O]: | 3.71 |
| /1/H/ 54(GLY)./C [C]: | /1/A/ 439(TYR)./CE2[C]: | 3.86 |
| /1/H/ 54(GLY)./O [O]: | /1/A/ 439(TYR)./CE2[C]: | 3.53 |
| | /1/A/ 439(TYR)./CD2[C]: | 3.56 |
| /1/H/ 55(ASP)./CG [C]: | /1/A/ 395(THR)./CG2[C]: | 3.77 |
| /1/H/ 55(ASP)./OD1[O]: | /1/A/ 395(THR)./CG2[C]: | 3.77 |
| /1/H/ 55(ASP)./OD2[O]: | /1/A/ 395(THR)./CG2[C]: | 3.40 |
| /1/H/ 74(LYS)./CD [C]: | /1/A/ 437(SER)./O [O]: | 3.48 |
| /1/H/ 74(LYS)./CE [C]: | /1/A/ 437(SER)./O [O]: | 3.71 |
| /1/H/ 74(LYS)./NZ [N]: | /1/A/ 437(SER)./C [C]: | 3.61 |
| | /1/A/ 437(SER)./O [O]: | 2.82 |
| | /1/A/ 438(ASP)./CA [C]: | 3.93 |
| /1/H/ 99(TRP)./O [O]: | /1/A/ 390(ASP)./OD2[O]: | 3.39 |
| /1/H/ 100(THR)./CA [C]: | /1/A/ 390(ASP)./CG [C]: | 3.80 |
| | /1/A/ 390(ASP)./OD2[O]: | 3.41 |
| /1/H/ 100(THR)./CG2[C]: | /1/A/ 388(GLN)./OE1[O]: | 3.45 |
| | /1/A/ 388(GLN)./CB [C]: | 3.99 |
| | /1/A/ 390(ASP)./CB [C]: | 3.81 |
| /1/H/ 100(THR)./C [C]: | /1/A/ 390(ASP)./OD2[O]: | 3.60 |
| /1/H/ 101(VAL)./N [N]: | /1/A/ 390(ASP)./CG [C]: | 3.40 |
| | /1/A/ 390(ASP)./OD2[O]: | 2.83 |
| | /1/A/ 390(ASP)./OD1[O]: | 3.61 |
| /1/H/ 101(VAL)./CA [C]: | /1/A/ 390(ASP)./OD2[O]: | 3.81 |
| /1/H/ 101(VAL)./CB [C]: | /1/A/ 390(ASP)./OD2[O]: | 3.73 |
| /1/H/ 101(VAL)./CG1[C]: | /1/A/ 343(ARG)./NH2[N]: | 3.71 |
| /1/H/ 101(VAL)./CG2[C]: | /1/A/ 390(ASP)./OD2[O]: | 3.69 |
| /1/H/ 101(VAL)./O [O]: | /1/A/ 390(ASP)./OD1[O]: | 3.87 |
| | /1/A/ 389(ILE)./CG2[C]: | 3.66 |
| | /1/A/ 343(ARG)./NH2[N]: | 3.27 |
| /1/H/ 102(VAL)./CG1[C]: | /1/A/ 369(ASN)./CB [C]: | 3.81 |
| | /1/A/ 369(ASN)./CG [C]: | 3.58 |
| | /1/A/ 369(ASN)./ND2[N]: | 3.43 |
| /1/H/ 102(VAL)./C [C]: | /1/A/ 369(ASN)./OD1[O]: | 3.90 |
| /1/H/ 103(GLY)./N [N]: | /1/A/ 369(ASN)./OD1[O]: | 2.91 |
| | /1/A/ 369(ASN)./CG [C]: | 3.51 |
| | /1/A/ 369(ASN)./ND2[N]: | 3.85 |
| /1/H/ 103(GLY)./CA [C]: | /1/A/ 369(ASN)./OD1[O]: | 3.55 |
| /1/H/ 103(GLY)./O [O]: | /1/A/ 369(ASN)./ND2[N]: | 3.89 |
| /1/H/ 106(TYR)./CD1[C]: | /1/A/ 343(ARG)./NH2[N]: | 3.92 |
| /1/H/ 106(TYR)./CE1[C]: | /1/A/ 343(ARG)./NH1[N]: | 3.74 |
| | /1/A/ 343(ARG)./NH2[N]: | 3.72 |
| /1/H/ 106(TYR)./OH [O]: | /1/A/ 340(LEU)./CD1[C]: | 3.40 |
| | /1/A/ 329(ASP)./OD2[O]: | 3.96 |
| | /1/A/ 338(ASN)./ND2[N]: | 3.94 |

TABLE 13

Interaction between the light chain of the anti-CD26-Fab and CD26

| SOURCE ATOMS | TARGET ATOMS | DISTANCE (Å) |
|---|---|---|
| /1/L/ 30(SER)./O [O]: | /1/A/ 341(VAL)./CG1[C]: | 3.56 |
| /1/L/ 31(TYR)./CD1[C]: | /1/A/ 342(ALA)./N [N]: | 3.93 |
| | /1/A/ 342(ALA)./CA [C]: | 3.78 |
| /1/L/ 31 (TYR)./CE1[C]: | /1/A/ 342(ALA)./CB [C]: | 3.94 |
| | /1/A/ 342(ALA)./CA [C]: | 3.56 |

TABLE 13-continued

Interaction between the light chain of the anti-CD26-Fab and CD26

| SOURCE ATOMS | TARGET ATOMS | DISTANCE (Å) |
|---|---|---|
| /1/L/ 31(TYR)./CZ [C]: | /1/A/ 342(ALA)./CB [C]: | 3.63 |
| | /1/A/ 342(ALA)./CA [C]: | 3.79 |
| /1/L/ 31(TYR)./CE2[C]: | /1/A/ 342(ALA)./CB [C]: | 3.67 |
| /1/L/ 31(TYR)./CD2[C]: | /1/A/ 342(ALA)./CB [C]: | 3.99 |
| /1/L/ 48(TYR)./CE1[C]: | /1/A/ 390(ASP)./OD2[O]: | 3.67 |
| | /1/A/ 342(ALA)./CB [C]: | 3.71 |
| /1/L/ 48(TYR)./CZ [C]: | /1/A/ 390(ASP)./OD2[O]: | 3.75 |
| | /1/A/ 390(ASP)./OD1[O]: | 3.83 |
| | /1/A/ 342(ALA)./CB [C]: | 3.80 |
| /1/L/ 48(TYR)./OH [O]: | /1/A/ 390(ASP)./CG [C]: | 3.16 |
| | /1/A/ 390(ASP)./OD2[O]: | 3.27 |
| | /1/A/ 343(ARG)./CG [C]: | 3.72 |
| | /1/A/ 390(ASP)./OD1[O]: | 2.71 |
| | /1/A/ 342(ALA)./CB [C]: | 3.53 |
| | /1/A/ 343(ARG)./NE [N]: | 3.49 |
| /1/L/ 48(TYR)./CE2[C]: | /1/A/ 340(LEU)./CD2[C]: | 3.60 |
| /1/L/ 48(TYR)./CD2[C]: | /1/A/ 340(LEU)./CD2[C]: | 3.73 |
| /1/L/ 49(SER)./CB [C]: | /1/A/ 342(ALA)./CB [C]: | 3.84 |
| | /1/A/ 340(LEU)./CD2[C]: | 3.84 |
| /1/L/ 49(SER)./OG [O]: | /1/A/ 342(ALA)./CB [C]: | 3.79 |
| | /1/A/ 340(LEU)./C [C]: | 3.87 |
| | /1/A/ 341(VAL)./N [N]: | 3.24 |
| | /1/A/ 341(VAL)./CA[C]: | 3.90 |
| | /1/A/ 341(VAL)./CB[C]: | 3.98 |
| | /1/A/ 342(ALA)./N [N]: | 3.29 |
| | /1/A/ 340(LEU)./CA [C]: | 3.98 |
| | /1/A/ 340(LEU)./CB [C]: | 3.86 |
| /1/L/ 52(ASN)./CG [C]: | /1/A/ 340(LEU)./CD2[C]: | 3.72 |
| | /1/A/ 338(ASN)./ND2[N]: | 3.64 |
| /1/L/ 52(ASN)./OD1[O]: | /1/A/ 338(ASN)./CG [C]: | 3.80 |
| | /1/A/ 338(ASN)./ND2[N]: | 2.87 |
| /1/L/ 52(ASN)./ND2[N]: | /1/A/ 340(LEU)./CG [C]: | 3.91 |
| | /1/A/ 340(LEU)./CD2[C]: | 3.41 |
| | /1/A/ 338(ASN)./ND2[N]: | 3.80 |
| /1/L/ 90(ARG)./NH2[N]: | /1/A/ 390(ASP)./O [O]: | 3.97 |
| /1/L/ 91(SER)./C [C]: | /1/A/ 392(LYS)./NZ [N]: | 3.77 |
| /1/L/ 91(SER)./O [O]: | /1/A/ 392(LYS)./CD [C]: | 3.98 |
| | /1/A/ 392(LYS)./NZ [N]: | 3.05 |
| /1/L/ 92(SER)./CA [C]: | /1/A/ 392(LYS)./NZ [N]: | 3.84 |
| /1/L/ 93(TYR)./CZ [C]: | /1/A/ 393(ASP)./OD1[O]: | 3.48 |
| /1/L/ 93(TYR)./OH [O]: | /1/A/ 393(ASP)./CG [C]: | 3.68 |
| | /1/A/ 393(ASP)./OD2[O]: | 3.93 |
| | /1/A/ 393(ASP)./OD1[O]: | 2.72 |
| /1/L/ 93(TYR)./CE2[C]: | /1/A/ 393(ASP)./CG [C]: | 3.98 |
| | /1/A/ 393(ASP)./OD1[O]: | 3.39 |
| /1/L/ 93(TYR)./CD2[C]: | /1/A/ 392(LYS)./NZ [N]: | 3.90 |

REFERENCES

All references cited herein, including e.g. patent publications, patent applications, textbooks, scientific publications, to the extent that they are not already incorporated, are hereby incorporated by reference in their entirety. In addition, the following references are also incorporated by reference herein in their entirety, including references cited in such references:

Akpek G, Boitnott J K, Lee L A, et al. *Hepatitic variant of graft versus host disease after donor lymphocyte infusion*. Blood 2002; 100: 3903-3907.

Altschul et al., 1996, Methods in Enzymology 266:460-480.

Andris-Widhopf et al. (2000), Phage Display Laboratory Manual, 1st edition, Cold Spring Harbor Laboratory Press, pp. 9.1-9.22.

Anke Franzke, Robert Geffers, J Katrin Hunger, Susanne Pfortner, Wenji Piao, Philipp Ivanyi, Jens Grosse, Michael Probst-Kepper, Arnold Ganser and Jan Buer. Identification of novel regulators in T-cell differentiation of aplastic anemia patients. *BMC Genomics* 2006, 7:263

Ausubel et al., eds, 1994, Current Protocols in Molecular Biology, Vol. 1, John Wiley & Sons, Inc., New York.

Aytac et al. (2003) British Journal of Cancer 88:455-462.

Bacigalupo A, Passweg J. Diagnosis and treatment of acquired aplastic anemia. Hematol Oncol Clin North Am. 2009; 23: 159-70.

Baines et al., "Purification of Immunoglobulin G (IgG)," in METHODS IN MOLECULAR BIOLOGY, VOL. 10, pages 79-104 (The Humana Press, Inc. 1992).

Bird R E and Walker B W, "Single Chain Antibody Variable Regions," TIBTECH, Vol 9: 132-137 (1991).

Boerner et al., 1991, J. Immunol., 147 (I):86-95.

Brekke and Loset, 2003, Curr. Opin. Pharmacol. 3:544-50.

Broxmeyer, H. E. (2006). Umbilical Cord Blood Stem Cells: Collection, Processing, and Transplantation. Blood Banking and Transfusion Medicine: Basic Principles and Practice. C. D. Hillyer, Silberstein, L. E., Ness, P. M., Anderson, K. C., and Roback, J., Churchill Livingston, an imprint of Elsevier, Inc.: 823-832.

Broxmeyer, H. E., G. Hangoc, S. Cooper, T. Campbell, S. Ito and C. Mantel (2007). AMD3100 and CD26 modulate mobilization, engraftment, and survival of hematopoietic stem and progenitor cells mediated by the SDF-1/CXCL12-CXCR4 axis. Ann N Y Acad Sci 1106: 1-19. Epub 2007 Mar. 14. PubMed PMID: 17360804.

Brummell et al., Biochem. 32: 1180-1 187 (1993).

Burks et al., Proc. Natl. Acad. Sci. USA 94:412-417 (1997).

Busso N, Wagtmann N, Herling C et al. Circulating CD26 is negatively associated with inflammation in human and experimental arthritis. Am J Pathol 2005; 166: 433-442.

Campbell T B, Broxmeyer H E. CD26 inhibition and hematopoiesis: a novel approach to enhance transplantation. Front Biosci. 2008 Jan. 1; 13:1795-805. Review. PubMed PMID: 17981668.

Campbell T B, Hangoc G, Liu Y, Pollok K, Broxmeyer H E. Inhibition of CD26 in human cord blood CD34+ cells enhances their engraftment of nonobese diabetic/severe combined immunodeficiency mice. Stem Cells Dev. 2007 June; 16(3):347-54. PubMed PMID: 17610364.

Carter et al., Proc. Nat'l Acad. Sci. USA 89: 4285 (1992).

Charo I F, Peters W. Chemokine receptor 2 (CCR2) in atherosclerosis, infectious diseases, and regulation of T-cell polarization. *Microcirculation* 2003, 10(3-4): 259-264.

Chothia et al., J. Mol. Biol. 1987, 196(4):901-17).

Christopherson K W 2nd, Hangoc G, Broxmeyer HE. Cell surface peptidase CD26/dipeptidylpeptidase IV regulates CXCL12/stromal cell-derived factor-1 alpha-mediated chemotaxis of human cord blood CD34+ progenitor cells. J Immunol. 2002 Dec. 15; 169(12):7000-8. PubMed PMID: 12471135.

Christopherson K W 2nd, Cooper S, Broxmeyer H E. Cell surface peptidase CD26/DPPIV mediates G-CSF mobilization of mouse progenitor cells. Blood. 2003 Jun. 15; 101(12):4680-6. Epub 2003 Feb. 6. PubMed PMID: 12576320.

Christopherson K W, Cooper S, Hangoc G, Broxmeyer H E. CD26 is essential for normal G-CSF-induced progenitor cell mobilization as determined by CD26–/– mice. Exp Hematol. 2003 November; 31(11):1126-34. PubMed PMID: 14585379.

Christopherson K W II, Hangoc G, Mantel C R, Broxmeyer H E. Modulation of haematopoietic stem cell homing and engraftment by CD26. Science 2004; 305: 1000-1003. PubMed PMID: 15310902.

Christopherson I I, K. W., L. A. Paganessi, S. Napier and N. K. Porecha (2007). CD26 Inhibition on CD34(+) or Lineages Human Umbilical Cord Blood Donor Hematopoietic Stem Cells/Hematopoietic Progenitor Cells Improves Long-Term Engraftment into NOD/SCID/Beta2(null) Immunodeficient Mice. Stem Cells Dev 16(3): 355-60.

Cole et al., Monoclonal Antibodies and Cancer Therapy, Alan R. Liss, p. 77 (1985);

Coligan et al. Eds. (1991) CURRENT PROTOCOLS IN IMMUNOLOGY, John Wiley & Sons, v. 1, pp. 2.5.1-2.6.7, 2.7.1-2.7.12, 2.8.1-2.8.10, 2.9.1-2.9.3 and 2.10.-2.10.4.

Conrad and Scheller, 2005, Comb. Chem. High Throughput Screen. 8:117-26.

Cossins et al. (2006, Prot Express Purif 51: 253-259.

Dang N H, Morimoto C. CD26: An expanding role in immune regulation and cancer. *Histol Histopathol* 2002, 17(4):1213-1226.

Dantas-Barbosa et al., 2005, Genet. Mol. Res. 4:126-40.

Dong et al. (1998), "Correlation of the Epitopes Defined by Anti-CD26 mAbs and CD26 Function", Molecular Immunology 35(1):13-21.

Dong et al. (1996) J Immunol. 156(4):1349-55.

Drucker D J. Dipeptidyl peptidase-4 inhibition and the treatment of type 2 diabetes. Diabetes Care 2007; 30: 1335-1341.

DuBois D; DuBois E F., Arch Int Med 1916 17:863-71.

Durinx C, Lambeir A M, Bosmans E et al. Molecular characterization of dipeptidylpeptidase activity in serum: soluble CD26/dipeptidylpeptidase IV is responsible for the release of X-Pro dipeptides. EurJ Biochem 2000; 267: 5608-5613.

Edelman et al. (1967) in Methods in enzymology, v. 1, p. 422.

Ferrara J L M, Levine J E, Reddy P and Holler E. *Graft-versus-Host Disease*. Lancet 2009; 373: 1550-1561.

Fleischer B, Sturm E, De-Vries J E, Spits H. Triggering of cytotoxic T lymphocytes and NK cells via the Tp103 pathway is dependent on the expression of the T cell receptor/CD3 complex. *J Immunol* 1988, 141:1103-1107.

Fleischer (1987) J. Immunol. 138, 1346-1350. Fleischer (1994) Immunol. Today 15:180-184.

Fox et al. (1984) J. Immunol. 133, 1250-1256.

Fraticelli P, Sironi M, Bianchi G, D'Ambrosio D, Albanesi C, Stoppacciaro A, Chieppa M, Allavena P, Ruco L, Girolomoni G, Sinigaglia F, Vecchi A, Mantovani A. Fractalkine (CX3CL1) as an amplification circuits of polarized Th1 responses. *J Clin Invest* 2001, 107(9):1173-1181.

Freshney R I, ed. (1987) Culture of Animal Cells, AR Liss Inc.

Gait M J, ed. (1984) Oligonucleotide Synthesis.

Glucksberg H, Storb R, Fefer A, et al. *Clinical manifestations of graft-versus-host disease in human recipients of marrow from HL-A-Matched sibling donors*. Transplantation 1974; 18: 295-304.

Green et al., Nature Genet. 7:13 (1994).

Green et al., 1999, J. Immunol. Methods 231:11-23.

Guo Y, Hangoc G, Bian H, Pelus L M, Broxmeyer H E. SDF-1/CXCL12 enhances survival and chemotaxis of murine embryonic stem cells and production of primitive and definitive hematopoietic progenitor cells. Stem Cells. 2005 October; 23(9):1324-32. Erratum in: Stem Cells. 2006 January; 24(1):211. PubMed PMID: 16210409.

Hames B D et al. (1984) Nucleic Acid Hybridization.

Hegen et al. (1990) J. Immunol. 144, 2908-2914.

Hogan B (1986) Manipulating the Mouse Embryo, Cold Spring Harbor Laboratory.

Hollinger et al., 1993, Proc. Natl. Acad Sci. USA 90: 6444-6448.

Hopsu-Havu and Glenner, 1966, Histochemie; 7: 197-201

Huse et al. (Science 1989, 246:1274-1281).

Inhibition of CD26 preserves pancreatic islet transplants through a pathway involving modulation of splenic CD4(+) T-cell migration in mice. *Diabetes* 2010; 59(7): 1739-50

Inhibition of CD26 down regulates activated T cells and prevents lung graft rejection in rats. *J Heart Lung Transplant* 2006; 25(9):1109-16

Inhibition of CD26 suppresses autoimmune encephalomyelitis (EAE) in mice. *J Immunol* 2001; 166(3): 2041-8

Jacobsohn D A and Vogelsang G B. *Acute graft versus host disease*. Orphanet Journal of Rare Diseases 2007; 2: 35-44.

Jee Y, Yoon W K, Okura Y, Tanuma N, Matsumoto Y. Upregulation of monocyte chemotactic protein-1 and CC chemokine receptor 2 in the central nervous system is closely associated with relapse of autoimmune encephalomyelitis in Lewis rats. *J Neuroimmunol* 2002, 128(1-2):49-57.

Jellinek et al., 1995, Biochem. 34:11363-11372.

Johnson and Chiswell, 1993, *Current Opinion in Structural Biology* 3:5564-571.

Jones et al., Nature 321: 522 (1986).

Kabat et al. (1991), Sequences of Proteins of Immunological Interest, 5. ed., Washington, D.C., Public Health Service, N.I.H.

Kahne T, Lendeckel U, Wrenger S et al. Dipeptidyl peptidase IV: a cell surface peptidase involved in regulating T cell growth (review). Int J Mol Med 1999; 4: 3-15.

Kameoka et al. (1993) Science. 261(5120):466-9.

Kawai, T., U. Choi, P. C. Liu, N. L. Whiting-Theobald, G. F. Linton and H. L. Malech (2007). Diprotin A Infusion into Nonobese Diabetic/Severe Combined Immunodeficiency Mice Markedly Enhances Engraftment of Human Mobilized CD34(+) Peripheral Blood Cells. Stem Cells Dev 16(3): 361-370.

Kobayashi et al., Protein Eng. 12(10):879-884 (1999).

Kobayashi et al., Protein Eng. 12(10):879-884 (1999).

Kohler and Milstein, Nature 256: 495 (1975).

Kostelny et al., 1992, J. Immunol. 148: 1547-1553.

Leung et al., Hybridoma 13:469 (1994).

Lewis, I. D. (2002). Clinical and experimental uses of umbilical cord blood. Intern Med J 32(12): 601-9.

Lin et al., 1994, Nucl. Acids Res. 22:5220-5234.

Lock C, Hermans G, Pedotti R, Brendolan A, Schadt E, Garren H, Langer-Gould A, Strober S, Cannella B, Allard J, Klonowski P, Austin A, Lad N, Kaminski N, Galli S J, Oksenberg J R, Raine C S, Heller R, Steinman L. Gene-microarray analysis of multiple sclerosis lesions yields new targets validated in autoimmune encephalomyelitis. *Nat Med* 2002, 8(5):500-508.

Lonberg et al., Nature 1994 368:856.

Maciejewski J P, Selleri C, Anderson S, Young N S. Fas antigen expression on CD34+ human marrow cells is induced by interferon gamma and tumor necrosis factor alpha and potentiates cytokine mediated hematopoietic suppression in vitro. *Blood* 1995, 85:3183-3190.
Maciejewski J P, Selleri C, Sato T, Anderson S, Young N S. Increased expression of Fas antigen on bone marrow CD34+ cells of patients with aplastic anemia. *Br J Haematol* 1995, 91:245-252.
Mancini et al., 2004, New Microbiol. 27:315-28.
Marks et al., 1991, J. Mol. Biol. 222:581-97.
Marks, J. D., et al., 1992, *J. Biol. Chem.* 267: 16007
Mayer and Walker, eds. (1987), Immunochemical Methods in Cell and Molecular Biology.
McCafferty et al., 1990, Nature 348:552-553.
Menthlein, 1999, Regulatory Peptides; 85: 9-24
Miller J H and Calos M P, eds. (1987) Gene Transfer Vectors for Mammalian Cells, Cold Spring Harbor Laboratory
Morimoto et al. (1989) J. Immunol. 143, 3430-3439.
Morimoto et al. (1994) Immunologist 2: 4-7.
Morrison et al. (1993) J Exp Med. 177(4):1135-43).
Mosteller R D., N Engl J Med 1987 Oct. 22; 317(17): 1098.
Nakao S, Takami A, Takamatsu H, Zeng W, Sugimori N, Yamazaki H, Miura Y, Ueda M, Shiobara S, Yoshioka T, Kaneshige T, Yasukawa M, Matsuda T. Isolation of a T cell clone showing HLADRB1*0405-restricted cytotoxicity for hematopoietic cells in a patient with aplastic anemia. *Blood* 1997, 89:3691-3699.
Nisonoff et al., Arch Biochem. Biophys. 89: 230 (1960).
Orlandi et al., 1989, Proc. Nat'l Acad. Sci. USA 86: 3833.
Pagratis et al., 1997, Nature Biotechnol. 15:68-73.
Pasqualini and Ruoslahti, 1996, Nature 380:364-366.
Pasqualini, 1999, The Quart. J. Nucl. Med. 43:159-162.
Perbal B (1984) A Practical Guide to Molecular Cloning, John Wiley & Sons Inc.
Peranteau W H, Endo M, Adibe O O et al. CD26 inhibition enhances allogeneic donor-cell homing and engraftment after in utero hematopoietic-cell transplantation. Blood 2006; 108: 4268-4274.
Porter, Biochem. J. 73: 119 (1959).
Raag R and Whitlow M, "Single Chain Fvs." FASEB Vol 9:73-80 (1995)
Riechmann et al., 1988, Nature 332: 323.
Risitano A M, Kook H, Zeng W, Chen G, Young N S, Maciejewski J P. Oligoclonal and polyclonal CD4 and CD8 lymphocytes in aplastic anemia and paroxysmal nocturnal hemoglobinuria measured by V beta CDR3 spectratyping and flow cytometry. *Blood* 2002, 100(1): 178-183.
Roig M G (1986) Immobilized Cells and Enzymes, IRL Press.
Sambrook et al., eds. (1989) Molecular Cloning: A Laboratory Manual, 2. ed.
Sandhu, 1992, Crit. Rev. Biotech. 12: 437.
Shier, R. et al., 1996, *Gene* 169: 147
Singer et al., 1993, J. Immun. 150: 2844.
Songsivilai et al., 1990, Clin. Exp. Immunol. 79: 315-321.
Sun Y, Tawara I, Tubai T, and Reddy P. *Pathophysiology of Acute Graft-vs-Host Disease: Recent Advances. Transl Res.* 2007; 150: 197-214.
Taylor et al., Int. Immun. 1994 6:579.
Tempest et al., 1991, Biotechnology 9:266.
Tian, C., J. Bagley, D. Forman and J. Iacomini (2006). "Inhibition of CD26 peptidase activity significantly improves engraftment of retrovirally transduced hematopoietic progenitors." Gene Ther 13(7): 652-8.
Timmerman et al., 2007, J. Mol. Recognit. 20: 283-290
Ulmer et al. (1990) J. Immunol. 31, 429-435.
US 2010/0196266 A1, EP 404 097, WO 93/11161, Goldenberg, U.S. Pat. Nos. 4,036,945 and 4,331,647, 4,704,692, 4,946,778, 5,545,807, 5,545,806, 5,633,425, 5,661,016, 5,567,610, 5,229,275, EP 1 241 179 B1, U.S. Pat. No. 4,683,195 (Mullis et al.), U.S. Pat. Nos. 7,863,239, 7,972,993, 7,982,013 B2.
Vanham G, Kestens L, Demeester I et al. Decreased expression of the memory marker CD26 on both CD4+ and CD8+ T lymphocytes of HIV infected subjects. J Acquir Immune Defic Syndr 1993; 6: 749-757.
Verhoeyen et al., 1988, Science 239: 1534.
Weir D M and Blackwell C C, eds. (1986) Handbook of Experiment Immunology, w. I-IV
Willheim M, Ebner C, Baier K, Kern W, Schrattbauer K, Thien R, Kraft D, Breiteneder H, Reinisch W, Scheiner O. Cell surface characterization of T lymphocytes and allergen-specific T cell clones—correlation of CD26 expression with Th1 subsets. *J Allergy Clin Immunol* 1997, 100:348-255.
Wu (1986) in Methods in enzymology, v. 154, preface.
Wu (1987) in Methods in enzymology, v. 155, preface.
Young N S, Maciejewski J P. The pathophysiology of acquired aplastic anemia. *N Eng J Med* 1997, 336: 1365-1372.
Zeng W, Nakao S, Takamatsu H, Yachie A, Takami A, Kondo Y, Sugimori N, Yamazaki H, Miura Y, Shiobara S, Matsuda T. Characterization of T-cell repertoire of the bone marrow in immunemediated aplastic anemia: Evidence for the involvement of antigen-driven T-cell response in cyclosporine-dependent aplastic anemia. *Blood* 1999, 93(9):3008-3016.
Zeng W, Maciejewski J P, Chen G, Young N S. Limited heterogeneity of T cell receptor BV usage in aplastic anemia. *J Clin Invest* 2001, 108(5):765-773.

The invention claimed is:

1. An isolated monoclonal antibody that specifically binds CD26, which is capable of binding a CD26 epitope comprising the amino acids Asp329, Asn338, Leu340, Val341, Ala342, Arg343, Asp367, Asn369, Tyr386, Gln388, Ile389, Asp390, Lys391, Lys392, Asp393, Thr395, Ser412, Leu436, Ser437, Asp438 and Tyr439 of SEQ ID NO: 144 or a corresponding sequence, wherein the antibody comprises a VH CDR1 comprising the sequence of SEQ ID NO: 133, a VH CDR2 comprising the sequence of SEQ ID NO: 134, and a VH CDR3 comprising the sequence of SEQ ID NO: 1; and the light chain variable region comprises a VL CDR1 comprising the sequence of SEQ ID NO: 129, a VL CDR2 comprising the sequence of SEQ ID NO: 130, and a VL CDR3 comprising the sequence of SEQ ID NO: 2.

2. The antibody of claim 1, wherein the light chain variable region comprises an amino acid sequence having at least 90% sequence identity to SEQ ID NO: 4.

3. The antibody of claim 1, wherein the heavy chain variable region comprises an amino acid sequence having at least 90% sequence identity to SEQ ID NO: 26.

4. The antibody of claim 1, wherein the light chain variable region comprises an amino acid sequence selected from the group consisting of SEQ ID NO:4 and SEQ ID NO: 6 to 21, and the heavy chain variable region comprises an amino acid sequence selected from the group consisting of SEQ ID NO: 22 to 47.

5. The antibody of claim 4, wherein the light chain variable region comprises the amino acid sequence of SEQ ID NO: 4, and the heavy chain variable region comprises the amino acid sequence of SEQ ID NO: 26.

6. The antibody of claim 1, wherein the antibody has an antibody isotype selected from the group consisting of IgG1, IgG2, IgG3, IgG4, IgM, IgA, IgD and IgE.

7. The antibody of claim 1, wherein the antibody has an antibody isotype of IgG 2B class.

8. The antibody of claim 1, wherein the antibody is a recombinant antibody, a chimeric antibody, a humanized antibody, a human antibody, an antibody fragment, a bispecific antibody, a monospecific antibody, or a monovalent antibody.

9. A method of promoting engraftment after haematopoietic stem cell transplantation (HSCT), preventing or treating Graft-versus-Host Disease (GvHD), and/or treating Aplastic Anemia in a subject in need thereof, comprising administering a therapeutically effective dose of a monoclonal antibody which is capable of binding a CD26 epitope comprising the amino acids Asp329, Asn338, Leu340, Val341, Ala342, Arg343, Asp367, Asn369, Tyr386, Gln388, Ile389, Asp390, Lys391, Lys392, Asp393, Thr395, Ser412, Leu436, Ser437, Asp438 and Tyr439 of SEQ ID NO: 144 or a corresponding sequence, wherein the antibody comprises a VH CDR1 comprising the sequence of SEQ ID NO: 133, a VH CDR2 comprising the sequence of SEQ ID NO: 134, and a VH CDR3 comprising the sequence of SEQ ID NO: 1; and the light chain variable region comprises a VL CDR1 comprising the sequence of SEQ ID NO: 129, a VL CDR2 comprising the sequence of SEQ ID NO: 130, and a VL CDR3 comprising the sequence of SEQ ID NO: 2.

10. The method of claim 9, wherein the light chain variable region comprises an amino acid sequence having at least 90% sequence identity to SEQ ID NO: 4.

11. The method of claim 9, wherein the heavy chain variable region comprises an amino acid sequence having at least 90% sequence identity to SEQ ID NO: 26.

12. The method of claim 9, wherein the light chain variable region comprises an amino acid sequence selected from the group consisting of SEQ ID NO: 4 and SEQ ID NO: 6 to 21, and the heavy chain variable region comprises an amino acid sequence selected from the group consisting of SEQ ID NO: 22 to 47.

13. The method of claim 12, wherein the light chain variable region comprises the amino acid sequence of SEQ ID NO: 4, and the heavy chain variable region comprises the amino acid sequence of SEQ ID NO: 26.

14. The method of claim 9, wherein the antibody has an antibody isotype selected from the group consisting of IgG1, IgG2, IgG3, IgG4, IgM, IgA, IgD and IgE.

15. The method of claim 9, wherein the antibody has an antibody isotype of IgG 2B class.

16. The method of claim 9, wherein the antibody is a recombinant antibody, a chimeric antibody, a humanized antibody, a human antibody, an antibody fragment, a bispecific antibody, a monospecific antibody, or a monovalent antibody.

17. The method of claim 9, wherein the antibody is a humanized antibody.

* * * * *

SEQUENCE LISTING

```
<160> NUMBER OF SEQ ID NOS: 159

<210> SEQ ID NO 1
<211> LENGTH: 11
<212> TYPE: PRT
<213> ORGANISM: Artificial Sequence
<220> FEATURE:
<223> OTHER INFORMATION: CDR-H3 Heavy

<400> SEQUENCE: 1

Trp Thr Val Val Gly Pro Gly Tyr Phe Asp Val
```

1 5 10

<210> SEQ ID NO 2
<211> LENGTH: 9
<212> TYPE: PRT
<213> ORGANISM: Artificial Sequence
<220> FEATURE:
<223> OTHER INFORMATION: CDR-L3 Light Group1

<400> SEQUENCE: 2

Gln Gln Arg Ser Ser Tyr Pro Asn Thr
1 5

<210> SEQ ID NO 3
<211> LENGTH: 9
<212> TYPE: PRT
<213> ORGANISM: Artificial Sequence
<220> FEATURE:
<223> OTHER INFORMATION: CDR-L3 Light Group3

<400> SEQUENCE: 3

Gly Gln Gly Tyr Ser Tyr Pro Tyr Thr
1 5

<210> SEQ ID NO 4
<211> LENGTH: 106
<212> TYPE: PRT
<213> ORGANISM: Artificial Sequence
<220> FEATURE:
<223> OTHER INFORMATION: VL prevalent group 1

<400> SEQUENCE: 4

Gln Ile Val Leu Thr Gln Ser Pro Ala Ile Met Ser Ala Ser Pro Gly
1 5 10 15

Glu Lys Val Thr Ile Thr Cys Ser Ala Ser Ser Ser Val Ser Tyr Met
20 25 30

Asn Trp Phe Gln Gln Lys Pro Gly Thr Ser Pro Lys Leu Trp Ile Tyr
35 40 45

Ser Thr Ser Asn Leu Ala Ser Gly Val Pro Ala Arg Phe Ser Gly Ser
50 55 60

Gly Ser Gly Thr Ser Tyr Ser Leu Thr Ile Ser Arg Met Glu Ala Glu
65 70 75 80

Asp Ala Ala Thr Tyr Tyr Cys Gln Gln Arg Ser Ser Tyr Pro Asn Thr
85 90 95

Phe Gly Gly Gly Thr Lys Leu Glu Ile Lys
100 105

<210> SEQ ID NO 5
<211> LENGTH: 108
<212> TYPE: PRT
<213> ORGANISM: Artificial Sequence
<220> FEATURE:
<223> OTHER INFORMATION: VL group 3

<400> SEQUENCE: 5

Asp Ile Val Met Thr Gln Ser Pro Lys Ser Met Ser Met Ser Val Gly
1 5 10 15

Glu Arg Val Thr Leu Thr Cys Lys Ala Ser Glu Asn Val Val Thr Tyr
20 25 30

Val Ser Trp Tyr Gln Gln Lys Pro Glu Gln Ser Pro Lys Leu Leu Ile
35 40 45

Tyr Gly Ala Ser Asn Arg Tyr Thr Gly Val Pro Asp Arg Phe Thr Gly

```
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg
            100                 105


<210> SEQ ID NO 6
<211> LENGTH: 107
<212> TYPE: PRT
<213> ORGANISM: Artificial Sequence
<220> FEATURE:
<223> OTHER INFORMATION: VL group 1

<400> SEQUENCE: 6

Asp Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Leu Lys Arg
            100                 105


<210> SEQ ID NO 7
<211> LENGTH: 107
<212> TYPE: PRT
<213> ORGANISM: Artificial Sequence
<220> FEATURE:
<223> OTHER INFORMATION: VL group 1

<400> SEQUENCE: 7

Asp Ile Glu Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Ile Asn Val
            100                 105


<210> SEQ ID NO 8
<211> LENGTH: 107
<212> TYPE: PRT
<213> ORGANISM: Artificial Sequence
<220> FEATURE:
```

<223> OTHER INFORMATION: VL group 1

<400> SEQUENCE: 8

```
Asp Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Ile Lys Arg
            100                 105
```

<210> SEQ ID NO 9
<211> LENGTH: 107
<212> TYPE: PRT
<213> ORGANISM: Artificial Sequence
<220> FEATURE:
<223> OTHER INFORMATION: VL group 1

<400> SEQUENCE: 9

```
Asp Ile Val Met Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Ile Lys Arg
            100                 105
```

<210> SEQ ID NO 10
<211> LENGTH: 107
<212> TYPE: PRT
<213> ORGANISM: Artificial Sequence
<220> FEATURE:
<223> OTHER INFORMATION: VL group 1

<400> SEQUENCE: 10

```
Asp Ile Val Met Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
```

```
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Leu Lys Arg
            100                 105


<210> SEQ ID NO 11
<211> LENGTH: 107
<212> TYPE: PRT
<213> ORGANISM: Artificial Sequence
<220> FEATURE:
<223> OTHER INFORMATION: VL group 1

<400> SEQUENCE: 11

Asp Ile Gln Met Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Cys Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Ile Lys Arg
            100                 105


<210> SEQ ID NO 12
<211> LENGTH: 107
<212> TYPE: PRT
<213> ORGANISM: Artificial Sequence
<220> FEATURE:
<223> OTHER INFORMATION: VL group 1

<400> SEQUENCE: 12

Asp Ile Lys Ile Asn Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Ile Lys Arg
            100                 105


<210> SEQ ID NO 13
<211> LENGTH: 107
<212> TYPE: PRT
<213> ORGANISM: Artificial Sequence
<220> FEATURE:
<223> OTHER INFORMATION: VL group 1

<400> SEQUENCE: 13
```

Asp Ile Gln Met Thr Gln Ser Pro Ala Ile Met Ser Ala Ser Pro Gly
1 5 10 15

Glu Lys Val Thr Ile Thr Cys Ser Ala Ser Ser Ser Val Ser Tyr Met
20 25 30

Asn Trp Phe Gln Gln Lys Pro Gly Thr Ser Pro Lys Leu Trp Ile Tyr
35 40 45

Ser Thr Ser Asn Leu Ala Ser Gly Val Pro Ala Arg Phe Ser Gly Ser
50 55 60

Gly Ser Gly Thr Ser Tyr Ser Leu Thr Ile Ser Arg Met Glu Ala Glu
65 70 75 80

Asp Ala Ala Thr Tyr Tyr Cys Gln Gln Arg Ser Ser Tyr Pro Asn Thr
85 90 95

Phe Gly Gly Gly Thr Lys Leu Glu Ile Lys Arg
100 105

<210> SEQ ID NO 14
<211> LENGTH: 107
<212> TYPE: PRT
<213> ORGANISM: Artificial Sequence
<220> FEATURE:
<223> OTHER INFORMATION: VL group 1

<400> SEQUENCE: 14

Asp Ile Gln Met Ile Gln Ser Pro Ala Ile Met Ser Ala Ser Pro Gly
1 5 10 15

Glu Lys Val Thr Ile Thr Cys Ser Ala Ser Ser Ser Val Ser Tyr Met
20 25 30

Asn Trp Phe Gln Gln Lys Pro Gly Thr Ser Pro Lys Leu Trp Ile Tyr
35 40 45

Ser Thr Ser Asn Leu Ala Ser Gly Val Pro Ala Arg Phe Ser Gly Ser
50 55 60

Gly Ser Gly Thr Ser Tyr Ser Leu Thr Ile Ser Arg Met Glu Ala Glu
65 70 75 80

Asp Ala Ala Thr Tyr Tyr Cys Gln Gln Arg Ser Ser Tyr Pro Asn Thr
85 90 95

Phe Gly Gly Gly Thr Lys Leu Glu Ile Lys Arg
100 105

<210> SEQ ID NO 15
<211> LENGTH: 107
<212> TYPE: PRT
<213> ORGANISM: Artificial Sequence
<220> FEATURE:
<223> OTHER INFORMATION: VL group 1

<400> SEQUENCE: 15

Asp Ile Leu Leu Thr Gln Ser Pro Ala Ile Met Ser Ala Ser Pro Gly
1 5 10 15

Glu Lys Val Thr Ile Thr Cys Ser Ala Ser Ser Ser Val Ser Tyr Met
20 25 30

Asn Trp Phe Gln Gln Lys Pro Gly Thr Ser Pro Lys Leu Trp Ile Tyr
35 40 45

Ser Thr Ser Asn Leu Ala Ser Gly Val Pro Ala Arg Phe Ser Gly Ser
50 55 60

Gly Ser Gly Thr Ser Tyr Ser Leu Thr Ile Ser Arg Met Glu Ala Glu
65 70 75 80

Asp Ala Ala Thr Tyr Tyr Cys Gln Gln Arg Ser Ser Tyr Pro Asn Thr

```
                85                  90                  95

Phe Gly Gly Gly Thr Lys Leu Glu Ile Lys Arg
            100                 105


<210> SEQ ID NO 16
<211> LENGTH: 107
<212> TYPE: PRT
<213> ORGANISM: Artificial Sequence
<220> FEATURE:
<223> OTHER INFORMATION: VL group 1

<400> SEQUENCE: 16

Asp Ile Gln Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Ile Lys Arg
            100                 105


<210> SEQ ID NO 17
<211> LENGTH: 107
<212> TYPE: PRT
<213> ORGANISM: Artificial Sequence
<220> FEATURE:
<223> OTHER INFORMATION: VL group 1

<400> SEQUENCE: 17

Asp Ile Leu Met Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Ile Lys Arg
            100                 105


<210> SEQ ID NO 18
<211> LENGTH: 107
<212> TYPE: PRT
<213> ORGANISM: Artificial Sequence
<220> FEATURE:
<223> OTHER INFORMATION: VL group 1
<220> FEATURE:
<221> NAME/KEY: misc_feature
<222> LOCATION: (4)..(4)
<223> OTHER INFORMATION: Ile or Met
```

<400> SEQUENCE: 18

```
Asp Ile Leu Xaa Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Leu Lys Arg
            100                 105
```

<210> SEQ ID NO 19
<211> LENGTH: 107
<212> TYPE: PRT
<213> ORGANISM: Artificial Sequence
<220> FEATURE:
<223> OTHER INFORMATION: VL group 1

<400> SEQUENCE: 19

```
Asp Val Leu Met Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Ile Lys Arg
            100                 105
```

<210> SEQ ID NO 20
<211> LENGTH: 107
<212> TYPE: PRT
<213> ORGANISM: Artificial Sequence
<220> FEATURE:
<223> OTHER INFORMATION: VL group 1

<400> SEQUENCE: 20

```
Asp Ile Val Met Thr Gln Thr Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80
```

```
Asp Ala Ala Thr Tyr Tyr Cys Gln Gln Arg Ser Ser Tyr Pro Asn Thr
                85                  90                  95

Phe Gly Gly Gly Thr Lys Leu Glu Ile Lys Arg
            100                 105


<210> SEQ ID NO 21
<211> LENGTH: 107
<212> TYPE: PRT
<213> ORGANISM: Artificial Sequence
<220> FEATURE:
<223> OTHER INFORMATION: VL group 1

<400> SEQUENCE: 21

Asp Val Leu Met Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

Asn Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Asn Thr
                85                  90                  95

Phe Gly Gly Gly Thr Lys Leu Glu Leu Lys Arg
            100                 105


<210> SEQ ID NO 22
<211> LENGTH: 120
<212> TYPE: PRT
<213> ORGANISM: Artificial Sequence
<220> FEATURE:
<223> OTHER INFORMATION: VH group 1

<400> SEQUENCE: 22

Glu Val Lys Leu Gln Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 23
<211> LENGTH: 120
<212> TYPE: PRT
<213> ORGANISM: Artificial Sequence
<220> FEATURE:
<223> OTHER INFORMATION: VH group 1
```

<400> SEQUENCE: 23

Glu Val Lys Leu Val Glu Ser Gly Ala Glu Leu Val Lys Pro Gly Ala
1 5 10 15

Ser Val Lys Leu Ser Cys Lys Ala Ser Gly Tyr Thr Phe Arg Ser Tyr
20 25 30

Asp Ile Asn Trp Val Arg Gln Arg Pro Glu Gln Gly Leu Glu Trp Ile
35 40 45

Gly Trp Ile Phe Pro Gly Asp Gly Ser Thr Lys Tyr Asn Glu Lys Phe
50 55 60

Lys Gly Lys Ala Thr Leu Thr Thr Asp Lys Ser Ser Ser Thr Ala Tyr
65 70 75 80

Met Gln Leu Ser Arg Leu Thr Ser Glu Asp Ser Ala Val Tyr Phe Cys
85 90 95

Ala Arg Trp Thr Val Val Gly Pro Gly Tyr Phe Asp Val Trp Gly Ala
100 105 110

Gly Thr Thr Val Thr Val Ser Ser
115 120

<210> SEQ ID NO 24
<211> LENGTH: 120
<212> TYPE: PRT
<213> ORGANISM: Artificial Sequence
<220> FEATURE:
<223> OTHER INFORMATION: VH group 1

<400> SEQUENCE: 24

Glu Val Gln Leu Gln Gln Ser Gly Ala Glu Leu Val Lys Pro Gly Ala
1 5 10 15

Ser Val Lys Leu Ser Cys Lys Ala Ser Gly Tyr Thr Phe Arg Ser Tyr
20 25 30

Asp Ile Asn Trp Val Arg Gln Arg Pro Glu Gln Gly Leu Glu Trp Ile
35 40 45

Gly Trp Ile Phe Pro Gly Asp Gly Ser Thr Lys Tyr Asn Glu Lys Phe
50 55 60

Lys Gly Lys Ala Thr Leu Thr Thr Asp Lys Ser Ser Ser Thr Ala Tyr
65 70 75 80

Met Gln Leu Ser Arg Leu Thr Ser Glu Asp Ser Ala Val Tyr Phe Cys
85 90 95

Ala Arg Trp Thr Val Val Gly Pro Gly Tyr Phe Asp Val Trp Gly Ala
100 105 110

Gly Thr Thr Val Thr Val Ser Ser
115 120

<210> SEQ ID NO 25
<211> LENGTH: 120
<212> TYPE: PRT
<213> ORGANISM: Artificial Sequence
<220> FEATURE:
<223> OTHER INFORMATION: VH group 1

<400> SEQUENCE: 25

Glu Val Gln Gly Val Glu Ser Gly Ala Glu Leu Val Lys Pro Gly Ala
1 5 10 15

Ser Val Lys Leu Ser Cys Lys Ala Ser Gly Tyr Thr Phe Arg Ser Tyr
20 25 30

Asp Ile Asn Trp Val Arg Gln Arg Pro Glu Gln Gly Leu Glu Trp Ile
35 40 45

Gly Trp Ile Phe Pro Gly Asp Gly Ser Thr Lys Tyr Asn Glu Lys Phe
50 55 60

Lys Gly Lys Ala Thr Leu Thr Thr Asp Lys Ser Ser Ser Thr Ala Tyr
65 70 75 80

Met Gln Leu Ser Arg Leu Thr Ser Glu Asp Ser Ala Val Tyr Phe Cys
85 90 95

Ala Arg Trp Thr Val Val Gly Pro Gly Tyr Phe Asp Val Trp Gly Ala
100 105 110

Gly Thr Thr Val Thr Val Ser Ser
115 120

<210> SEQ ID NO 26
<211> LENGTH: 120
<212> TYPE: PRT
<213> ORGANISM: Artificial Sequence
<220> FEATURE:
<223> OTHER INFORMATION: VH group 1

<400> SEQUENCE: 26

Gln Val Gln Leu Gln Gln Ser Gly Ala Glu Leu Val Lys Pro Gly Ala
1 5 10 15

Ser Val Lys Leu Ser Cys Lys Ala Ser Gly Tyr Thr Phe Arg Ser Tyr
20 25 30

Asp Ile Asn Trp Val Arg Gln Arg Pro Glu Gln Gly Leu Glu Trp Ile
35 40 45

Gly Trp Ile Phe Pro Gly Asp Gly Ser Thr Lys Tyr Asn Glu Lys Phe
50 55 60

Lys Gly Lys Ala Thr Leu Thr Thr Asp Lys Ser Ser Ser Thr Ala Tyr
65 70 75 80

Met Gln Leu Ser Arg Leu Thr Ser Glu Asp Ser Ala Val Tyr Phe Cys
85 90 95

Ala Arg Trp Thr Val Val Gly Pro Gly Tyr Phe Asp Val Trp Gly Ala
100 105 110

Gly Thr Thr Val Thr Val Ser Ser
115 120

<210> SEQ ID NO 27
<211> LENGTH: 120
<212> TYPE: PRT
<213> ORGANISM: Artificial Sequence
<220> FEATURE:
<223> OTHER INFORMATION: VH group 1

<400> SEQUENCE: 27

Glu Val Gln Leu Gln Glu Ser Gly Ala Glu Leu Val Lys Pro Gly Ala
1 5 10 15

Ser Val Lys Leu Ser Cys Lys Ala Ser Gly Tyr Thr Phe Arg Ser Tyr
20 25 30

Asp Ile Asn Trp Val Arg Gln Arg Pro Glu Gln Gly Leu Glu Trp Ile
35 40 45

Gly Trp Ile Phe Pro Gly Asp Gly Ser Thr Lys Tyr Asn Glu Lys Phe
50 55 60

Lys Gly Lys Ala Thr Leu Thr Thr Asp Lys Ser Ser Ser Thr Ala Tyr
65 70 75 80

Met Gln Leu Ser Arg Leu Thr Ser Glu Asp Ser Ala Val Tyr Phe Cys
85 90 95

Ala Arg Trp Thr Val Val Gly Pro Gly Tyr Phe Asp Val Trp Gly Ala
100 105 110

```
Gly Thr Thr Val Thr Val Ser Ser
        115                 120


<210> SEQ ID NO 28
<211> LENGTH: 120
<212> TYPE: PRT
<213> ORGANISM: Artificial Sequence
<220> FEATURE:
<223> OTHER INFORMATION: VH group 1

<400> SEQUENCE: 28

Gln Val Gln Leu Gln Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 29
<211> LENGTH: 120
<212> TYPE: PRT
<213> ORGANISM: Artificial Sequence
<220> FEATURE:
<223> OTHER INFORMATION: VH group 1

<400> SEQUENCE: 29

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Leu Thr Val Ser Ser
        115                 120


<210> SEQ ID NO 30
<211> LENGTH: 120
<212> TYPE: PRT
<213> ORGANISM: Artificial Sequence
<220> FEATURE:
<223> OTHER INFORMATION: VH group 1
```

<400> SEQUENCE: 30

```
Gln Val Lys Leu Gln Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120
```

<210> SEQ ID NO 31
<211> LENGTH: 120
<212> TYPE: PRT
<213> ORGANISM: Artificial Sequence
<220> FEATURE:
<223> OTHER INFORMATION: VH group 1

<400> SEQUENCE: 31

```
Glu Val Lys Leu Gln Gln Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120
```

<210> SEQ ID NO 32
<211> LENGTH: 120
<212> TYPE: PRT
<213> ORGANISM: Artificial Sequence
<220> FEATURE:
<223> OTHER INFORMATION: VH group 1

<400> SEQUENCE: 32

```
Glu Val Lys Val Val Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45
```

```
Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 33
<211> LENGTH: 120
<212> TYPE: PRT
<213> ORGANISM: Artificial Sequence
<220> FEATURE:
<223> OTHER INFORMATION: VH group 1

<400> SEQUENCE: 33

Asp Val Gln Leu Gln Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 34
<211> LENGTH: 120
<212> TYPE: PRT
<213> ORGANISM: Artificial Sequence
<220> FEATURE:
<223> OTHER INFORMATION: VH group 1

<400> SEQUENCE: 34

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
```

```
            100                 105                 110

Gly Thr Pro Val Thr Val Ser Ser
        115                 120


<210> SEQ ID NO 35
<211> LENGTH: 120
<212> TYPE: PRT
<213> ORGANISM: Artificial Sequence
<220> FEATURE:
<223> OTHER INFORMATION: VH group 1

<400> SEQUENCE: 35

Gln Val Gln Leu Lys Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 36
<211> LENGTH: 120
<212> TYPE: PRT
<213> ORGANISM: Artificial Sequence
<220> FEATURE:
<223> OTHER INFORMATION: VH group 1

<400> SEQUENCE: 36

Glu Val Met Leu Val Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 37
<211> LENGTH: 120
<212> TYPE: PRT
<213> ORGANISM: Artificial Sequence
<220> FEATURE:
```

```
<223> OTHER INFORMATION: VH group 1
<220> FEATURE:
<221> NAME/KEY: misc_feature
<222> LOCATION: (3)..(3)
<223> OTHER INFORMATION: Leu or Glu

<400> SEQUENCE: 37

Glu Val Xaa Leu Val Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 38
<211> LENGTH: 120
<212> TYPE: PRT
<213> ORGANISM: Artificial Sequence
<220> FEATURE:
<223> OTHER INFORMATION: VH group 1

<400> SEQUENCE: 38

Asp Val Lys Leu Gln Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 39
<211> LENGTH: 120
<212> TYPE: PRT
<213> ORGANISM: Artificial Sequence
<220> FEATURE:
<223> OTHER INFORMATION: VH group 1

<400> SEQUENCE: 39

Glu Val Gln Leu Val Glu Ser Gly Ala Glu Leu Val Lys Pro Gly Ala
1               5                   10                  15
```

```
Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 40
<211> LENGTH: 120
<212> TYPE: PRT
<213> ORGANISM: Artificial Sequence
<220> FEATURE:
<223> OTHER INFORMATION: VH group 1

<400> SEQUENCE: 40

Glu Val Gln Leu Val Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Ser Val Thr Val Ser Ser
        115                 120


<210> SEQ ID NO 41
<211> LENGTH: 120
<212> TYPE: PRT
<213> ORGANISM: Artificial Sequence
<220> FEATURE:
<223> OTHER INFORMATION: VH group 1

<400> SEQUENCE: 41

Glu Val Gln Leu His Gln Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80
```

```
Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 42
<211> LENGTH: 120
<212> TYPE: PRT
<213> ORGANISM: Artificial Sequence
<220> FEATURE:
<223> OTHER INFORMATION: VH group 1

<400> SEQUENCE: 42

Glu Val Lys Leu Met Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 43
<211> LENGTH: 120
<212> TYPE: PRT
<213> ORGANISM: Artificial Sequence
<220> FEATURE:
<223> OTHER INFORMATION: VH group 1
<220> FEATURE:
<221> NAME/KEY: misc_feature
<222> LOCATION: (1)..(1)
<223> OTHER INFORMATION: Glu, Gln or Lys
<220> FEATURE:
<221> NAME/KEY: misc_feature
<222> LOCATION: (6)..(6)
<223> OTHER INFORMATION: Glu, Gln or Lys

<400> SEQUENCE: 43

Xaa Val Gln Leu Gln Xaa Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95
```

```
Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 44
<211> LENGTH: 120
<212> TYPE: PRT
<213> ORGANISM: Artificial Sequence
<220> FEATURE:
<223> OTHER INFORMATION: VH group 1

<400> SEQUENCE: 44

Glu Val Lys Val Val Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Ser Val Thr Val Ser Ser
        115                 120


<210> SEQ ID NO 45
<211> LENGTH: 120
<212> TYPE: PRT
<213> ORGANISM: Artificial Sequence
<220> FEATURE:
<223> OTHER INFORMATION: VH group 1

<400> SEQUENCE: 45

Glu Val Gln Leu Lys Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120


<210> SEQ ID NO 46
<211> LENGTH: 120
<212> TYPE: PRT
```

<213> ORGANISM: Artificial Sequence
<220> FEATURE:
<223> OTHER INFORMATION: VH group 1
<220> FEATURE:
<221> NAME/KEY: misc_feature
<222> LOCATION: (113)..(113)
<223> OTHER INFORMATION: Arg or Trp

<400> SEQUENCE: 46

```
Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Xaa Thr Thr Val Thr Val Ser Ser
        115                 120
```

<210> SEQ ID NO 47
<211> LENGTH: 120
<212> TYPE: PRT
<213> ORGANISM: Artificial Sequence
<220> FEATURE:
<223> OTHER INFORMATION: VH group 1

<400> SEQUENCE: 47

```
Glu Val Gln Arg Val Glu Ser Gly Ala Glu Leu Val Lys Pro Gly Ala
1               5                   10                  15

Ser Val Lys Leu Ser Cys Lys Ala Ser Gly Tyr Thr Phe Arg Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Trp Thr Val Val Gly Pro Gly Tyr Phe Asp Val Trp Gly Ala
            100                 105                 110

Gly Thr Thr Val Thr Val Ser Ser
        115                 120
```

<210> SEQ ID NO 48
<211> LENGTH: 107
<212> TYPE: PRT
<213> ORGANISM: Artificial Sequence
<220> FEATURE:
<223> OTHER INFORMATION: CL

<400> SEQUENCE: 48

```
Arg Ala Asp Ala Ala Pro Thr Val Ser Ile Phe Pro Pro Ser Ser Glu
```

```
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 49
<211> LENGTH: 336
<212> TYPE: PRT
<213> ORGANISM: Artificial Sequence
<220> FEATURE:
<223> OTHER INFORMATION: CH1-CH2-CH3

<400> SEQUENCE: 49

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
    130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
    210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
```

-continued

```
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335
```

<210> SEQ ID NO 50
<211> LENGTH: 318
<212> TYPE: DNA
<213> ORGANISM: Artificial Sequence
<220> FEATURE:
<223> OTHER INFORMATION: VL prevalent group 1

<400> SEQUENCE: 50

```
caaattgttc tcacccagtc tccagcaatc atgtctgcat ctccagggga gaaggtcacc     60

ataacctgca gtgccagctc aagtgtaagt tacatgaact ggttccagca gaagccaggc    120

acttctccca aactctggat ttatagcacc tccaacctgg cttctggagt ccctgctcgc    180

ttcagtggca gtggatctgg gacctcttac tctctcacaa tcagccgaat ggaggctgaa    240

gatgctgcca cttattactg ccagcaaagg agtagttacc cgaacacgtt cggagggggg    300

accaagctgg aaataaaa                                                  318
```

<210> SEQ ID NO 51
<211> LENGTH: 324
<212> TYPE: DNA
<213> ORGANISM: Artificial Sequence
<220> FEATURE:
<223> OTHER INFORMATION: VL group 3

<400> SEQUENCE: 51

```
gacattgtaa tgacccaatc tcccaaatcc atgtccatgt cagtaggaga gagggtcacc     60

ttgacctgca aggccagtga gaatgtggtt acttatgttt cctggtatca acagaaacca    120

gagcagtctc ctaaactgct gatatacggg gcatccaacc ggtacactgg ggtccccgat    180

cgcttcacag gcagtggatc tgcaacagat ttcactctga ccatcagcag tgtgcaggct    240

gaagaccttg cagattatca ctgtggacag ggttacagct atccgtacac gttcggaggg    300

gggaccaagc tggaaataaa acgt                                           324
```

<210> SEQ ID NO 52
<211> LENGTH: 321
<212> TYPE: DNA
<213> ORGANISM: Artificial Sequence
<220> FEATURE:
<223> OTHER INFORMATION: VL group 1

<400> SEQUENCE: 52

```
gatattgtgc tgacccagtc tccagcaatc atgtctgcat ctccagggga gaaggtcacc     60

ataacctgca gtgccagctc aagtgtaagt tacatgaact ggttccagca gaagccaggc    120

acttctccca aactctggat ttatagcacc tccaacctgg cttctggagt ccctgctcgc    180

ttcagtggca gtggatctgg gacctcttac tctctcacaa tcagccgaat ggaggctgaa    240

gatgctgcca cttattactg ccagcaaagg agtagttacc cgaacacgtt cggagggggg    300

accaagctgg agctgaaacg t                                              321
```

```
<210> SEQ ID NO 53
<211> LENGTH: 320
<212> TYPE: DNA
<213> ORGANISM: Artificial Sequence
<220> FEATURE:
<223> OTHER INFORMATION: VL group 1

<400> SEQUENCE: 53

gacattgagc tcacccagtc tccagcaatc atgtctgcat ctccagggga gaaggtcacc     60

ataacctgca gtgccagctc aagtgtaagt tacatgaact ggttccagca gaagccaggc    120

acttctccca aactctggat ttatagcacc tccaacctgg cttctggagt ccctgctcgc    180

ttcagtggca gtggatctgg gacctcttac tctctcacaa tcagccgaat ggaggctgaa    240

gatgctgcca cttattactg ccagcaaagg agtagttacc cgaacacgtt cggagggggg    300

accaagctgg aaataaacgt                                                320


<210> SEQ ID NO 54
<211> LENGTH: 321
<212> TYPE: DNA
<213> ORGANISM: Artificial Sequence
<220> FEATURE:
<223> OTHER INFORMATION: VL group 1

<400> SEQUENCE: 54

gatattgtgt tgacacagtc tccagcaatc atgtctgcat ctccagggga gaaggtcacc     60

ataacctgca gtgccagctc aagtgtaagt tacatgaact ggttccagca gaagccaggc    120

acttctccca aactctggat ttatagcacc tccaacctgg cttctggagt ccctgctcgc    180

ttcagtggca gtggatctgg gacctcttac tctctcacaa tcagccgaat ggaggctgaa    240

gatgctgcca cttattactg ccagcaaagg agtagttacc cgaacacgtt cggagggggg    300

accaagctgg aaataaaacg t                                              321


<210> SEQ ID NO 55
<211> LENGTH: 321
<212> TYPE: DNA
<213> ORGANISM: Artificial Sequence
<220> FEATURE:
<223> OTHER INFORMATION: VL group 1

<400> SEQUENCE: 55

gacattgtgc tgacacagtc tccagcaatc atgtctgcat ctccagggga gaaggtcacc     60

ataacctgca gtgccagctc aagtgtaagt tacatgaact ggttccagca gaagccaggc    120

acttctccca aactctggat ttatagcacc tccaacctgg cttctggagt ccctgctcgc    180

ttcagtggca gtggatctgg gacctcttac tctctcacaa tcagccgaat ggaggctgaa    240

gatgctgcca cttattactg ccagcaaagg agtagttacc cgaacacgtt cggagggggg    300

accaagctgg aaatcaaacg t                                              321


<210> SEQ ID NO 56
<211> LENGTH: 321
<212> TYPE: DNA
<213> ORGANISM: Artificial Sequence
<220> FEATURE:
<223> OTHER INFORMATION: VL group 1

<400> SEQUENCE: 56

gacattgtga tgacgcagtc tccagcaatc atgtctgcat ctccagggga gaaggtcacc     60
```

ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctcg agatcaaacg t 321

<210> SEQ ID NO 57
<211> LENGTH: 321
<212> TYPE: DNA
<213> ORGANISM: Artificial Sequence
<220> FEATURE:
<223> OTHER INFORMATION: VL group 1

<400> SEQUENCE: 57
gacattgtga tgacccagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg aaataaaacg t 321

<210> SEQ ID NO 58
<211> LENGTH: 321
<212> TYPE: DNA
<213> ORGANISM: Artificial Sequence
<220> FEATURE:
<223> OTHER INFORMATION: VL group 1

<400> SEQUENCE: 58
gatattgtga tgactcagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg aaataaaacg t 321

<210> SEQ ID NO 59
<211> LENGTH: 321
<212> TYPE: DNA
<213> ORGANISM: Artificial Sequence
<220> FEATURE:
<223> OTHER INFORMATION: VL group 1

<400> SEQUENCE: 59
gacattgtga tgacccagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctcg agatcaaacg t 321

<210> SEQ ID NO 60
<211> LENGTH: 321

<212> TYPE: DNA
<213> ORGANISM: Artificial Sequence
<220> FEATURE:
<223> OTHER INFORMATION: VL group 1

<400> SEQUENCE: 60
gatattgtga tgacccagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg aaataaaacg t 321

<210> SEQ ID NO 61
<211> LENGTH: 321
<212> TYPE: DNA
<213> ORGANISM: Artificial Sequence
<220> FEATURE:
<223> OTHER INFORMATION: VL group 1

<400> SEQUENCE: 61
gatattgtga tgacgcagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctcg agatcaaacg t 321

<210> SEQ ID NO 62
<211> LENGTH: 321
<212> TYPE: DNA
<213> ORGANISM: Artificial Sequence
<220> FEATURE:
<223> OTHER INFORMATION: VL group 1

<400> SEQUENCE: 62
gatattgtga tgacccagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg agatcaaacg t 321

<210> SEQ ID NO 63
<211> LENGTH: 321
<212> TYPE: DNA
<213> ORGANISM: Artificial Sequence
<220> FEATURE:
<223> OTHER INFORMATION: VL group 1

<400> SEQUENCE: 63
gacattgtga tgacgcagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg agctgaaacg t 321

<210> SEQ ID NO 64
<211> LENGTH: 321
<212> TYPE: DNA
<213> ORGANISM: Artificial Sequence
<220> FEATURE:
<223> OTHER INFORMATION: VL group 1

<400> SEQUENCE: 64
gacattgtga tgacccagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg agctgaaacg t 321

<210> SEQ ID NO 65
<211> LENGTH: 321
<212> TYPE: DNA
<213> ORGANISM: Artificial Sequence
<220> FEATURE:
<223> OTHER INFORMATION: VL group 1

<400> SEQUENCE: 65
gatattgtga tgacgcagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg agctgaaacg t 321

<210> SEQ ID NO 66
<211> LENGTH: 321
<212> TYPE: DNA
<213> ORGANISM: Artificial Sequence
<220> FEATURE:
<223> OTHER INFORMATION: VL group 1

<400> SEQUENCE: 66
gatattgtga tgacacagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg agctgaaacg t 321

<210> SEQ ID NO 67
<211> LENGTH: 321
<212> TYPE: DNA
<213> ORGANISM: Artificial Sequence
<220> FEATURE:
<223> OTHER INFORMATION: VL group 1

<400> SEQUENCE: 67
gacattcaga tgactcagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgcttgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctcg agatcaaacg t 321

<210> SEQ ID NO 68
<211> LENGTH: 321
<212> TYPE: DNA
<213> ORGANISM: Artificial Sequence
<220> FEATURE:
<223> OTHER INFORMATION: VL group 1

<400> SEQUENCE: 68
gatattaaga taaaccagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctcg agatcaaacg t 321

<210> SEQ ID NO 69
<211> LENGTH: 321
<212> TYPE: DNA
<213> ORGANISM: Artificial Sequence
<220> FEATURE:
<223> OTHER INFORMATION: VL group 1

<400> SEQUENCE: 69
gatattcaga tgacccagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctcg agatcaaacg t 321

<210> SEQ ID NO 70
<211> LENGTH: 321
<212> TYPE: DNA
<213> ORGANISM: Artificial Sequence
<220> FEATURE:
<223> OTHER INFORMATION: VL group 1

<400> SEQUENCE: 70
gacattcaga tgattcagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctcg agatcaaacg t 321

<210> SEQ ID NO 71
<211> LENGTH: 321
<212> TYPE: DNA
<213> ORGANISM: Artificial Sequence
<220> FEATURE:
<223> OTHER INFORMATION: VL group 1

<400> SEQUENCE: 71
gatattttgc tcactcagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg aaataaaacg t 321

<210> SEQ ID NO 72
<211> LENGTH: 321
<212> TYPE: DNA
<213> ORGANISM: Artificial Sequence
<220> FEATURE:
<223> OTHER INFORMATION: VL group 1

<400> SEQUENCE: 72
gatatccagc tgactcagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg aaatcaaacg t 321

<210> SEQ ID NO 73
<211> LENGTH: 321
<212> TYPE: DNA
<213> ORGANISM: Artificial Sequence
<220> FEATURE:
<223> OTHER INFORMATION: VL group 1

<400> SEQUENCE: 73
gatattttga tgacccaatc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctcg agatcaaacg t 321

<210> SEQ ID NO 74
<211> LENGTH: 321
<212> TYPE: DNA
<213> ORGANISM: Artificial Sequence
<220> FEATURE:
<223> OTHER INFORMATION: VL group 1
<220> FEATURE:
<221> NAME/KEY: misc_feature
<222> LOCATION: (12)..(12)
<223> OTHER INFORMATION: a, t, g or c

<400> SEQUENCE: 74
gatattctga tnacccagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg agctgaaacg t 321

<210> SEQ ID NO 75
<211> LENGTH: 321
<212> TYPE: DNA
<213> ORGANISM: Artificial Sequence
<220> FEATURE:
<223> OTHER INFORMATION: VL group 1

<400> SEQUENCE: 75
gatgttttga tgacccagtc tccggcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctcg agatcaaacg t 321

<210> SEQ ID NO 76
<211> LENGTH: 321
<212> TYPE: DNA
<213> ORGANISM: Artificial Sequence
<220> FEATURE:
<223> OTHER INFORMATION: VL group 1

<400> SEQUENCE: 76
gatattgtga tgacacagac tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctcg agatcaaacg t 321

<210> SEQ ID NO 77
<211> LENGTH: 321
<212> TYPE: DNA
<213> ORGANISM: Artificial Sequence
<220> FEATURE:
<223> OTHER INFORMATION: VL group 1

<400> SEQUENCE: 77
gatgttttga tgactcagtc tccagcaatc atgtctgcat ctccagggga gaaggtcacc 60
ataacctgca gtgccagctc aagtgtaagt tacatgaact ggttccagca gaagccaggc 120
acttctccca aactctggat ttatagcacc tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtagttacc cgaacacgtt cggagggggg 300
accaagctgg agctgaaacg t 321

<210> SEQ ID NO 78
<211> LENGTH: 360
<212> TYPE: DNA
<213> ORGANISM: Artificial Sequence
<220> FEATURE:
<223> OTHER INFORMATION: VH group 1

<400> SEQUENCE: 78
gaggtgaagc tgcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 79
<211> LENGTH: 360
<212> TYPE: DNA
<213> ORGANISM: Artificial Sequence
<220> FEATURE:
<223> OTHER INFORMATION: VH group 1

<400> SEQUENCE: 79
gaggtcaaac tgcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 80
<211> LENGTH: 360
<212> TYPE: DNA
<213> ORGANISM: Artificial Sequence
<220> FEATURE:
<223> OTHER INFORMATION: VH group 1

<400> SEQUENCE: 80
gaggtgaagc tgcaggagtc aggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 81
<211> LENGTH: 360
<212> TYPE: DNA
<213> ORGANISM: Artificial Sequence
<220> FEATURE:
<223> OTHER INFORMATION: VH group 1
<220> FEATURE:
<221> NAME/KEY: misc_feature
<222> LOCATION: (6)..(6)
<223> OTHER INFORMATION: a, t, g or c

<400> SEQUENCE: 81
gaggtnaagc ttcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 82
<211> LENGTH: 360
<212> TYPE: DNA
<213> ORGANISM: Artificial Sequence
<220> FEATURE:
<223> OTHER INFORMATION: VH group 1

<400> SEQUENCE: 82
gaggtgaagc ttcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 83
<211> LENGTH: 360
<212> TYPE: DNA
<213> ORGANISM: Artificial Sequence
<220> FEATURE:
<223> OTHER INFORMATION: VH group 1

<400> SEQUENCE: 83
gaggtgaagc tggtggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 84
<211> LENGTH: 360
<212> TYPE: DNA
<213> ORGANISM: Artificial Sequence
<220> FEATURE:
<223> OTHER INFORMATION: VH group 1

<400> SEQUENCE: 84
gaagtgaagc tggtggagtc aggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 85
<211> LENGTH: 360
<212> TYPE: DNA
<213> ORGANISM: Artificial Sequence
<220> FEATURE:
<223> OTHER INFORMATION: VH group 1

<400> SEQUENCE: 85
gaagtgaagt tggtggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 86
<211> LENGTH: 360
<212> TYPE: DNA
<213> ORGANISM: Artificial Sequence
<220> FEATURE:
<223> OTHER INFORMATION: VH group 1

<400> SEQUENCE: 86
gaggtgaagt tggtggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 87
<211> LENGTH: 360
<212> TYPE: DNA
<213> ORGANISM: Artificial Sequence
<220> FEATURE:
<223> OTHER INFORMATION: VH group 1

<400> SEQUENCE: 87
gaggtgcaac tgcagcagtc aggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 88
<211> LENGTH: 360
<212> TYPE: DNA
<213> ORGANISM: Artificial Sequence
<220> FEATURE:
<223> OTHER INFORMATION: VH group 1

<400> SEQUENCE: 88
gaggtccagc tgcagcagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 89
<211> LENGTH: 360
<212> TYPE: DNA
<213> ORGANISM: Artificial Sequence
<220> FEATURE:
<223> OTHER INFORMATION: VH group 1

<400> SEQUENCE: 89
gaggtccagc tgcaacagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 90
<211> LENGTH: 360
<212> TYPE: DNA
<213> ORGANISM: Artificial Sequence
<220> FEATURE:
<223> OTHER INFORMATION: VH group 1

<400> SEQUENCE: 90
gaggtgcagc tgcagcagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 91
<211> LENGTH: 360
<212> TYPE: DNA
<213> ORGANISM: Artificial Sequence
<220> FEATURE:
<223> OTHER INFORMATION: VH group 1

<400> SEQUENCE: 91
gaggtccagc tccagcagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 92

<211> LENGTH: 360
<212> TYPE: DNA
<213> ORGANISM: Artificial Sequence
<220> FEATURE:
<223> OTHER INFORMATION: VH group 1

<400> SEQUENCE: 92
gaggtgcagg gggtggagtc aggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 93
<211> LENGTH: 360
<212> TYPE: DNA
<213> ORGANISM: Artificial Sequence
<220> FEATURE:
<223> OTHER INFORMATION: VH group 1

<400> SEQUENCE: 93
gaggtgcagg gggtggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 94
<211> LENGTH: 360
<212> TYPE: DNA
<213> ORGANISM: Artificial Sequence
<220> FEATURE:
<223> OTHER INFORMATION: VH group 1

<400> SEQUENCE: 94
caggtccagc tgcagcagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 95
<211> LENGTH: 360
<212> TYPE: DNA
<213> ORGANISM: Artificial Sequence
<220> FEATURE:
<223> OTHER INFORMATION: VH group 1

<400> SEQUENCE: 95
caggtccagc ttcagcagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 96
<211> LENGTH: 360
<212> TYPE: DNA
<213> ORGANISM: Artificial Sequence
<220> FEATURE:
<223> OTHER INFORMATION: VH group 1

<400> SEQUENCE: 96
caggtccaac tgcagcagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 97
<211> LENGTH: 360
<212> TYPE: DNA
<213> ORGANISM: Artificial Sequence
<220> FEATURE:
<223> OTHER INFORMATION: VH group 1

<400> SEQUENCE: 97
caggttcagc tgcagcagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 98
<211> LENGTH: 360
<212> TYPE: DNA
<213> ORGANISM: Artificial Sequence
<220> FEATURE:
<223> OTHER INFORMATION: VH group 1

<400> SEQUENCE: 98
caggttcagc ttcagcaatc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 99
<211> LENGTH: 360
<212> TYPE: DNA
<213> ORGANISM: Artificial Sequence
<220> FEATURE:

<223> OTHER INFORMATION: VH group 1

<400> SEQUENCE: 99
gaggtgcagc ttcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 100
<211> LENGTH: 360
<212> TYPE: DNA
<213> ORGANISM: Artificial Sequence
<220> FEATURE:
<223> OTHER INFORMATION: VH group 1

<400> SEQUENCE: 100
gaggtacagc ttcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 101
<211> LENGTH: 360
<212> TYPE: DNA
<213> ORGANISM: Artificial Sequence
<220> FEATURE:
<223> OTHER INFORMATION: VH group 1

<400> SEQUENCE: 101
gaggtgcagc tgcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 102
<211> LENGTH: 360
<212> TYPE: DNA
<213> ORGANISM: Artificial Sequence
<220> FEATURE:
<223> OTHER INFORMATION: VH group 1

<400> SEQUENCE: 102
caggtgcagc tgcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 103
<211> LENGTH: 360
<212> TYPE: DNA
<213> ORGANISM: Artificial Sequence
<220> FEATURE:
<223> OTHER INFORMATION: VH group 1

<400> SEQUENCE: 103
caggttcaac tgcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 104
<211> LENGTH: 360
<212> TYPE: DNA
<213> ORGANISM: Artificial Sequence
<220> FEATURE:
<223> OTHER INFORMATION: VH group 1

<400> SEQUENCE: 104
caggtccaac tgcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 105
<211> LENGTH: 360
<212> TYPE: DNA
<213> ORGANISM: Artificial Sequence
<220> FEATURE:
<223> OTHER INFORMATION: VH group 1

<400> SEQUENCE: 105
gaggtccagc tgcaacagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccactctcac agtctcctca 360

<210> SEQ ID NO 106
<211> LENGTH: 360
<212> TYPE: DNA
<213> ORGANISM: Artificial Sequence
<220> FEATURE:
<223> OTHER INFORMATION: VH group 1

<400> SEQUENCE: 106

-continued

```
caggtcaagc tgcaggagtc aggagctgaa ctggtaaagc ctggggcttc agtgaagttg     60

tcctgcaagg cttctggcta caccttcaga agttatgata taaactgggt gagacagagg    120

cctgaacagg gacttgagtg gattggatgg atttttcctg gagatggtag tactaagtac    180

aatgagaagt tcaagggcaa ggccacactg actacagaca aatcctccag cacagcctac    240

atgcagctca gcaggctgac atctgaggac tctgctgtct atttctgtgc aagatggacg    300

gtagtaggcc cagggtactt cgatgtctgg ggcgcaggga ccacggtcac cgtctcctca    360
```

```
<210> SEQ ID NO 107
<211> LENGTH: 360
<212> TYPE: DNA
<213> ORGANISM: Artificial Sequence
<220> FEATURE:
<223> OTHER INFORMATION: VH group 1

<400> SEQUENCE: 107

caggtgaagc tgcaggagtc tggagctgaa ctggtaaagc ctggggcttc agtgaagttg     60

tcctgcaagg cttctggcta caccttcaga agttatgata taaactgggt gagacagagg    120

cctgaacagg gacttgagtg gattggatgg atttttcctg gagatggtag tactaagtac    180

aatgagaagt tcaagggcaa ggccacactg actacagaca aatcctccag cacagcctac    240

atgcagctca gcaggctgac atctgaggac tctgctgtct atttctgtgc aagatggacg    300

gtagtaggcc cagggtactt cgatgtctgg ggcgcaggga ccacggtcac cgtctcctca    360
```

```
<210> SEQ ID NO 108
<211> LENGTH: 360
<212> TYPE: DNA
<213> ORGANISM: Artificial Sequence
<220> FEATURE:
<223> OTHER INFORMATION: VH group 1

<400> SEQUENCE: 108

gaggtgaagc tgcagcagtc tggagctgaa ctggtaaagc ctggggcttc agtgaagttg     60

tcctgcaagg cttctggcta caccttcaga agttatgata taaactgggt gagacagagg    120

cctgaacagg gacttgagtg gattggatgg atttttcctg gagatggtag tactaagtac    180

aatgagaagt tcaagggcaa ggccacactg actacagaca aatcctccag cacagcctac    240

atgcagctca gcaggctgac atctgaggac tctgctgtct atttctgtgc aagatggacg    300

gtagtaggcc cagggtactt cgatgtctgg ggcgcaggga ccacggtcac cgtctcctca    360
```

```
<210> SEQ ID NO 109
<211> LENGTH: 360
<212> TYPE: DNA
<213> ORGANISM: Artificial Sequence
<220> FEATURE:
<223> OTHER INFORMATION: VH group 1

<400> SEQUENCE: 109

gaggtcaaac tgcagcagtc tggagctgaa ctggtaaagc ctggggcttc agtgaagttg     60

tcctgcaagg cttctggcta caccttcaga agttatgata taaactgggt gagacagagg    120

cctgaacagg gacttgagtg gattggatgg atttttcctg gagatggtag tactaagtac    180

aatgagaagt tcaagggcaa ggccacactg actacagaca aatcctccag cacagcctac    240

atgcagctca gcaggctgac atctgaggac tctgctgtct atttctgtgc aagatggacg    300

gtagtaggcc cagggtactt cgatgtctgg ggcgcaggga ccacggtcac cgtctcctca    360
```

-continued

<210> SEQ ID NO 110
<211> LENGTH: 360
<212> TYPE: DNA
<213> ORGANISM: Artificial Sequence
<220> FEATURE:
<223> OTHER INFORMATION: VH group 1

<400> SEQUENCE: 110
gaggtgaagg tggtggagtc aggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 111
<211> LENGTH: 360
<212> TYPE: DNA
<213> ORGANISM: Artificial Sequence
<220> FEATURE:
<223> OTHER INFORMATION: VH group 1

<400> SEQUENCE: 111
gaggtgaagg tggtggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 112
<211> LENGTH: 360
<212> TYPE: DNA
<213> ORGANISM: Artificial Sequence
<220> FEATURE:
<223> OTHER INFORMATION: VH group 1

<400> SEQUENCE: 112
gatgtgcagc ttcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 113
<211> LENGTH: 360
<212> TYPE: DNA
<213> ORGANISM: Artificial Sequence
<220> FEATURE:
<223> OTHER INFORMATION: VH group 1

<400> SEQUENCE: 113
gaggtgcagc tgcagcagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccccagtcac cgtctcctca 360

<210> SEQ ID NO 114
<211> LENGTH: 360
<212> TYPE: DNA
<213> ORGANISM: Artificial Sequence
<220> FEATURE:
<223> OTHER INFORMATION: VH group 1

<400> SEQUENCE: 114
caggtgcagc tgaaggagtc aggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 115
<211> LENGTH: 360
<212> TYPE: DNA
<213> ORGANISM: Artificial Sequence
<220> FEATURE:
<223> OTHER INFORMATION: VH group 1

<400> SEQUENCE: 115
gaggtgatgc tggtggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 116
<211> LENGTH: 360
<212> TYPE: DNA
<213> ORGANISM: Artificial Sequence
<220> FEATURE:
<223> OTHER INFORMATION: VH group 1
<220> FEATURE:
<221> NAME/KEY: misc_feature
<222> LOCATION: (7)..(7)
<223> OTHER INFORMATION: a, g or c

<400> SEQUENCE: 116
gaagtgnagc tggtggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 117
<211> LENGTH: 360
<212> TYPE: DNA
<213> ORGANISM: Artificial Sequence
<220> FEATURE:
<223> OTHER INFORMATION: VH group 1

<400> SEQUENCE: 117
gatgtaaagc ttcaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 118
<211> LENGTH: 360
<212> TYPE: DNA
<213> ORGANISM: Artificial Sequence
<220> FEATURE:
<223> OTHER INFORMATION: VH group 1

<400> SEQUENCE: 118
gaggtgcaac tggtggagtc aggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 119
<211> LENGTH: 360
<212> TYPE: DNA
<213> ORGANISM: Artificial Sequence
<220> FEATURE:
<223> OTHER INFORMATION: VH group 1

<400> SEQUENCE: 119
gaggtgcagc tggtggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga cctcagtcac cgtctcctca 360

<210> SEQ ID NO 120
<211> LENGTH: 360
<212> TYPE: DNA
<213> ORGANISM: Artificial Sequence
<220> FEATURE:
<223> OTHER INFORMATION: VH group 1
<220> FEATURE:
<221> NAME/KEY: misc_feature
<222> LOCATION: (6)..(6)
<223> OTHER INFORMATION: a, t, g or c
<220> FEATURE:
<221> NAME/KEY: misc_feature
<222> LOCATION: (15)..(15)

<223> OTHER INFORMATION: a, t, g or c

<400> SEQUENCE: 120
gaggtncagc tgcancagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 121
<211> LENGTH: 360
<212> TYPE: DNA
<213> ORGANISM: Artificial Sequence
<220> FEATURE:
<223> OTHER INFORMATION: VH group 1

<400> SEQUENCE: 121
gaggtgaagc tgatggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 122
<211> LENGTH: 360
<212> TYPE: DNA
<213> ORGANISM: Artificial Sequence
<220> FEATURE:
<223> OTHER INFORMATION: VH group 1
<220> FEATURE:
<221> NAME/KEY: misc_feature
<222> LOCATION: (1)..(1)
<223> OTHER INFORMATION: a, g or c
<220> FEATURE:
<221> NAME/KEY: misc_feature
<222> LOCATION: (6)..(6)
<223> OTHER INFORMATION: a, t, g or c
<220> FEATURE:
<221> NAME/KEY: misc_feature
<222> LOCATION: (16)..(16)
<223> OTHER INFORMATION: a, g or c

<400> SEQUENCE: 122
naggtncaac tgcagnagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 123
<211> LENGTH: 360
<212> TYPE: DNA
<213> ORGANISM: Artificial Sequence
<220> FEATURE:
<223> OTHER INFORMATION: VH group 1

<400> SEQUENCE: 123
gaggtgaagg tggtggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga cctcagtcac cgtctcctca 360

<210> SEQ ID NO 124
<211> LENGTH: 360
<212> TYPE: DNA
<213> ORGANISM: Artificial Sequence
<220> FEATURE:
<223> OTHER INFORMATION: VH group 1

<400> SEQUENCE: 124
gaggtgcagc tgaaggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcaggga ccacggtcac cgtctcctca 360

<210> SEQ ID NO 125
<211> LENGTH: 360
<212> TYPE: DNA
<213> ORGANISM: Artificial Sequence
<220> FEATURE:
<223> OTHER INFORMATION: VH group 1
<220> FEATURE:
<221> NAME/KEY: misc_feature
<222> LOCATION: (337)..(337)
<223> OTHER INFORMATION: a, t or c

<400> SEQUENCE: 125
gaggtgcaac tgcagcagtc aggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180
aatgagaagt tcaagggcaa ggccacactg actacagaca aatcctccag cacagcctac 240
atgcagctca gcaggctgac atctgaggac tctgctgtct atttctgtgc aagatggacg 300
gtagtaggcc cagggtactt cgatgtctgg ggcgcangga ccacggtcac cgtctcctca 360

<210> SEQ ID NO 126
<211> LENGTH: 360
<212> TYPE: DNA
<213> ORGANISM: Artificial Sequence
<220> FEATURE:
<223> OTHER INFORMATION: VH group 1

<400> SEQUENCE: 126
gaggtgcagc gggtggagtc tggagctgaa ctggtaaagc ctggggcttc agtgaagttg 60
tcctgcaagg cttctggcta caccttcaga agttatgata taaactgggt gagacagagg 120
cctgaacagg gacttgagtg gattggatgg atttttcctg gagatggtag tactaagtac 180

```
aatgagaagt tcaagggcaa ggccacactg actacagaca aatcctccag cacagcctac    240

atgcagctca gcaggctgac atctgaggac tctgctgtct atttctgtgc aagatggacg    300

gtagtaggcc cagggtactt cgatgtctgg ggcgcaggga ccacggtcac cgtctcctca    360


<210> SEQ ID NO 127
<211> LENGTH: 321
<212> TYPE: DNA
<213> ORGANISM: Artificial Sequence
<220> FEATURE:
<223> OTHER INFORMATION: CL

<400> SEQUENCE: 127

cgggctgatg ctgcaccaac tgtatccatc ttcccaccat ccagtgagca gttaacatct     60

ggaggtgcct cagtcgtgtg cttcttgaac aacttctacc ccaaagacat caatgtcaag    120

tggaagattg atggcagtga acgacaaaat ggcgtcctga acagttggac tgatcaggac    180

agcaaagaca gcacctacag catgagcagc accctcacgt tgaccaagga cgagtatgaa    240

cgacataaca gttatacctg tgaggccact cacaagacat caacttcacc cattgtcaag    300

agcttcaaca ggaatgagtg t                                              321


<210> SEQ ID NO 128
<211> LENGTH: 1008
<212> TYPE: DNA
<213> ORGANISM: Artificial Sequence
<220> FEATURE:
<223> OTHER INFORMATION: CH1-CH2-CH3

<400> SEQUENCE: 128

gccaaaacaa cacccccatc agtctatcca ctggcccctg ggtgtggaga tacaactggt     60

tcctccgtga ctctgggatg cctggtcaag ggctacttcc ctgagtcagt gactgtgact    120

tggaactctg gatccctgtc cagcagtgtg cacaccttcc cagctctcct gcagtctgga    180

ctctacacta tgagcagctc agtgactgtc ccctccagca cctggccaag tcagaccgtc    240

acctgcagcg ttgctcaccc agccagcagc accacggtgg acaaaaaact tgagcccagc    300

gggcccattt caacaatcaa cccctgtcct ccatgcaagg agtgtcacaa atgcccagct    360

cctaacctcg agggtggacc atccgtcttc atcttccctc caaatatcaa ggatgtactc    420

atgatctccc tgacacccaa ggtcacgtgt gtggtggtgg atgtgagcga ggatgaccca    480

gacgtccaga tcagctggtt tgtgaacaac gtggaagtac acacagctca gacacaaacc    540

catagagagg attacaacag tactatccgg gtggtcagca ccctccccat ccagcaccag    600

gactggatga gtggcaagga gttcaaatgc aaggtcaaca acaaagacct cccatcaccc    660

atcgagagaa ccatctcaaa aattaaaggg ctagtcagag ctccacaagt atacatcttg    720

ccgccaccag cagagcagtt gtccaggaaa gatgtcagtc tcacttgcct ggtcgtgggc    780

ttcaaccctg gagacatcag tgtggagtgg accagcaatg ggcatacaga ggagaactac    840

aaggacaccg caccagtcct ggactctgac ggttcttact tcatatatag caagctcaat    900

atgaaaacaa gcaagtggga gaaaacagat tccttctcat gcaacgtgag acacgagggt    960

ctgaaaaatt actacctgaa gaagaccatc tcccggtctc cgggtaaa                1008


<210> SEQ ID NO 129
<211> LENGTH: 10
<212> TYPE: PRT
<213> ORGANISM: Artificial Sequence
<220> FEATURE:
<223> OTHER INFORMATION: CDR-L1 Light Group1
```

<400> SEQUENCE: 129

Ser Ala Ser Ser Ser Val Ser Tyr Met Asn
1               5                   10

<210> SEQ ID NO 130
<211> LENGTH: 7
<212> TYPE: PRT
<213> ORGANISM: Artificial Sequence
<220> FEATURE:
<223> OTHER INFORMATION: CDR-L2 Light Group1

<400> SEQUENCE: 130

Ser Thr Ser Asn Leu Ala Ser
1               5

<210> SEQ ID NO 131
<211> LENGTH: 11
<212> TYPE: PRT
<213> ORGANISM: Artificial Sequence
<220> FEATURE:
<223> OTHER INFORMATION: CDR-L1 Light Group3

<400> SEQUENCE: 131

Lys Ala Ser Glu Asn Val Val Thr Tyr Val Ser
1               5                   10

<210> SEQ ID NO 132
<211> LENGTH: 7
<212> TYPE: PRT
<213> ORGANISM: Artificial Sequence
<220> FEATURE:
<223> OTHER INFORMATION: CDR-L2 Light Group3

<400> SEQUENCE: 132

Gly Ala Ser Asn Arg Tyr Thr
1               5

<210> SEQ ID NO 133
<211> LENGTH: 10
<212> TYPE: PRT
<213> ORGANISM: Artificial Sequence
<220> FEATURE:
<223> OTHER INFORMATION: CDR-H1 Heavy

<400> SEQUENCE: 133

Gly Tyr Thr Phe Arg Ser Tyr Asp Ile Asn
1               5                   10

<210> SEQ ID NO 134
<211> LENGTH: 17
<212> TYPE: PRT
<213> ORGANISM: Artificial Sequence
<220> FEATURE:
<223> OTHER INFORMATION: CDR-H2 Heavy

<400> SEQUENCE: 134

Trp Ile Phe Pro Gly Asp Gly Ser Thr Lys Tyr Asn Glu Lys Phe Lys
1               5                   10                  15

Gly

<210> SEQ ID NO 135
<211> LENGTH: 7
<212> TYPE: PRT
<213> ORGANISM: Artificial Sequence
<220> FEATURE:

<223> OTHER INFORMATION: ABR1 Light group 1

<400> SEQUENCE: 135

Ser Ser Val Ser Tyr Met Asn
1 5

<210> SEQ ID NO 136
<211> LENGTH: 11
<212> TYPE: PRT
<213> ORGANISM: Artificial Sequence
<220> FEATURE:
<223> OTHER INFORMATION: ABR2 Light group 1

<400> SEQUENCE: 136

Leu Trp Ile Tyr Ser Thr Ser Asn Leu Ala Ser
1 5 10

<210> SEQ ID NO 137
<211> LENGTH: 8
<212> TYPE: PRT
<213> ORGANISM: Artificial Sequence
<220> FEATURE:
<223> OTHER INFORMATION: ABR3 Light group 1

<400> SEQUENCE: 137

Gln Gln Arg Ser Ser Tyr Pro Asn
1 5

<210> SEQ ID NO 138
<211> LENGTH: 8
<212> TYPE: PRT
<213> ORGANISM: Artificial Sequence
<220> FEATURE:
<223> OTHER INFORMATION: ABR1* Light group 3

<400> SEQUENCE: 138

Glu Asn Val Val Thr Tyr Val Ser
1 5

<210> SEQ ID NO 139
<211> LENGTH: 11
<212> TYPE: PRT
<213> ORGANISM: Artificial Sequence
<220> FEATURE:
<223> OTHER INFORMATION: ABR2* Light group 3

<400> SEQUENCE: 139

Leu Leu Ile Tyr Gly Ala Ser Asn Arg Tyr Thr
1 5 10

<210> SEQ ID NO 140
<211> LENGTH: 8
<212> TYPE: PRT
<213> ORGANISM: Artificial Sequence
<220> FEATURE:
<223> OTHER INFORMATION: ABR3* Light group 3

<400> SEQUENCE: 140

Gly Gln Gly Tyr Ser Tyr Pro Tyr
1 5

<210> SEQ ID NO 141
<211> LENGTH: 9
<212> TYPE: PRT
<213> ORGANISM: Artificial Sequence
<220> FEATURE:
<223> OTHER INFORMATION: ABR1h Heavy group 1

<400> SEQUENCE: 141

Tyr Thr Phe Arg Ser Tyr Asp Ile Asn
1 5

<210> SEQ ID NO 142
<211> LENGTH: 14
<212> TYPE: PRT
<213> ORGANISM: Artificial Sequence
<220> FEATURE:
<223> OTHER INFORMATION: ABR2h Heavy group 2

<400> SEQUENCE: 142

Trp Ile Gly Trp Ile Phe Pro Gly Asp Gly Ser Thr Lys Tyr
1 5 10

<210> SEQ ID NO 143
<211> LENGTH: 12
<212> TYPE: PRT
<213> ORGANISM: Artificial Sequence
<220> FEATURE:
<223> OTHER INFORMATION: ABR3h Heavy group 3

<400> SEQUENCE: 143

Arg Trp Thr Val Val Gly Pro Gly Tyr Phe Asp Val
1 5 10

<210> SEQ ID NO 144
<211> LENGTH: 766
<212> TYPE: PRT
<213> ORGANISM: Homo sapiens
<220> FEATURE:
<221> NAME/KEY: misc_feature
<223> OTHER INFORMATION: >gi|197692677|dbj|BAG70302.1|
dipeptidylpeptidase IV

<400> SEQUENCE: 144

Met Lys Thr Pro Trp Lys Val Leu Leu Gly Leu Leu Gly Ala Ala Ala
1 5 10 15

Leu Val Thr Ile Ile Thr Val Pro Val Val Leu Leu Asn Lys Gly Thr
20 25 30

Asp Asp Ala Thr Ala Asp Ser Arg Lys Thr Tyr Thr Leu Thr Asp Tyr
35 40 45

Leu Lys Asn Thr Tyr Arg Leu Lys Leu Tyr Ser Leu Arg Trp Ile Ser
50 55 60

Asp His Glu Tyr Leu Tyr Lys Gln Glu Asn Asn Ile Leu Val Phe Asn
65 70 75 80

Ala Glu Tyr Gly Asn Ser Ser Val Phe Leu Glu Asn Ser Thr Phe Asp
85 90 95

Glu Phe Gly His Ser Ile Asn Asp Tyr Ser Ile Ser Pro Asp Gly Gln
100 105 110

Phe Ile Leu Leu Glu Tyr Asn Tyr Val Lys Gln Trp Arg His Ser Tyr
115 120 125

Thr Ala Ser Tyr Asp Ile Tyr Asp Leu Asn Lys Arg Gln Leu Ile Thr
130 135 140

Glu Glu Arg Ile Pro Asn Asn Thr Gln Trp Val Thr Trp Ser Pro Val
145 150 155 160

Gly His Lys Leu Ala Tyr Val Trp Asn Asn Asp Ile Tyr Val Lys Ile
165 170 175

Glu Pro Asn Leu Pro Ser Tyr Arg Ile Thr Trp Thr Gly Lys Glu Asp
180 185 190

```
Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
    450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
    530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
        595                 600                 605
```

-continued

```
Ala Ala Arg Gln Phe Ser Lys Met Gly Phe Val Asp Asn Lys Arg Ile
    610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
        675                 680                 685

Met Ser Arg Ala Glu Asn Phe Lys Gln Val Glu Tyr Leu Leu Ile His
    690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765


<210> SEQ ID NO 145
<211> LENGTH: 766
<212> TYPE: PRT
<213> ORGANISM: Sus scrofa
<220> FEATURE:
<221> NAME/KEY: misc_feature
<223> OTHER INFORMATION: >gi|47523582|ref|NP_999422.1| dipeptidyl
      peptidase 4

<400> SEQUENCE: 145

Met Lys Thr Pro Trp Lys Val Leu Leu Gly Leu Leu Gly Ile Ala Ala
1               5                   10                  15

Leu Val Thr Val Ile Thr Val Pro Val Val Leu Leu Asn Lys Gly Thr
            20                  25                  30

Asp Asp Ala Ala Ala Asp Ser Arg Arg Thr Tyr Thr Leu Thr Asp Tyr
        35                  40                  45

Leu Lys Ser Thr Phe Arg Val Lys Phe Tyr Thr Leu Gln Trp Ile Ser
    50                  55                  60

Asp His Glu Tyr Leu Tyr Lys Gln Glu Asn Asn Ile Leu Leu Phe Asn
65                  70                  75                  80

Ala Glu Tyr Gly Asn Ser Ser Ile Phe Leu Glu Asn Ser Thr Phe Asp
                85                  90                  95

Glu Leu Gly Tyr Ser Thr Asn Asp Tyr Ser Val Ser Pro Asp Arg Gln
            100                 105                 110

Phe Ile Leu Phe Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Ile Thr Trp Ser Pro Val
145                 150                 155                 160

Gly His Lys Leu Ala Tyr Val Trp Asn Asn Asp Ile Tyr Val Lys Asn
                165                 170                 175

Glu Pro Asn Leu Ser Ser Gln Arg Ile Thr Trp Thr Gly Lys Glu Asn
            180                 185                 190

Val Ile Tyr Asn Gly Val Thr Asp Trp Val Tyr Glu Glu Glu Val Phe
```

```
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Ile Pro Tyr
                245                 250                 255

Pro Lys Ala Gly Ala Glu Asn Pro Thr Val Lys Phe Phe Val Val Asp
            260                 265                 270

Thr Arg Thr Leu Ser Pro Asn Ala Ser Val Thr Ser Tyr Gln Ile Val
        275                 280                 285

Pro Pro Ala Ser Val Leu Ile Gly Asp His Tyr Leu Cys Gly Val Thr
    290                 295                 300

Trp Val Thr Glu Glu Arg Ile Ser Leu Gln Trp Ile Arg Arg Ala Gln
305                 310                 315                 320

Asn Tyr Ser Ile Ile Asp Ile Cys Asp Tyr Asp Glu Ser Thr Gly Arg
                325                 330                 335

Trp Ile Ser Ser Val Ala Arg Gln His Ile Glu Ile Ser Thr Thr Gly
            340                 345                 350

Trp Val Gly Arg Phe Arg Pro Ala Glu Pro His Phe Thr Ser Asp Gly
        355                 360                 365

Asn Ser Phe Tyr Lys Ile Ile Ser Asn Glu Glu Gly Tyr Lys His Ile
    370                 375                 380

Cys His Phe Gln Thr Asp Lys Ser Asn Cys Thr Phe Ile Thr Lys Gly
385                 390                 395                 400

Ala Trp Glu Val Ile Gly Ile Glu Ala Leu Thr Ser Asp Tyr Leu Tyr
                405                 410                 415

Tyr Ile Ser Asn Glu His Lys Gly Met Pro Gly Gly Arg Asn Leu Tyr
            420                 425                 430

Arg Ile Gln Leu Asn Asp Tyr Thr Lys Val Thr Cys Leu Ser Cys Glu
        435                 440                 445

Leu Asn Pro Glu Arg Cys Gln Tyr Tyr Ser Ala Ser Phe Ser Asn Lys
    450                 455                 460

Ala Lys Tyr Tyr Gln Leu Arg Cys Phe Gly Pro Gly Leu Pro Leu Tyr
465                 470                 475                 480

Thr Leu His Ser Ser Ser Ser Asp Lys Glu Leu Arg Val Leu Glu Asp
                485                 490                 495

Asn Ser Ala Leu Asp Lys Met Leu Gln Asp Val Gln Met Pro Ser Lys
            500                 505                 510

Lys Leu Asp Val Ile Asn Leu His Gly Thr Lys Phe Trp Tyr Gln Met
        515                 520                 525

Ile Leu Pro Pro His Phe Asp Lys Ser Lys Lys Tyr Pro Leu Leu Ile
    530                 535                 540

Glu Val Tyr Ala Gly Pro Cys Ser Gln Lys Val Asp Thr Val Phe Arg
545                 550                 555                 560

Leu Ser Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
        595                 600                 605

Ala Thr Arg Gln Phe Ser Lys Met Gly Phe Val Asp Asp Lys Arg Ile
    610                 615                 620
```

Ala Ile Trp Gly Trp Ser Tyr Gly Gly Tyr Val Thr Ser Met Val Leu
625 630 635 640

Gly Ala Gly Ser Gly Val Phe Lys Cys Gly Ile Ala Val Ala Pro Val
645 650 655

Ser Lys Trp Glu Tyr Tyr Asp Ser Val Tyr Thr Glu Arg Tyr Met Gly
660 665 670

Leu Pro Thr Pro Glu Asp Asn Leu Asp Tyr Tyr Arg Asn Ser Thr Val
675 680 685

Met Ser Arg Ala Glu Asn Phe Lys Gln Val Glu Tyr Leu Leu Ile His
690 695 700

Gly Thr Ala Asp Asp Asn Val His Phe Gln Gln Ser Ala Gln Leu Ser
705 710 715 720

Lys Ala Leu Val Asp Ala Gly Val Asp Phe Gln Thr Met Trp Tyr Thr
725 730 735

Asp Glu Asp His Gly Ile Ala Ser Asn Met Ala His Gln His Ile Tyr
740 745 750

Thr His Met Ser His Phe Leu Lys Gln Cys Phe Ser Leu Pro
755 760 765

<210> SEQ ID NO 146
<211> LENGTH: 15
<212> TYPE: PRT
<213> ORGANISM: Homo sapiens
<220> FEATURE:
<221> NAME/KEY: misc_feature
<223> OTHER INFORMATION: >CD26 EPITOPE 1

<400> SEQUENCE: 146

Asp Tyr Asp Glu Ser Ser Gly Arg Trp Asn Cys Leu Val Ala Arg
1 5 10 15

<210> SEQ ID NO 147
<211> LENGTH: 15
<212> TYPE: PRT
<213> ORGANISM: Homo sapiens
<220> FEATURE:
<221> NAME/KEY: misc_feature
<223> OTHER INFORMATION: >CD26 EPITOPE 2

<400> SEQUENCE: 147

Asp Val Thr Trp Ala Thr Gln Glu Arg Ile Ser Leu Gln Trp Leu
1 5 10 15

<210> SEQ ID NO 148
<211> LENGTH: 13
<212> TYPE: PRT
<213> ORGANISM: Homo sapiens
<220> FEATURE:
<221> NAME/KEY: MISC_FEATURE
<223> OTHER INFORMATION: >CD26 EPITOPE 3

<400> SEQUENCE: 148

Trp Trp Ser Pro Asn Gly Thr Phe Leu Ala Tyr Ala Gln
1 5 10

<210> SEQ ID NO 149
<211> LENGTH: 15
<212> TYPE: PRT
<213> ORGANISM: Homo sapiens
<220> FEATURE:
<221> NAME/KEY: MISC_FEATURE
<223> OTHER INFORMATION: >CD26 EPITOPE 4

<400> SEQUENCE: 149

Gln Leu Arg Cys Ser Gly Pro Gly Leu Pro Leu Tyr Thr Leu His
1 5 10 15

<210> SEQ ID NO 150
<211> LENGTH: 13
<212> TYPE: PRT
<213> ORGANISM: Homo sapiens
<220> FEATURE:
<221> NAME/KEY: MISC_FEATURE
<223> OTHER INFORMATION: >CD26 EPITOPE 5

<400> SEQUENCE: 150

Leu Asn Glu Thr Lys Phe Trp Tyr Gln Met Ile Leu Pro
1 5 10

<210> SEQ ID NO 151
<211> LENGTH: 16
<212> TYPE: PRT
<213> ORGANISM: Homo sapiens
<220> FEATURE:
<221> NAME/KEY: MISC_FEATURE
<223> OTHER INFORMATION: >CD26 EPITOPE 6

<400> SEQUENCE: 151

Met Gly Phe Val Asp Asn Lys Arg Ile Ala Ile Trp Gly Trp Ser Tyr
1 5 10 15

<210> SEQ ID NO 152
<211> LENGTH: 5
<212> TYPE: PRT
<213> ORGANISM: Homo sapiens
<220> FEATURE:
<221> NAME/KEY: MISC_FEATURE
<223> OTHER INFORMATION: >CD26 EPITOPE 7

<400> SEQUENCE: 152

Pro Asn Gly Thr Phe
1 5

<210> SEQ ID NO 153
<211> LENGTH: 15
<212> TYPE: PRT
<213> ORGANISM: Homo sapiens
<220> FEATURE:
<221> NAME/KEY: MISC_FEATURE
<223> OTHER INFORMATION: > CD26 EPITOPE 8

<400> SEQUENCE: 153

Thr Thr Gly Trp Val Gly Arg Phe Arg Pro Ser Glu Pro His Phe
1 5 10 15

<210> SEQ ID NO 154
<211> LENGTH: 9
<212> TYPE: PRT
<213> ORGANISM: Homo sapiens
<220> FEATURE:
<221> NAME/KEY: MISC_FEATURE
<223> OTHER INFORMATION: >CD26 EPITOPE 9

<400> SEQUENCE: 154

Arg Phe Arg Pro Ser Glu Pro His Phe
1 5

<210> SEQ ID NO 155
<211> LENGTH: 12
<212> TYPE: PRT

-continued

```
<213> ORGANISM: Homo sapiens
<220> FEATURE:
<221> NAME/KEY: MISC_FEATURE
<223> OTHER INFORMATION: >CD26 EPITOPE 10

<400> SEQUENCE: 155

Thr Phe Ile Thr Lys Gly Thr Trp Glu Val Ile Gly
1               5                   10


<210> SEQ ID NO 156
<211> LENGTH: 9
<212> TYPE: PRT
<213> ORGANISM: Homo sapiens
<220> FEATURE:
<221> NAME/KEY: MISC_FEATURE
<223> OTHER INFORMATION: >CD26 EPITOPE 11

<400> SEQUENCE: 156

Asp Tyr Leu Tyr Tyr Ile Ser Asn Glu
1               5


<210> SEQ ID NO 157
<211> LENGTH: 12
<212> TYPE: PRT
<213> ORGANISM: Homo sapiens
<220> FEATURE:
<221> NAME/KEY: MISC_FEATURE
<223> OTHER INFORMATION: >CD26 EPITOPE 12

<400> SEQUENCE: 157

Ser Cys Glu Leu Asn Pro Glu Arg Cys Gln Tyr Tyr
1               5                   10


<210> SEQ ID NO 158
<211> LENGTH: 6
<212> TYPE: PRT
<213> ORGANISM: Homo sapiens
<220> FEATURE:
<221> NAME/KEY: MISC_FEATURE
<223> OTHER INFORMATION: >CD26 EPITOPE 13

<400> SEQUENCE: 158

Ser Gly Pro Gly Leu Pro
1               5


<210> SEQ ID NO 159
<211> LENGTH: 5
<212> TYPE: PRT
<213> ORGANISM: Homo sapiens
<220> FEATURE:
<221> NAME/KEY: MISC_FEATURE
<223> OTHER INFORMATION: >CD26 EPITOPE 14

<400> SEQUENCE: 159

Ala Thr Gln Glu Arg
1               5
```